US010155038B2

(12) United States Patent
Rabinovich et al.

(10) Patent No.: US 10,155,038 B2
(45) Date of Patent: Dec. 18, 2018

(54) CELLS PREPARED BY TRANSIENT TRANSFECTION AND METHODS OF USE THEREOF

(71) Applicant: Yale University, New Haven, CT (US)

(72) Inventors: Peter M. Rabinovich, Madison, CT (US); Sherman M. Weissman, New Haven, CT (US); Marina E. Komarovskaya, Milford, CT (US); Erkut Bahceci, Hamden, CT (US); Samuel Katz, Woodbridge, CT (US); Efim Golub, East Haven, CT (US)

(73) Assignee: Yale University, Hew Haven, CT (US)

( * ) Notice: Subject to any disclaimer, the term of this patent is extended or adjusted under 35 U.S.C. 154(b) by 0 days.

(21) Appl. No.: 15/008,376

(22) Filed: Jan. 27, 2016

(65) Prior Publication Data
US 2016/0151491 A1 Jun. 2, 2016

Related U.S. Application Data

(63) Continuation-in-part of application No. 13/019,829, filed on Feb. 2, 2011, now Pat. No. 9,249,423, which is a continuation-in-part of application No. 12/025,700, filed on Feb. 4, 2008, now Pat. No. 8,859,229.

(60) Provisional application No. 60/899,144, filed on Feb. 2, 2007.

(51) Int. Cl.
A61K 9/66 (2006.01)
A61K 39/395 (2006.01)
C12N 15/85 (2006.01)
A61K 45/06 (2006.01)
A61K 48/00 (2006.01)
C12N 5/074 (2010.01)
A61K 39/00 (2006.01)
C12N 5/0781 (2010.01)
C12N 5/0783 (2010.01)
A61K 35/15 (2015.01)
A61K 35/17 (2015.01)

(52) U.S. Cl.
CPC ........ A61K 39/39558 (2013.01); A61K 35/15 (2013.01); A61K 35/17 (2013.01); A61K 39/0011 (2013.01); A61K 45/06 (2013.01); A61K 48/005 (2013.01); C12N 5/0635 (2013.01); C12N 5/0638 (2013.01); C12N 5/0646 (2013.01); C12N 5/0696 (2013.01); C12N 15/85 (2013.01); A61K 2039/5156 (2013.01); A61K 2039/5158 (2013.01); C12N 2501/602 (2013.01); C12N 2501/603 (2013.01); C12N 2501/604 (2013.01); C12N 2501/606 (2013.01); C12N 2506/094 (2013.01); C12N 2506/1307 (2013.01); C12N 2510/00 (2013.01); C12N 2830/008 (2013.01)

(58) Field of Classification Search
CPC .. A61K 39/39558; A61K 35/17; A61K 35/15; A61K 39/0011; A61K 48/005; A61K 45/06; A61K 2039/5158; A61K 2039/5156; C12N 5/0638; C12N 5/0646; C12N 5/0696; C12N 15/85; C12N 2506/094; C12N 2506/1307; C12N 2501/602; C12N 2510/00; C12N 2501/606; C12N 2501/604; C12N 2501/603; C12N 2830/008; C12N 5/0635
See application file for complete search history.

(56) References Cited

U.S. PATENT DOCUMENTS

| 4,394,448 A | 7/1983 | Szoka |
| 4,619,794 A | 10/1986 | Hauser |
| 4,946,778 A | 8/1990 | Ladner |
| 5,091,513 A | 2/1992 | Huston |
| 5,250,431 A | 10/1993 | Rudd |
| 5,256,555 A | 10/1993 | Milburn |
| 5,359,046 A | 10/1994 | Capon |
| 5,686,281 A | 11/1997 | Roberts |
| 5,712,149 A | 1/1998 | Roberts |
| 5,747,292 A | 5/1998 | Greenberg |

(Continued)

FOREIGN PATENT DOCUMENTS

| WO | 9914346 | 3/1999 |
| WO | 0014257 | 3/2000 |

(Continued)

OTHER PUBLICATIONS

Arnaud-Barbe, "Transcription of RNA templates by T7 RNA polymerase", Nuc. Acids Res., 26(15):3550-3554 (1998).

(Continued)

Primary Examiner — Valarie E Bertoglio
(74) Attorney, Agent, or Firm — Pabst Patent Group LLP

(57) ABSTRACT

Compositions and methods of making cells using RNA, and cells made using the disclosed compositions and methods are also provided. In exemplary embodiments, RNA is transfected into cells to effect a molecular, biological, physiological, or histological change in the cells. In preferred embodiments, the RNA is prepared in vitro, more preferably using a DNA template according to the provided compositions and methods. Methods for treating or inhibiting a disorder or disease such cancer are also provided. The methods can include, for example, locally or systemically administering to the host an effective amount of one or more RNAs; or an effective amount of population of cells isolated from the subject or a syngeneic or histocompatible subject, contacted ex vivo with one or RNAs, and optionally expanded. The cells can be, for example, immune cells or stem cells.

18 Claims, 17 Drawing Sheets

(56) References Cited

U.S. PATENT DOCUMENTS

| | | |
|---|---|---|
| 5,807,707 A | 9/1998 | Andrews |
| 5,837,693 A | 11/1998 | German |
| 5,840,304 A | 11/1998 | Davis |
| 5,858,740 A | 1/1999 | Finer |
| 5,861,314 A | 1/1999 | Philip |
| 5,912,172 A | 6/1999 | Eshhar |
| 6,103,521 A | 8/2000 | Capon |
| 6,355,476 B1 | 3/2002 | Kwon |
| 6,407,221 B1 | 6/2002 | Capon |
| 6,410,319 B1 | 6/2002 | Raubitschek |
| 6,825,325 B1 | 11/2004 | Fischer |
| 7,049,136 B2 | 5/2006 | Seed |
| 7,070,995 B2 | 7/2006 | Jensen |
| 7,323,553 B2 | 1/2008 | Fahrner |
| 7,435,596 B2 | 10/2008 | Campana |
| 7,446,179 B2 | 11/2008 | Jensen |
| 7,514,537 B2 | 4/2009 | Jensen |
| 8,026,097 B2 | 9/2011 | Campana |
| 8,071,374 B2 | 12/2011 | Har-Noy |
| 8,399,645 B2 | 3/2013 | Campana |
| 8,859,229 B2 | 10/2014 | Rabinovich |
| 9,249,423 B2 | 2/2016 | Rabinovich |
| 9,605,049 B2 | 3/2017 | Campana |
| 2002/0001841 A1 | 1/2002 | Kaltoft |
| 2002/0018749 A1 | 2/2002 | Hudson |
| 2003/0083272 A1 | 5/2003 | Wiederholt |
| 2003/0087846 A1 | 5/2003 | Wolpert |
| 2003/0148982 A1 | 8/2003 | Brenner |
| 2004/0038886 A1 | 2/2004 | Finney |
| 2004/0043401 A1 | 3/2004 | Sadelain |
| 2004/0058445 A1 | 3/2004 | Ledbetter |
| 2005/0113564 A1 | 5/2005 | Campana |
| 2006/0029595 A1 | 2/2006 | Kwon |
| 2006/0078994 A1 | 4/2006 | Healey |
| 2006/0127985 A1 | 6/2006 | Goodwin |
| 2006/0188490 A1 | 8/2006 | Hoerr |
| 2008/0152586 A1 | 6/2008 | Hudson |
| 2008/0260706 A1 | 10/2008 | Rabinovich |
| 2008/0311076 A1 | 12/2008 | Spencer |
| 2009/0136498 A1 | 5/2009 | Haurum |
| 2009/0191172 A1 | 7/2009 | Cooper |
| 2009/0196877 A1 | 8/2009 | Chen |
| 2009/0226404 A1 | 9/2009 | Schuler |
| 2009/0257991 A1 | 10/2009 | Li |
| 2009/0263421 A1 | 10/2009 | Spetz-Holmgren |
| 2011/0038836 A1 | 2/2011 | Cooper |
| 2011/0044939 A1 | 2/2011 | Feuerer |
| 2011/0059056 A1 | 3/2011 | Grawunder |
| 2011/0070219 A1 | 3/2011 | Seefeldt |
| 2011/0091936 A1 | 4/2011 | Gawlitzek |
| 2011/0104128 A1 | 5/2011 | Cooper |
| 2011/0143436 A1 | 6/2011 | Dahl |
| 2011/0287979 A1 | 11/2011 | Gurney |
| 2011/0300179 A1 | 12/2011 | Spetz-Holmgren |
| 2012/0015434 A1 | 1/2012 | Campana |
| 2012/0134970 A1 | 5/2012 | Yang |
| 2013/0071414 A1 | 3/2013 | Dotti |
| 2013/0216509 A1 | 8/2013 | Campana |
| 2013/0266551 A1 | 10/2013 | Campana |
| 2014/0050709 A1 | 2/2014 | Leen |
| 2014/0328812 A1 | 11/2014 | Campana |
| 2014/0341869 A1 | 11/2014 | Campana |
| 2015/0017120 A1 | 1/2015 | Wittrup |
| 2015/0283178 A1 | 10/2015 | June |
| 2015/0290244 A1 | 10/2015 | June |
| 2016/0009784 A1 | 1/2016 | Campana |
| 2016/0151491 A1 | 6/2016 | Rabinovich |
| 2016/0230188 A1 | 8/2016 | Rabinovich |

FOREIGN PATENT DOCUMENTS

| | | |
|---|---|---|
| WO | 0018958 | 4/2000 |
| WO | 2004065546 | 8/2004 |
| WO | 2005044996 | 5/2005 |
| WO | 2006052534 | 5/2006 |
| WO | 2008095141 | 8/2008 |
| WO | 2009077134 | 6/2009 |
| WO | 2009091826 | 7/2009 |

OTHER PUBLICATIONS

Bahceci, "Immunotherapy of B cell malignancies using transiently redirected cytotoxic T cells", Blood, 110(11)Part 1:808A (2007).
Barbour, et al., The nucleotide sequence of a linear plasmid of borrelia burgdorferi reveals similarities to those of circular plasmids of other prokaryotes, J Bacteriology, 178(22):6635-9 (1995).
Boczkowski, "Induction of tumor immunity and cytotoxic T lymphocyte responses using dendritic cells transfected with messenger RNA amplified from tumor cells", Cancer Res., 60(4):1028-1034 (2001).
Buganim, et al., Single-cell gene expression analysis of cellular reprograming reveal a stochastic early and hierarchic late phase, Cell, 150:1209-22 (2012).
Chamberlin, "New RNA polymerase from *Escherichia coli* infected with bacteriophage T7", Nature, 228(5268):227-231 (1970).
Chan, et al., The kalilo linear senescence-inducing plasmid of neurospora is an invertron and encodes DNA and RNA polymerases, 20 Current Genetics, 225-37 (1991).
Cheung, "Anti-Idiotypic antibody facilitates scFv chimeric immune receptor gene transduction and clonal expansion of human lymphocytes for tumor therapy", Hybridoma and Hybridomics, 22(4):209-218 (2003).
Collas, et al., On the way to reprograming cells to pluripotency using cell-free extracts, Reprod Biomed 762-770 (2006).
Cougot, "Cap-tabolism", Trends in Biochem. Sci., 29(8):436-444 (2004).
Davanloo, "Cloning and expression of the gene for bacteriophage T7 RNA polymerase", Proc. Natl. Acad. Sci. USA, 81(7):2035-2039 (1984).
Djuris and Ellisx, Epigenetics of induced pluripotency, the seven headed dragon, Stem Cell Res Ther, 1:3 1-6 (2010).
Dunn and Studier, "Complete nucleotide sequence of bacteriophage T7 DNA and the locations of T7 genetic elements", J. Mol. Biol., 166(4):477-535 (1983).
Elango, "Optimized transfection of mRNA transcribed from a d(A/T)100 tail-containing vector", Biochem. Biophys. Res. Comm., 330(3), 958-966 (2005).
Felgner and Ringold, "Cationic liposome-mediated transfection", Nature, 337(6205):387-388 (1989).
Fuke and Ohno, Role of poly (A) tail as an identity element for mRNA nuclear export, Nucl Acids Res., 36:1037-49 (2008).
Hanna, et al., Direct reprograming of terminally differentiated mature B lymphocytes pluripotency, Cell, 133:250-64 (2008).
Holtkamp, "Modification of antigen-encoding RNA increases stability, translational efficacy, and T-cell stimulatory capacity of dendritic cells", Blood, 108(13):4009-4017 (2006).
Imai, "Chimeric receptors with 4-1BB signaling capacity provoke potent cytotoxicity against acute lymphoblastic leukemia", Leukemia,18(4):676-684 (2004).
Imai, "Genetic modification of primary natural killer cells overcomes inhibitory signals and induces specific killing of leukemic cells", Blood, 106(1):376-383 (2005).
Karlock, et al., Mutations in the yeast mitochondrial RNA polymerase specificity factor, Mtf1, verify an essential role in promoter utilization, J Biol Chem., 277(31):28143-9 (2002).
Kiyama and Oishi, "In vitro transcription of a poly(dA) x ppty(dT)-containing sequence is inhibited by interaction between the template and its transcripts", Nucleic Acids Res., 24(22):4577-4583 (1996).
Kiyama, "Instability of plasmid DNA maintenance caused by transcription of poly(dT)-containing sequences in *Escherichia coli*", Gene, 150(1):57-61 (1994).
Kotani, "Improved methods of retroviral vector transduction and production for gene therapy", Hum. Gene Ther., 5(1):19-28 (1994).
Kowolik, "CD28 costimulation provided through a CD19-specific chimeric antigen receptor enhances in vivo persistence and antitumor efficacy of adoptively transferred T cells", Cancer Res., 66(22):10995-11004 (2006).

(56) References Cited

OTHER PUBLICATIONS

Le Dantrec, et al., Genomic sequence and transcriptional analysis of a 23-kilobase mycobacterial linear plasmid; Evidence for horizontal transfer and identification of plasmid maintenance systems , J Bacteriology, 183(7):2157-64.
Lee, "Efficient autointegration of avian retrovirus DNA in vitro", J. Virol., 64(12):5958-5965 (1990).
Liu, "Development and validation of a T7 based linear amplification for genomic DNA", BMC Genomics, 4(1):19 (2003).
MacDonald, "Termination and slippage by bacteriophage T7 RNA polymerase", J. Mol. Biol., 232(4):1030-1047 (1993).
Mackett, "General method for production and selection of infectious vaccinia virus recombinants expressing foreign genes", J. Virol., 49(3):857-864 (1984).
Maherali, et al., Guideline and techniques for the generation of induced pluripotent stem cells , Stem Cell, 3:596-605 (2008).
Mielke, et al., Stabilized long-term expression of heterodimeric proteins from tricistronic mRNA , Gene, 254:1-6 (2000).
Mochizuki, et al., The large linear plasmid pSLA2-L of Streptomyces rochel has an unusually condensed gene organization for secondary metabolism , Mole Microbiol., 48(6):1501-10 (2003).
Muhlrad and Parker, Aberrant mRNAs with extended 3 UTRa are substrates for rapid degradation by mRNA surveillance ,RNA,5:1299-307 (1999).
Nacheva and Berzal-Herranz, "Preventing nondesired RNA-primed RNA extension catalyzed by T7 RNA polymerase", Eur. J. Biochem., 270(7):1458-1465 (2003).
Nair, et al., "Induction of primary carcinoembryonic antigen (CEA)-specific cytoxic T lymphocytes in vitro using human dendritic cells transfected with RNA", Nature Biotechnology, 16(4):364-369 (1998).
Nakano, "Efficient coupled transcription/translation from PCR template by a hollow-fiber membrane bioreactor", Biotechnol. Bioeng., 64(2):194-199 (1999).
Nienhuls, et al, Genotoxicity of Retroviral integration in hematopoietic cells , Mole Therapy, 13:1031-49 (2006).
Nishikawa, "Nonviral vectors in the new millennium: delivery barriers in gene transfer", Hum. Gene Ther., 12(8):861-870 (2001).
Pestova, "Molecular mechanisms of translation initiation in eukaryotes", Proc. Natl. Acad. Sci., 98(13):7029-7036 (2001).
Plath and Lowry, et al., Progress in understanding reprograming to induced pluripotent state , Nature Reviews, 12:253-65 (2011).
Rabinovich, "Synthetic messenger RNA as a tool for gene therapy", Human Gene Therapy, 17(10):1027-1035 (2006).
Saeboe-Larssen, "mRNA-based electrotransfection of human dendritic cells and induction of cytotoxic T lymphocyte responses against the telomerase catalytic subunit (hTERT)", J. Imm. Methods, 259(1-2):191-203 (2002).
Saltzman and Desai, "Drug delivery in the BME curricula", Annals of Biomedical Engineering, 34(2):270-275 (2006).
Santopiatro, et al., Cloning and nucleotide sequence of a linear DNA plasmid from xanthophyfiomyces dendrorhous (pfaffia rhodozyma) , Folia Microbiol., 46(4):277-88 (2001).
Sasaki, et al., "Translation initiation at the CUU codon is mediated by the internal ribosome entry site of an insect picoma-like virus in vitro", J. of Virology, 73:129-1226 (1999).
Schenborn and Mierendorf, "A novel transcription property of SP6 and T7 RNA polymerases: dependence on template structure", Nuc Acids Res., 13(17):6223-6236 (1985).
Schultze, "Follicular lymphomas can be induced to present alloantigen efficiently: a conceptual model to improve their tumor immunogenicity", Proc. Natl. Acad. Sci., 92(18):8200-8204 (1995).
Shiramizu, "Identification of a common clonal human immunodeficiency virus integration site in human immunodeficiency virus-associated lymphomas", Cancer Res., 54(8):2069-2072 (1994).
Spratt, "The lognormal frequency distribution and human cancer", J. Surgical Research, 9(3):151-157 (1969).
Stadtfeld, et al., Defining molecular cornerstones during fibroblast to IPS cell reprograming in mouse , Cell Stem Cell, 2:230-40 (2008).

Stepinski, "Synthesis and properties of mRNAs containing the novel "anti-reverse" cap analogs 7-methyl(3'-O-methyl)GpppG and 7-methyl (3'-deoxy)GpppG", RNA, 7(10):1486-1495 (2001).
Sullivan, et al., Elucidating nuclear reprogramming mechanisms: taking a synergistic approach , Reprod Biomed. Online, 165(1);41-50 (2008).
Takahashi, et al., Induction of pluripotent stem cells from mouse embryonic and adult fibroblast cultures by defined factors , Cell, 128:663-76 (2006).
Triana-Alonso, "Self-coded 3'-extension of run-off transcripts produces aberrant products during in vitro transcription with T7 RNA polymerase", J. Biol. Chem., 270(11):6298-6307 (1995).
Verma and Somia, "Gene therapy—promises, problems and prospects", Nature, 389(6648):239-242 (1997).
Vlachakis, et al., "Meis3 synergizes with Pbx4 and Hoxb1b in promoting hindbrain fates in the zebrafish",Development, 128:1299-1312 (2001).
Wahie, Poly (A) tail length control is caused by termination of progressive synthesis , J Biol Chem., 270:2800-8 (1995).
Warren, et al., "Highly efficient reprogramming to pluripotency and directed differentiation of human cells with synthetic modified mRNA", Cell Stem Cell, 7:618-30 (2010).
Wolff, "Direct gene transfer into mouse muscle in vivo", Science, 247(4949 Pt 1):1465-1468 (1990).
Yakubov, et al., Reprogramming of human fibroblasts to pluripotent stem cells using mRNA of four transcription factors , Biochem Biophys Res., 394:189-9 (2010).
Yamanaka, "Induction of pluripotent stem cells from mouse fibroblasts by four transcription factors", Cell Prolif., 41(Suppl 1):51-56 (2008).
Yu, "Induced pluripotent stem cell lines derived from human somatic cells", Science, 318(5858):1917-1920 (2007).
Yu, "Structural and functional analysis of an mRNP complex that mediates the high stability of human beta-globin mRNA", Molecular and Cellular Biology, 21(17):5879-5888 (2001).
Cooper, et al., "T-cell clones can be rendered specific for CD19: toward the selective augmentation of the graft-versus-B-lineage leukemia effect", Blood, 101(4):1637-4405-17 (2003).
Ahuja, et al., "Depletion of B cells in murine lupus: efficacy and resistance", J Immunology, 179:3351-3361 (2007).
Barber, et al., "Chimeric NKG2D receptor-expressing T cells as an immunotherapy for multiple myeloma", Exp Hematol., 36:1318-28 (2008).
Barrett, et al., "Chimeric antigen receptor therapy for cancer.", Annu Rev Med., 65:333-47 (2014).
Barrett, et al., "Regimen-specific effects of RNA-modified chimeric antigen receptor T cells in mice with advanced leukemia", Hum Gene Ther., 24:717-27 (2013).
Barry, et al., "Granzyme B short-circuits the need for caspase 8 activity during granule-mediated cytotoxic T-lymphocyte killing by directly cleaving Bid", Mol Cell Biol., 20:3781-94 (2000).
Beatty, et al., "Mesothelin-specific chimeric antigen receptor mRNA-engineered T cells induce anti-tumor activity in solid malignancies", Cancer Immunol Res., 2:12-120 (2014).
Begley, et al., "Immunosensitization with a Bcl-2 small molecule inhibitor", Cancer Immunol Immunother, 58:699-708 (2009).
Berger, et al., "Analysis of transgene-specific immune responses that limit the in vivo persistence of adoptively transferred HSV-TK-modified donor T cells after allogeneic hematopoietic cell transplantation", Blood, 107:2294-302 (2006).
Biagi, et al., "Chimeric T-cell receptors: New challenges for targeted immunotherapy in hematologic malignancies", Haematologica, 92:381-88 (2007).
Bonini, et al., "HSV-TK gene transfer into donor lymphocytes for control of allogeneic graft-versus-leukemia", Science, 276:1719-24 (1997).
Brawerman, et al "The role of the poly(A) sequence in mammalian messenger RNA", Crit Rev Biochem., 10:1-38 (1981).
Brentjens, et al., "CD19-targeted T cells rapidly induce molecular remissions in adults with chemotherapy-refractory acute lymphoblastic leukemia", Sci Transl Med., 5:177ra38 (2013).

(56) References Cited

OTHER PUBLICATIONS

Brentjens, et al., "Eradication of systemic B-cell tumors by genetically targeted human T lymphocytes co-stimulated by CD80 and interieukin-15", Nat Med., 9:279-86 (2003).
Brown, et al., "Stem-like tumor-initiating cells isolated from IL13Rα2 expressing gliomas are targeted and killed by IL13-zetakine-redirected T Cells" Clin Cancer Res., 18(8):2199-209 (2012).
Carreno, et al., "The B7 family of ligands and its receptors: new pathways for costimulation and inhibition of immune responses", Annu Rev Immunol, 20:29-53 (2002).
Cartellieri, et al., "Chimeric Antigen Receptor-Engineered T Cells for Immunotherapy of Cancer", J Biomed Biotech., 2010, Article ID 956304, 13 pages doi:10.1155/2010/956304 (2010).
Charo, et al., "Bcl-2 overexpression enhances tumor-specific T-cell survival", Cancer Res., 65(5):2001-8 (2005).
Chen, et al., "Anti-PD-1/PD-L1 therapy of human cancer: past, present, and future", J Clin Invest.,125:3384-91 (2015).
Chen, et al., "Oncology meets immunology: the cancer-immunity cycle", Immunity, 39:1-10 (2013).
Chmielewski, et al., T cell activation by antibody-like immunoreceptors: increase in affinity of the single-chain fragment domain above threshold does not increase T cell activation against antigen-positive target cells but decreases selectivity J Immunol., 173:7647-7653 (2004).
Chougnet, et al., "A major role for Bim in regulatory T cell homeostasis.", J Immunol., 186:156-63 (2011).
Cooper, et al., "Enhanced antilymphoma efficacy of CD19-redirected influenza MP2-specific CTLs by cotansfer of T cells modified to present influenza MP1", Blood, 105:1622-31 (2005).
Cooper, et al., "Manufacturing of gene-modified cytotoxic T lymphocytes for autologous cellular therapy for lymphoma", Cytotherapy, 8:105-17 (2006).
Curran, et al., "Chimeric antigen receptors for T cell immunotherapy: current understanding and future directions", J Gene Med., 14:405-15 (2012).
Davies, et al., "Flexible targeting of ErbB dimers that drive tumorigenesis by using genetically engineered T cells", Mol Med., 18:565-76 (2012).
Dotti, "The other face of chimeric antigen receptors", Mol Ther., 22(5):899-900 (2014b).
Dotti, et al., "Design and development of therapies using chimeric antigen receptor-expressing T cells", Immunol Rev., 257(1):107-26 (2014).
Du, et al., "New immunotoxins targeting CD123, a stem cell antigen on acute myeloid leukemia cells", J Immunother, 30:607-13 (2007).
Dudley and Rosenberg, "Afoptive cell transfer therapy", Semin Oncol., 34:524-31 (2007).
Dudley, et al., "A phase I study of nonmyeloablative chemotherapy and adoptive transfer of autologous tumor antigen-specific T lymphocytes in patients with metastatic melanoma", J Immunother., 25:243-51 (2002).
Eaton, et al., "Retroviral transduction of human peripheral blood lymphocytes with Bcl-X(L) promotes in vitro lymphocyte survival in pro-apoptotic conditions", Gene Therapy, 9:527-35 (2002).
Ehninger, et al., "Distribution and levels of cell surface expression of CD33 and CD123 in acute myeloid leukemia", Blood Cancer J., 4:e218 (2014).
Elango, et al., "Optimized transfection of mRNA trianscribed from a d(A/T) 100 tail-containing vector", Biochem Biophys Res Commun., 330:958-66 (2005).
Eshhar, et al., "Functional expression of chimeric receptor genes in human T cells", J Immunol Methods, 248:67-76 (2001).
Fedorov, et al., "PD-1- and CTLA-4-based inhibitory chimeric antigen receptors (iCARs) divert off-target immunotherapy responses", Sci Transl Med., 5:215ra172 (2013).
Ferber, "Gene therapy: Safer and virus free", Science, 294:1638-42 (2001).
Finney, et al., "Chimeric receptors providing both primary and costimulatory signaling in T cells from a single gene product", J Immunol., 161:2791-7 (1998).

Gattinoni, et al., "Acquisition of full effector function in vitro paradoxically impairs the in vivo antitumor efficacy of adoptively transferred CD8 T cells", J Clin Invest., 115:1616-26 (2005).
Gavathiotis, et al., "BAX activation is initiated at a novel interaction site", Nature, 455:1076-81 (2008).
Gilbert, et al., "CRISPR-mediated modular RNA-guided regulation of transcription in eukaryotes", Cell, 154:442-51 (2013).
Gill, et al., "Going viral: chimeric antigen receptor T-cell therapy for hematological malignancies", Immunol Rev.,263:68-89 (2015).
Grada, et al., "TanCAR: A Novel Bispecific Chimeric Antigen Receptor for Cancer Immunotherapy", Mol Ther Nucleic Acids, 2:e105 (2013).
Greenwald, et al., "The B7 family revisited", Annu Rev Immunol, 23:515-48 (2005).
Griffiths, et al., "Herpesvirus saimiri-based gene delivery vectors", Curr Gene Ther., 6:1-15 (2006).
Gross, and Eshhar, "Endowing T cells with antibody specificity using chimeric T cell receptors", FASEB, 6:3370-8 (1992).
Hacein-Bey-Abina, et al., "A serious adverse event after successful gene therapy for X-linked severe combined immunodeficiency", NEJM, 348:255-6 (2003).
Haynes, et al., "Redirecting mouse CTL against colon carcinoma: superior signaling efficacy of single-chain variable domain chimeras containing TCR-zeta vs Fc epsilon RI-gamma", J Immunol., 166:182-7 (2001).
Heemskerk, et al., "Adoptive cell therapy for patients with melanoma, using tumor-infiltrating lymphocytes genetically engineered to secrete interleukin-2", Hum Gene Ther., 19:496-510 (2008).
Herweijer and Wolff, "Progress and prospects: naked DNA gene transfer and therapy", Gene Ther. 10(6):453-8 (2003).
Hinrichs, et al., "Exploiting the curative potential of adoptive T-cell therapy for cancer", Immunol Rev., 257:56-71 (2014).
Hombach, et al., "T cell activation by recombinant FcepsilonRI gamma-chain immune receptors: an extracellular spacer domain impairs antigen-dependent T cell activation but not antigen recognition", Gene Ther., 7:1067-75 (2000).
Hudecek, et al., "Receptor affinity and extracellular domain modifications affect tumor recognition by ROR1-specific chimeric antigen receptor T cells", Clin Cancer Res., 19:3153-64 (2013).
Hunter, et al., "Chimeric γc cytokine receptors confer cytokine independent engraftment of human T lymphocytes", Mol Immunol., 56:1-11 (2013).
Irving, et al., "The cytoplasmic domain of the T cell receptor zeta chain is sufficient to couple to receptor-associated signal transduction pathways", Cell, 64:891-901 (1991).
Jensen, et al., "Design and implementation of adoptive therapy with chimeric antigen receptor-modified T cells", Immunol Rev., 257(1):127-44 (2014).
Kahlon, et al., "Specific recognition and killing of glioblastoma multiforme by interleukin 13-zetakine redirected cytolytic T cells", Cancer Res., 64:9160-6 (2004).
Kalos, et al., "T cells with chimeric antigen receptors have potent antitumor effects and can establish memory in patients with advanced leukemia", Sci Transl Med., 3:95ra73 (2011).
Kapp and Lorsch, "The molecular mechanics of eukaryotic translation", Annu Rev Biochem., 73:657-704 (2004).
Karlsson, et al., "Combining CAR T cells and the Bcl-2 family apoptosis inhibitor ABT-737 for treating B-cell malignancy", Cancer Gene Therapy, 20:386-93 (2013).
Kavanagh, et al., "Expansion of HIV-specific CD4 and CD8 T cells by dendritic cells transfected with MRNA encoding cytoplasm- or lyso-some-targeted net", Blood, 107:1963-9 (2006).
Keir, et al., "PD-1 and its ligands in tolerance and immunity", Annu Rev Immunol, 26:677-704 (2008).
Kenderian, et al., "CD33-specific chimeric antigen receptor T cells exhibit potent preclinical activity against human acute myeloid leukemia", Leukemia, 29(8):1637-47 (2015).
Kershaw, et al., "Supernatural T cells: genetic modification of T cells for cancer therapy", Nat Rev Immunol., 5:928-40 (2005).
Kochenderfer, et al., "Donor-derived CD19-targeted T cells cause regression of malignancy persisting after allogeneic hematopoietic stem cell transplantation", Blood, 122:4129-39 (2013).

(56) References Cited

OTHER PUBLICATIONS

Kochenderfer, et al., "Treating B-cell cancer with T cells expressing anti-CD19 chimeric antigen receptors", Nat Rev Clin Oncol, 10:267-76 (2013b).

Kong, et al., "Suppression of human glioma xenografts with second-generation IL13R-specific chimeric antigen receptor-modified T cells", Clin Cancer Res., 18:5949-60 (2012).

Kuwana, et al., "Expression of chimeric receptor composed of immunoglobulin-derived V regions and T-cell receptor-derived C regions", Biochem Biophys Res Commun., 149:960-8 (1987).

Labelle, et al., "A stapled BIM peptide overcomes apoptotic resistance in hematologic cancers", J Clin Invest., 122(6):2018-31 (2012).

Lamers, et al., "Treatment of metastatic renal cell carcinoma with CAIX CAR-engineered T cells: clinical evaluation and management of on-target toxicity", Mol Ther., 21:904-12 (2013).

Larson, et al., "CRISPR interference (CRISPRi) for sequence-specific control of gene expression", Nat Protoc, 8:2180-96 (2013).

Leahy, "A structural view of CD4 and CD8", FASEB,9:17-25 (1995).

Li, et al., "Apoptosis induced by DNA uptake limits transfection efficiency", Exp Cell Res., 253:541-50 (1999).

Li, et al., "Cleavage of BID by caspase 8 mediates the mitochondrial damage in the Fas pathway of apoptosis", Cell, 94:491-501 (1998).

Luo, et al., "Bid, a Bcl2 interacting protein, mediates cytochrome c release from mitochondria in response to activation of cell surface death receptors", Cell, 94:481-90 (1998).

Maher, "Immunotherapy of malignant disease using chimeric antigen receptor engrafted T cells", ISRN Oncol. 2012:278093 (2012).

Marin, et al., "Enhancement of the anti-leukemic activity of cytokine induced killer cells with an anti-CD19 chimeric receptor delivering a 4-1BB-C activity signal", Exp Hematol., 35:1388-97 (2007).

Mihara, et al., "Chimeric receptors with 4-1BB signaling capacity provoke potent cytotoxicity against acute lymphoblastic leukemia", Leukemia, 18:676-84 (2004).

Mizui, et al., "IL-2 protects lupus-prone mice from multiple end-organ damage by limiting CD4-CD8-IL-17-producing T cells", J Immunol.,193:2168-77 (2014).

Modak, et al., "Monoclonal antibody 8H9 targets a novel cell surface antigen expressed by a wide spectrum of human solid tumors", Cancer Res., 61:4048-54 (2001).

Moeller, et al., "A functional role for CD28 costimulation in tumor recognition by single-chain receptor-modified T cells", Cancer Gene Ther., 11:371-9 (2004).

Morgan, et al., "Case report of a serious adverse event following the administration of T cells transduced with a chimeric antigen receptor recognizing ERBB2", Mol Ther., 18:843-51 (2010).

Morris, et al., "Generation of tumor-specific T-cell therapies", Blood Rev., 20:61-9 (2006).

Muranski, et al., "Increased intensity lymphodepletion and adoptive immunotherapy—how far can we go?", Oncology, 3:668-81 (2006).

National Cancer Institute. "CAR T-cell therapy: engineering patients immune cells to treat their cancers", 3 pages, http://www.cancer.gov/about-cancer/treatment/research/car-t-cells, retrieved Nov. 11, 2015.

Oltersdorf, et al., "An inhibitor of Bcl-2 family proteins induces regression of solid tumours", Nature, 435:677-81 (2005).

Pentcheva-Hoang, et al., "Negative regulators of T-cell activation: potential targets for therapeutic intervention in cancer, autoimmune disease, and persistent infections", Immunol Rev, 229:67-87 (2009).

Pestova, et al., "Molecular mechanisms of translation initiation in eukaryotes", PNAS, 98:7029-36 (2001).

Pizzitola, et al., "Chimeric antigen receptors against CD33/CD123 antigens efficiently target primary acute myeloid leukemia cells in vivo", Leukemia, 28:1596-1605 (2014).

Porter, et al., "Chimeric antigen receptor-modified T cells in chronic lymphoid leukemia", NEJM, 365(8):725-33 (2011).

Rabinovich and Weissman, "Cell engineering with synthetic messenger RNA", Methods Mol Biol., 969:3-28 (2013).

Rabinovich, et al., "Chimeric receptor mRNA transfection as a tool to generate antineoplastic lymphocytes", Human Gene Therapy, 20:51-61 (2009).

Ramos and Dotti, "Chimeric antigen receptor (CAR)-engineered lymphocytes for cancer therapy", Expert Opin Biol Ther., 11:855-73 (2011).

Ren-Heidenreich, et al., "Comparison of the TCR zeta-chain with the FcR gamma-chain in chimeric TCR constructs for T cell activation and apoptosis", Cancer Immunol. Immunother., 51:417-23 (2002).

Rosenberg, "Shedding light on immunotherapy for cancer", NEJM . 350:1461-3 (2004).

Saeboe-Lassen, et al., "mRNA-based electro transfection of human dendritic cells and induction of cytotoxic T lymphocyte responses-against the telomerase catalytic subunit (hTERT)", J Immunol Meth., 259:191-203 (2002).

Scheel-Toellner, et al., "Differential regulation of nuclear and mitochondrial Bcl-2 in T cell apoptosis", Apoptosis, 13:109-117 (2008).

Schumann, et al., "Generation of knock-in primary human T cells using Cas ribonucleoproteins", PNAS, 112:10437-42 (2015).

Schwarz, et al., "ILA, the human 4-1BB homologue, is inducible in lymphoid and other cell lineages", Blood, 85(4):1043-52 (1995).

Shaffer, et al., "T cells redirected against CD70 for the immunotherapy of CD70-positive malignancies", Blood, 117:4304-14 (2011).

So, et al., "Immune regulation and control of regulatory T cells by OX40 and 4-1BB", Cytokine Growth Factor Rev., 198(3-4):253-62 (2008).

Song, et al., "ABT-737 induces expression of the death receptor 5 and sensitizes human cancer cells to TRAIL-induced apoptosis", J Biol Chem., 283:25003-13 (2008).

Souers, et al., "ABT-199, a potent and selective BCL-2 inhibitor, achieves antitumor activity while sparing platelets", Nature Medicine, 19:202-8 (2013).

Sutherland, et al., "SGN-CD33A: a novel CD33-targeting antibody-drug conjugate using a pyrrolobenzodiazepine dimer is active in models of drug-resistant AML", Blood, 122:1455-63 (2013).

Tamada, et al., "Redirecting gene-modified T cells toward various cancer types using tagged antibodies", Clin Cancer Res.,18:6436-45 (2012).

Tarun and Sachs, "A common function for mRNA 5' and 3' ends in translation initiation in yeast", Genes Dev., 9:2997-3007 (1995).

Till, et al., "Adoptive immunotherapy for indolent non-Hodgkin lymphoma and mantle cell lymphoma using genetically modified autologous CD20-specific T cells.", Blood, 112:2261-71 (2008).

Till, et al., "CD20-specific adoptive immunotherapy for lymphoma using a chimeric antigen receptor with both CD28 and 4-1BB domains: pilot clinical trial results", Blood, 119:3940-50 (2012).

Tse, et al., "ABT-263: a potent and orally bioavailable Bcl-2 family inhibitor", Cancer Res, 68:3421-8 (2008).

Urbanska, et al., "A universal strategy for adoptive immunotherapy of cancer through use of a novel T-cell antigen receptor", Cancer Res., 72:1844-52 (2012).

Van Tendeloo, et al., "Highly efficient gene delivery by mRNA electroporation in human hematopoietic cells: superiority to lipofection and passive pulsing of mRNA and to electroporation of plasmid cDNA for tumor antigen loading of demdritic cells",, Blood, 98:49-56 (2001).

Wang, et al., "Treatment of CD33-directed chimeric antigen receptor-modified T cells in one patient with relapsed and refractory acute myeloid leukemia", Mol Ther.,23:184-91 (2015).

Wucherpfennig, et al., "Structural biology of the T-cell receptor: Insights into receptor assembly, ligand recognition, and initiation of signaling", Cold Spring Harb Perspect Biol.,2:a005140 1-14 (2010).

Young, et al., "Viral gene therapy strategies: from basic science to clinical applicatiom", J Pathol., 208:299-318 (2006).

Zetsche, et al., "Cpf1 is a single RNA-guided endonuclease of a class 2 CRISPR-Cas system", Cell, 163(3):759-71 (2015).

Zhang, et al., "Chimeric NK-receptor-bearing T cells mediate antitumor immunotherapy", Blood, 106:1544-51 (2005).

Zhang, et al., "Lymphopenia and interleukin-2 therapy alter homeostasis of CD4+CD25+ regulatory T cells", Nat Med.,11:1238-43 (2005b).

(56) References Cited

OTHER PUBLICATIONS

Loskog, et al., "Addition of the CD28 signaling domain to chimeric T-cell receptors enhances chimeric T-cell resistance to T regulatory cells," Leukemia, 20, 1819-1828 (2006).

(SEQ ID NO:3)

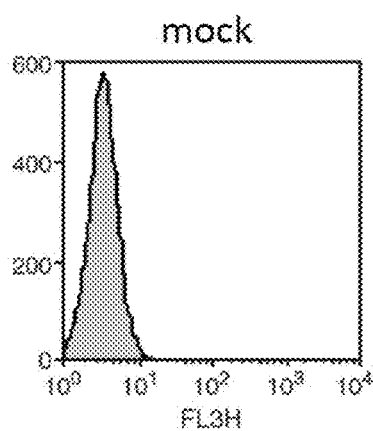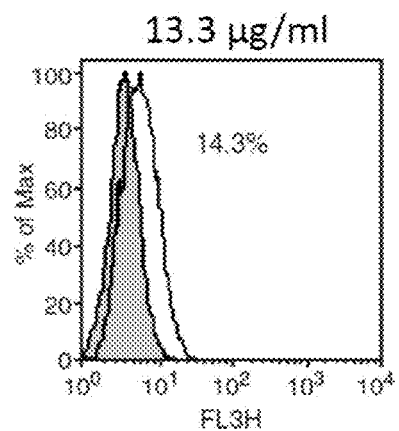
*FIG. 6A*         *FIG. 6B*
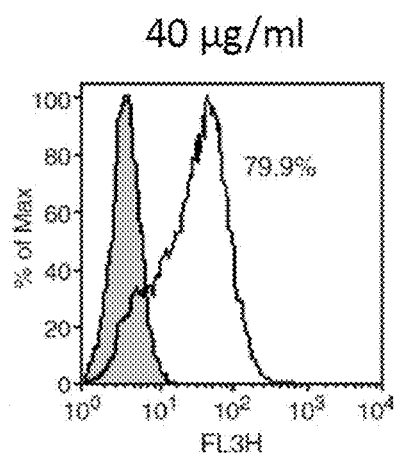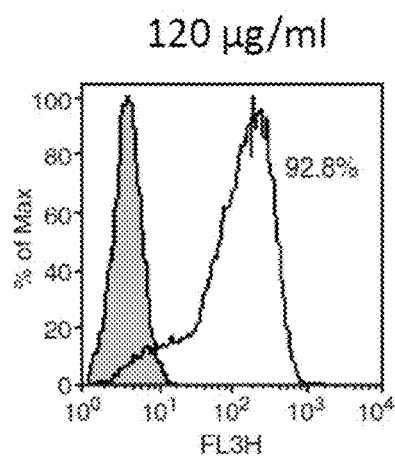
*FIG. 6C*         *FIG. 6D*

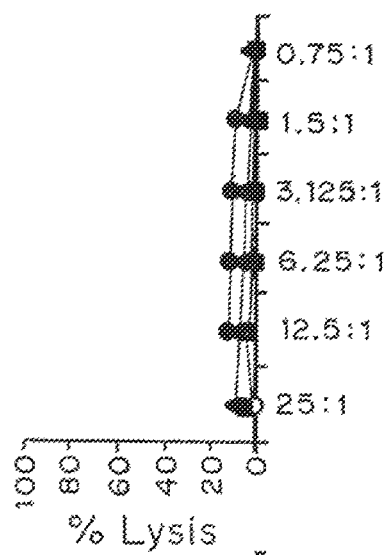
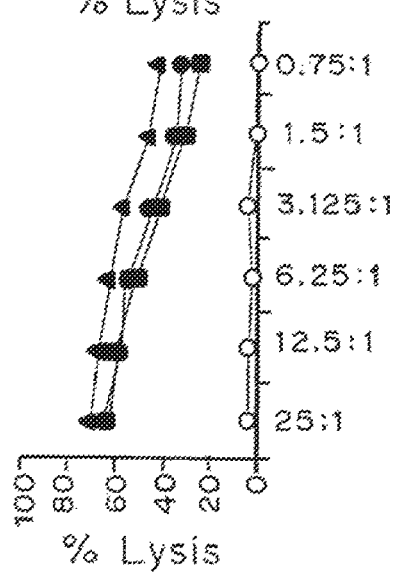
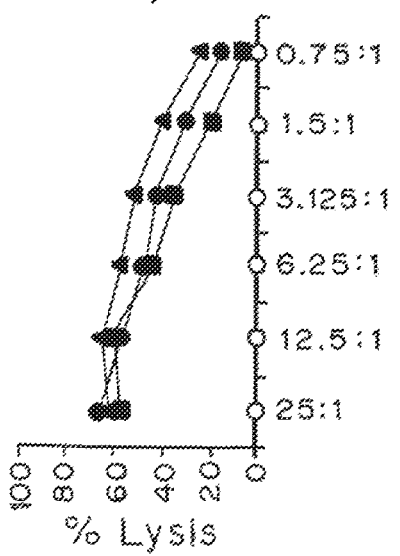
FIG. 6E
FIG. 6F
FIG. 6G

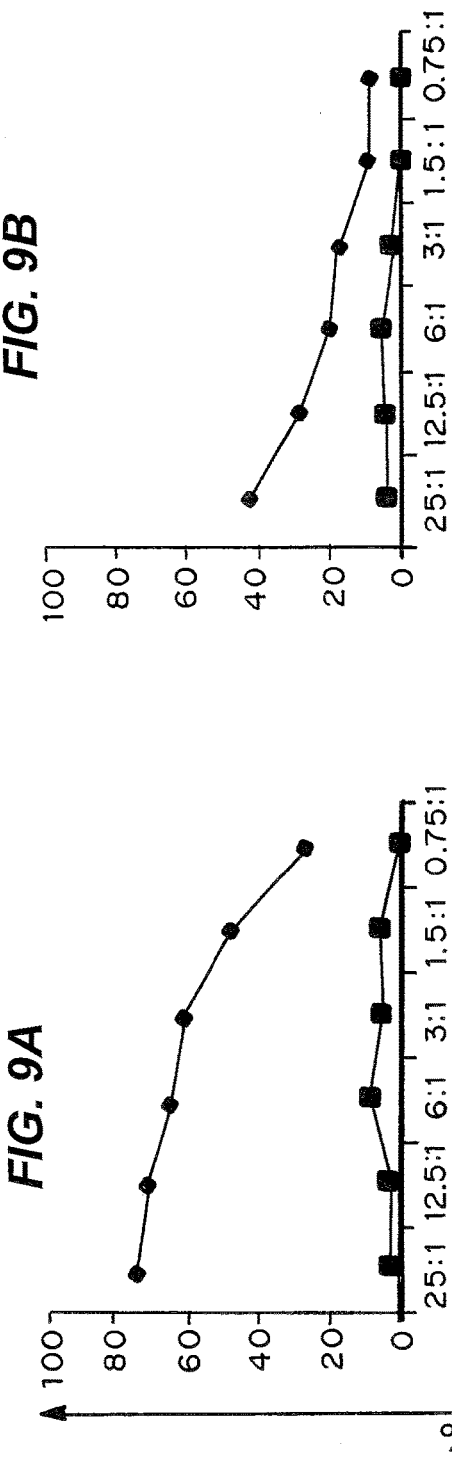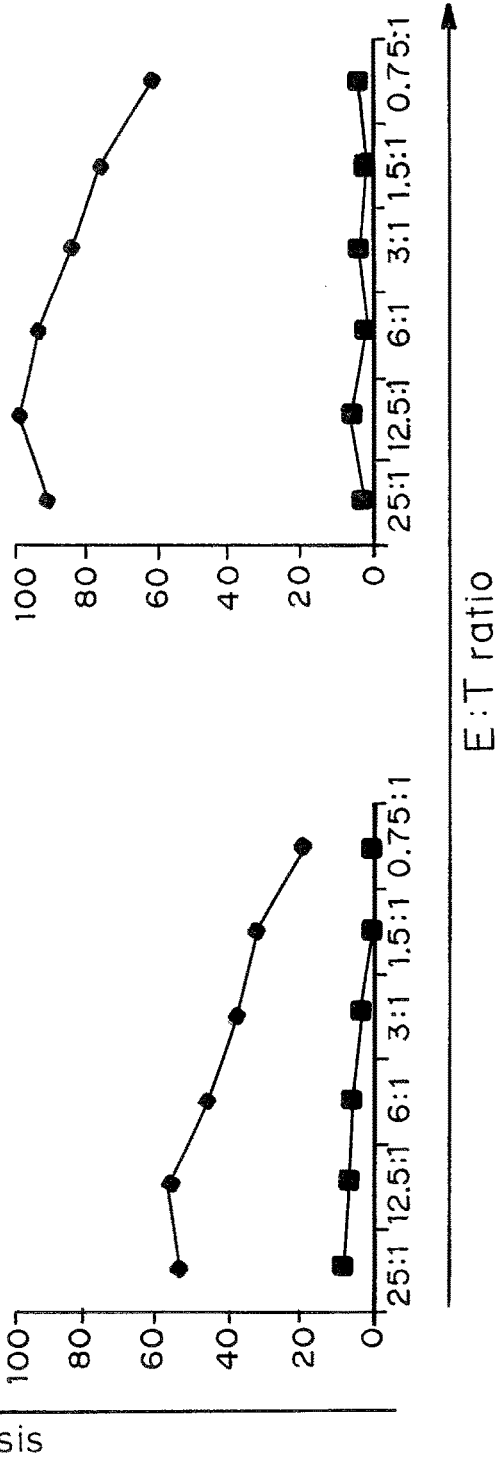

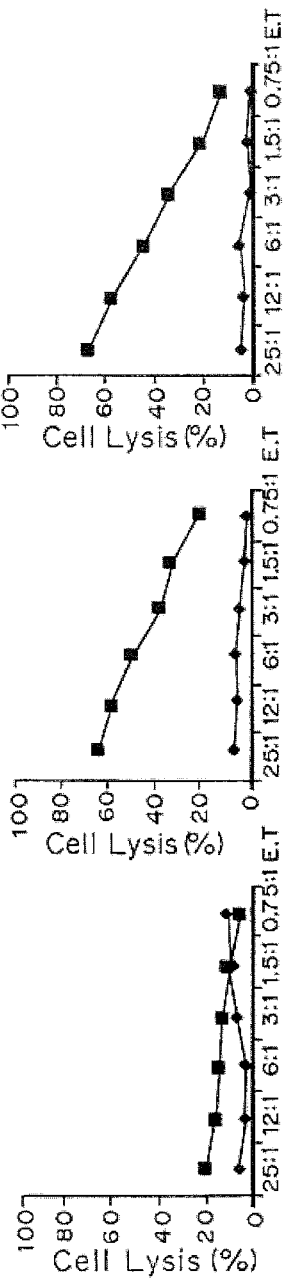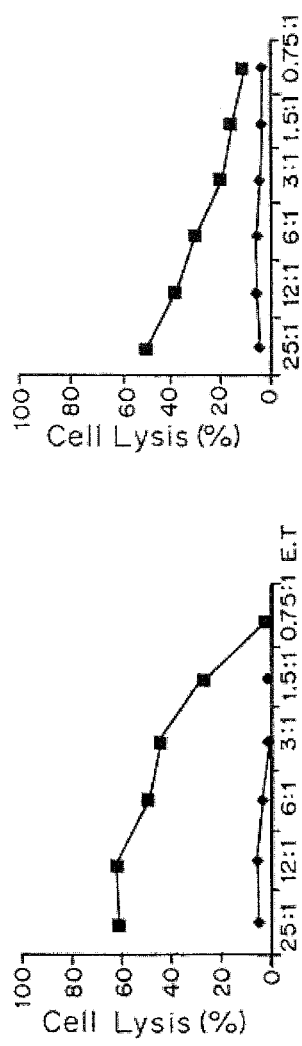
FIG. 10B FIG. 10C FIG. 10D FIG. 10E FIG. 10F

[ABT-737], M

CELLS PREPARED BY TRANSIENT TRANSFECTION AND METHODS OF USE THEREOF

CROSS-REFERENCE TO RELATED APPLICATIONS

This application is a continuation-in-part of U.S. Ser. No. 13/019,829 filed Feb. 2, 2011, now U.S. Pat. No. 9,249,423, which is a continuation-in-part of U.S. Ser. No. 12/025,700 filed Feb. 4, 2008, now issued U.S. Pat. No. 8,859,229, which claims benefit of and priority to U.S. Ser. No. 60/899,144 filed on Feb. 2, 2007, the contents of each of which are incorporated by reference in their entireties.

STATEMENT REGARDING FEDERALLY SPONSORED RESEARCH OR DEVELOPMENT

This invention was made with government support under N01-HV-28186 awarded by the National Institutes of Health, under CA198561 awarded by the National Cancer Institute, and under HG002357 and HG004558 awarded by the National Human Genome Research Institute. The government has certain rights in the invention.

FIELD OF THE INVENTION

The present invention is generally in the field of genetic engineering employing RNA-mediated gene delivery.

BACKGROUND OF THE INVENTION

Adoptive T cell therapy is a breakthrough technology that utilizes ex vivo propagated T cells genetically modified with T cell receptors or with Chimeric Antigen Receptors (CAR) (Rosenberg, *The New England Journal of medicine*, 350: 1461-1463 (2004)), Kershaw, et al., *Nature Review Immunology*, 5:928-940 (2005)). Among these methods, CAR-T cell therapy is the most widely applicable since it allows MHC-independent tumor antigen recognition and T cell activation without the need for co-stimulatory signals (Kochenderfer, et al., *Nat Rev Clin Oncol*, 10:267-276 (2013). The CAR contains an extracellular single-stranded antibody (scFv), a transmembrane anchor, and signaling domains. To date, most CAR-T cell proteins for B-cell malignancies have been designed to recognize CD19, CD20 or ROR1 antigens (Hudecek, et al., *An Official Journal of the American Association for Cancer Research*, 19:3153-64 (2013)); Till, et al., *Blood*, 119:3940-3950 (2012); Jensen, et al., *Immunol Rev*, 257:127-44 (2014)). When expressed on the surface of a T cell, CAR mediates binding to the target tumor antigen and activates T cell cytotoxic response by release of granzymes, perforin and granulysin, as well as expression of Fas ligand, TRAIL and TNF (Kershaw, et al., *Nature Reviews Immunology*, 5:928-940 (2005)). These proteins induce death of target cells through multiple means, for example, through direct caspase-3/7 activation or by indirect caspase-3/7 activation through cleavage and activation of the BH3-only protein BID by granzyme B or Fas and TNF1 triggered caspase-8 activation (Barry, et al., *Molecular and Cellular Biology*, 20:3781-3794 (2000); Li, et al., *Cell*, 94:491-501 (1998); Luo, et al., *Cell*, 94:481-90 (1998)). Early clinical trials of CD19-CAR T cells have demonstrated remarkable efficacy for chronic lymphocytic leukemia (CLL) (Kalos, et al., *Science Translational Medicine*, 3:95ra73 (2011)) and acute lymphocytic leukemia (ALL) (Brentjens, et al., *Science Translational Medicine*, 5:177ra38 (2013)). In addition, limited pre-clinical and clinical success has been shown for MCL with CAR T cells directed against CD20 or CD19 (Hudecek, et al., *An Official Journal of the American Association for Cancer Research*, 19:3153-64 (2013); Till, et al., *Blood*, 119:3940-3950 (2012); Koehenderfer, et al., Blood, 122:4129-39 (2013); Till, et al., *Blood*, 112:2261-2271 (2008)). This approach has been so successful in treating B-Lymphoblastic Leukemia and Chronic Lymphocytic Leukemia, that it has been given special NIH Breakthrough Status (Gill, et al., *Immunological Reviews*, 263:68-89 (2015)).

However, there are several drawbacks of standard methods that reprogram T cells with CAR DNA. First, the approach does not control the in vivo proliferation of T cells and a common complication in several clinical trials has been severe cytokine storm due to uncontrolled CAR-T cell activity (Kalos, et al., *Science Translational Medicine*, 3, 95ra73 (2011)). Second, persistent CD19 CAR-T cells can lead to the permanent depletion of B cells and increased susceptibility to infections (Porter, et al., *The New England Journal of Medicine*, 365:725-733 (2011)). Third, DNA reprogramming requires cells with a high proliferative potential (Jensen, et al., *Immunological Reviews*, 257: 127-144 (2014); Chen, et al., *Immunity*, 39:1-10 (2013); Hinrichs, et al., *Immunological Reviews* 257:56-71 (2014)) which may be difficult to attain especially from some patients. Fourth, CAR T cells infused in patients can be suppressed by the lack of adequate stimulation, and while pre-treatment with lymphotoxic drugs minimizes suppression (Jensen, et al., *Immunological Reviews*, 257: 127-144 (2014)), it considerably increases the toxicity of the treatment. Finally, introduction of CARs by retroviral transduction carries the risk of insertional mutagenesis and oncogene activation (Hacein-Bey-Abina, et al., *The New England Journal of Medicine*, 348:255-256 (2003)).

Non-viral methods of gene delivery were initially developed on DNA models and include electroporation, liposomal, polymer, polypeptide dependent delivery and transfection with "naked" DNA. Electroporation utilizes the application of brief, high-voltage electric pulses to a variety of animal and plant cells and leads to the formation disturbances in the plasma membrane (U.S. Pat. No. 4,394,448 to Szoka, Jr., et al. and U.S. Pat. No. 4,619,794 to Hauser). Nucleic acids can enter directly into the cell cytoplasm either through these, or as a consequence of the redistribution of membrane components that accompanies membrane restoration. Liposomal and polypeptide dependent approaches mix the material to be transferred with non-toxic polymers to form particles able to penetrate cells and to deliver nucleic acids into cytoplasm (Feigner and Ringold, *Nature*, 337:387-388 (1989), Saltzman and Desai, *Annals of Biomedical Engineering*, 34, 270-275 (2006). Polypeptide dependent approaches involve the use of highly penetrating proteins and peptides mixed with a nucleic acid followed by exposure of a target cell to the nucleoprotein/nucleopeptide complex (Verma and Somia, *Nature*, 389:239 (1997); Wolff et al., *Science*, 247:1465 (1990)). "Naked" DNA transfection approaches involve methods where nucleic acids are administered directly in vivo (Herweijer and Wolff, *Gene Ther.* 10(6):453-8 (2003)).

A common disadvantage to known non-viral DNA delivery techniques is that the amount of exogenous protein expression produced relative to the amount of exogenous nucleic acid administered remains too low for most diagnostic or therapeutic procedures. Low levels of protein expression are often a result of a low rate of transfection of the nucleic acid and/or toxicity of exogenous DNA. In addition, some types of cells are very resistant to DNA transfection, and introduced foreign DNA can incorporate into the genome and act as a mutagen.

An alternative procedure for non-viral gene delivery is achieved by transfection of mRNA rather than DNA. In principle, unlike DNA transfection, introducing mRNA can have no permanent effect on the genetic structure of the cell, at least in the absence of rare reverse transcription events. There is limited literature on the application of mRNA transfection approaches (for example, Seaboe-Larssen, et al., *J. Immm. Methods*, 259:191-203 (2002); Boczkowski, et al., *Cancer Res.*, 60:1028-1034 (2001); and Elango et al., *Biochem. Biophys. Res. Comm.*, 330, 958-966 (2005)), and little in the way of a systematic comparison of DNA and RNA transfection procedures. Most available literature for mRNA transfection is based on methods that involve labor intensive cloning of the gene of interest in special vectors containing a bacteriophage promoter upstream and polyA/T stretch downstream of the cloning site. Not only is cloning time consuming, but recombinant plasmids containing a stretch of poly(AIT) are often unstable in bacterial cells and prone to spontaneous mutations (Kiyama, et al., *Gene*, 150:1963-1969 (1994)). Furthermore, most mRNAs that are generated from d(A/T)n vectors contain a short sequence of heterologous nucleotides following the poly(A) tail. The influence of these heterologous sequences on translation is unknown (Elango et al., *Biochem. Biophys. Res. Comm.*, 330, 958-966 (2005)).

Accordingly, there remains a need for improved methods of making RNA in vitro. There also remains a need for improved methods of cell modification that do not rely on genomic integration of the modifying construct.

It is an object of the present invention to provide a more convenient and/or efficient method of mRNA production for transfection of different types of cells, including cells which are not transfectable for DNA.

It is also an object of the present invention to provide a method of mRNA transfection with minimal side effects and high efficiency, which allows transient expression of genes and desirable modification of cell phenotype without causing permanent genetic changes, which avoids risk associated with conventional gene therapy.

It is also an object of the present invention to provide a method of cell transfection with multiple genes wherein the level of each gene expression can be individually controlled.

It is an object of the present invention to provide a method of transfection of primary mammalian cells, including human cells, and use of those cells for therapy of cancer, autoimmune and infectious diseases.

It is an object of the present invention to provide a method of transfection of primary mammalian cells, including human cells, and use of those cells for treatment of a variety of human diseases including neurological diseases, organ regeneration, and restoration of the immune system.

It is another object of the present invention to provide a method of transient cell modification, which allows fast and safe generation of diverse differentiation, de-differentiation, re-differentiation, or reprogramed states of cells of different cell types, including diverse stem cells from various tissues such as fibroblasts, hematopoietic, epithelial cells and others.

It is another object of the invention to provide modified cells and methods of use thereof in various therapeutic strategies to treat a wide range of cancers and other diseases and disorders.

It is a further object of the invention to provided transfected cells that exhibit (1) CAR reprogramming, (2) improved survival and metabolic stability, (3) ability to distinguish tumor from normal cells, (4) ability to avoid immunosuppression, and combinations thereof.

SUMMARY OF THE INVENTION

Compositions and methods of making cells using RNA, and cells made using the disclosed compositions and methods are also provided. In exemplary embodiments, RNA is transfected into cells to effect a molecular, biological, physiological, or histological change in the cells. In preferred embodiments, the RNA is prepared in vitro, more preferably using a DNA template according to the compositions and methods discussed in more detail below. The cells can be therapeutic cells that can be administered to a subject need thereof in an effective amount to treat a disease or disorder such as cancer, infection, or autoimmunity.

Methods for treating or inhibiting a disorder or disease such cancer, disease or disorders of the immune system, autoimmune disorders, and diseases and disorders caused by viral, bacterial or fungal infection in a host are also provided. The methods can include, for example, locally or systemically administering to the host an effective amount of one or more RNAs; or an effective amount of population of cells isolated from the subject or a syngeneic or histocompatible subject, contacted ex vivo with one or mRNA, and optionally expanded. The cells can be, for example, immune cells or stem cells.

For example, a therapeutic immune cell, such as T cell or Natural Killer (NK) cell, can include one or more RNAs prepared by in vitro transcription, wherein the one or more RNAs encode one or more polypeptides, and wherein at least one of the polypeptides is a heterologous polypeptide that renders the immune cells specific for a tumor, virus, bacteria or fungal antigen expressed on the surface of the cells of a subject. The one or more RNAs can be prepared by in vitro transcription of a linear double stranded DNA template prepared by polymerase chain reaction (PCR). In some embodiments, the one or more RNAs are prepared by in vitro transcription of a linear double stranded DNA template including an RNA polymerase promoter on the coding strand of the double-stranded DNA, a 5' untranslated region less than 3,000 nucleotides in length and effective for translation of the mRNA into a detectable polypeptide after transfection into a eukaryotic cell, an open reading frame that encodes the polypeptide, wherein the polypeptide is heterologous to the cell to be transfected and wherein the polypeptide is selected from the group consisting of a ligand or a receptor of an immune cell, a polypeptide that stimulates or inhibits a function of the immune system, and a polypeptide that inhibits the function of an oncogenic polypeptide, 3' untranslated region effective for translation of the mRNA into a detectable polypeptide after transfection into a eukaryotic cell, and a poly(A) stretch of 50-5,000 nucleotides on the coding strand of the double-stranded DNA, wherein the promoter is heterologous to the open reading frame, and wherein the DNA template terminates with the 3' end of the poly(A) stretch.

In some embodiments, one or more of the transfected RNAs encodes one or more chimeric antigen receptors (CAR), and the immune cells are transfected with an effective amount the CAR RNA for the encoded CAR polypeptide or polypeptides to be detected on the surface of the immune cell. The CAR can be an anti-CD19 CAR, for example, an anti-CD19 CAR including (i) anti-CD19 single strand antibody domains, a transmembrane domain, a 4-113B domain, and a CD3 zeta domain; or (ii) anti-CD19 single strand antibody domains, a transmembrane domain, and a CD3 zeta domain. In some embodiments, the CAR targets CD33, CD123, or CD276. The cells can be transfected with RNAs encoding two or more CARs. For example, some cells express CARs that target CD33 and CD123.

In some embodiments, the cells are transfected with one or more of the RNAs that encodes a factor or factors that modulate the cell's metabolism. Exemplary factors include those that increase viability or reduce apoptosis, for example, IL-2, IL-7, IL-15, BCL-xL, chimeric interleukin receptors, and combinations thereof.

The cells can be transfected with one or more of the RNAs that render the cell resistant to one or more inhibitory molecules. The RNAs can be, for example, siRNAs and CRISPRi constructs. The inhibitory molecule(s) can be, for example, CTLA-4, PD-1, LAG-3, 2B4 (CD244), BTLA (CD272), KIR, TIM-3, TGF beta receptor dominant negative analog, or a combination thereof.

The cells can be transfected with RNA that encodes one or more inhibitor chimeric antigen receptors (iCAR). In particular embodiments, the iCAR targets CD123 or hepatic asialoglycoprotein receptor.

Methods of using the transfected cells to treat subjects in need thereof, for example subjects with cancer can include administering the subject an effective amount of the therapeutic immune cells to reduce one or more symptoms of a disease or disorder such as cancer. In some embodiments, the subject is co-administered an effective amount of a chemotherapy or a BH3 mimetic to further reduce one or more symptoms of the cancer relative to administering the subject the cells alone.

Methods of de-differentiating, reprogramming, and trans-differentiating somatic cells are also provided. The methods can be used to prepare pluripotent stem-like cells or de-differentiated cells. The methods can include contacting somatic cells with one or more RNAs, wherein the one or more RNAs encode polypeptides that function to reprogram, de-differentiate or trans-differentiate the somatic cells. The somatic cells can be, for example, fibroblasts, adipocytes, hematopoietic cells, epithelial cells, and muscle cells. Once de-differentiated, the cells can be re-differentiated with RNAs.

In particular embodiments a method of de-differentiating, trans-differentiating, or re-programming somatic cells includes transfecting the somatic cells with one or more isolated RNAs. The RNAs can be mRNAs, regulatory RNAs, siRNA miRNA, and combinations thereof. The somatic cells can be transfected with at least two different RNAs. The somatic cells can be, for example, unipotent, multipotent, pluripotent, and differentiated cells. The one or more RNAs can induce de-differentiation of the somatic cells to unipotent, multipotent, or pluripotent cells. The RNAs can be, for example, OCT4, SOX2, NANOG, LIN28, KLF4 and MYC mRNA. In exemplary embodiments, OCT4, SOX2, NANOG, and LIN28 mRNA are administered in combination, or OCT4, SOX2, KLF4 and MYC mRNA are administered in combination. The transfected cells can be maintained in culture as induced pluripotent stem (iPS) cells. The induced pluripotent stem cells can be induced to form differentiated cells. The differentiated cells can be, for example, bone, connective tissue, organ tissue, vascular tissue, skin or nervous tissue.

In some embodiments, the somatic cells are contacted in vivo with one or more isolated RNAs, wherein at least one of the RNAs is an interfering RNA that inhibits expression of an mRNA encoding an allogenic antigen. In some embodiments, the somatic cells are lymphocytes and the RNA is FoxP3 mRNA in an amount effective to re-program the lymphocytes into regulatory T cells.

Methods for treating or inhibiting one or more symptoms of a disease or disorder in a patient are also provided and can include administering the subject an effective amount of the cells de-differentiated ex vivo. In some embodiments, the disease or disorder is a neurodegenerative disorder. The somatic cells can be isolated from and re-administered to the same subject.

Methods of RNA production for use in transfection are also provided. The methods can involve in vitro transcription of PCR generated templates with specially designed primers, followed by polyA addition, to produce a construct containing 3' and 5' untranslated sequence ("UTR"), a 5' cap and/or Internal Ribosome Entry Site (IRES), the gene to be expressed, and a polyA tail, typically 50-2000 bases in length. This RNA can efficiently transfect different kinds of cells. This approach results in increased efficiency (fidelity and productivity) of mRNA synthesis and is less time consuming because it does not require cloning, and also consequently eliminates the unwanted errors and effects related to RNA made on DNA templates obtained with cloning techniques.

The results of transfection of RNAs obtained using this method demonstrate that RNA transfection can be very effective in cells that are exceedingly difficult to transfect efficiently with DNA constructs. Further, the levels of gene expression following mRNA transfection are consistent from cell to cell in an experiment and these levels can be controlled over a wide range simply by changing the amount of mRNA that is transfected, and without obvious cytotoxic effects due to the levels of RNA per se. Due to high efficiency the cells can be simultaneously transfected with multiple genetic constructs. The method can be used to deliver genes into cells not- or only poorly transfectable for DNA, in vitro and in vivo.

For example, a linear double-stranded DNA template for in vitro transcription of an RNA can include an open reading frame that encodes a therapeutic, prophylactic or diagnostic polypeptide or nucleic acid molecule, an RNA polymerase promoter on the coding strand of the double-stranded DNA 5' of the open reading frame, a 5' untranslated region between 0-3,000 nucleotides in length and a 3' untranslated region of at least 100 nucleotides, and a 3' poly(T) stretch of 50-5,000 nucleotides, wherein the DNA template is not contained within a DNA vector. The RNA polymerase promoter can include a consensus binding sequence for an RNA polymerase selected from the group consisting of T7, T3 or SP6 RNA polymerase. The open reading frame can encode a polypeptide that is heterologous to the cell, for example a fusion polypeptide. The open reading frame can encode a polypeptide that functions as a ligand or receptor for cells of the immune system, stimulates or inhibits the function of the immune system, or inhibits the function of a polypeptide encoded by an oncogene or a viral, bacterial or fungal gene. The linear double-stranded DNA template can also include an internal ribosome entry site.

In more particular embodiments, a linear double stranded DNA template includes an RNA polymerase promoter on the coding strand of the double-stranded DNA, a 5' untranslated region less than 3,000 nucleotides in length and effective for translation of the mRNA into a detectable polypeptide after transfection into a eukaryotic cell, an open reading frame that encodes the polypeptide, wherein the polypeptide is heterologous to the cell to be transfected and wherein the polypeptide is selected from the group consisting of a ligand or a receptor of an immune cell, a polypeptide that stimulates or inhibits a function of the immune system, and a polypeptide that inhibits the function of an oncogenic polypeptide, 3' untranslated region effective for translation of the mRNA into a detectable polypeptide after transfection into a eukaryotic cell, and a poly(A) stretch of 50-5,000 nucleotides on the coding strand of the double-stranded DNA, wherein the promoter is heterologous to the open reading frame, and wherein the DNA template terminates with the 3' end of the poly(A) stretch.

Methods of generating a linear double-stranded DNA template for in vitro transcription of an RNA are also provided and can include generating forward and reverse primers wherein the forward primer includes a plurality of nucleotides that are substantially complementary to the non-coding strand of a target double-stranded DNA of interest, and a plurality of nucleotides that function as a binding site for an RNA polymerase, wherein the reverse primer includes a plurality of nucleotides that are substantially complementary to the coding strand of a target double-stranded DNA of interest and a plurality of deoxythymidine nucleotides, and performing polymerase chain reaction amplification of the target DNA using the forward and reverse primers.

In some embodiments, the method of generating a linear double-stranded DNA template for in vitro transcription of an RNA includes generating forward and reverse primers wherein the forward primer include a plurality of nucleotides that are substantially complementary to a region of nucleotides directly upstream of a target double-stranded DNA of interest, wherein the reverse primer includes a plurality of nucleotides that are substantially complementary to a region of nucleotides directly downstream of a target double-stranded DNA of interest, performing polymerase chain reaction amplification of the target DNA using the forward and reverse primers, and enzymatically or chemically ligating to the polymerase chain reaction product the 3' poly(T) stretch and the RNA polymerase promoter.

The primers can include nucleotide sequences that are substantially complementary to stretches of nucleotides in the 5' and 3' untranslated regions of a double-stranded DNA of interest. The primers can include nucleotide sequences that are substantially complementary to stretches of nucleotides within the open reading frame of a double-stranded DNA of interest. The primers can include nucleotide sequences that are substantially complementary to stretches of nucleotides within the open reading frame of a double-stranded DNA of interest, wherein the primers further includes stretches of nucleotides that includes 5' and 3' untranslated regions, wherein the stretch of nucleotides in the forward primer that compose the 5' untranslated region is between the nucleotides that compose the RNA polymerase promoter and the nucleotides that are substantially complementary to the non-coding strand of a target double-stranded DNA of interest, and wherein the stretch of nucleotides in the reverse primer that compose the 3' untranslated region is between the plurality of deoxythymidine nucleotides and the nucleotides that are substantially complementary to the coding strand of a target double-stranded DNA of interest. In some embodiments, the forward primer and open reading frame includes a consensus Kozak sequence.

RNA for transfection of cells can be prepared by performing in vitro transcription from a linear double-stranded DNA template. A poly(A) polymerase can be used to extend the poly(A) tail of the RNA with one or more adenine nucleotides or analogs thereof. Nucleotides can be added during transcription that function as a 5' cap for the transcribed RNA. Isolated RNA produced according to the disclosed methods is also provided.

Methods for expressing one or more RNAs in a cell are disclosed. The methods can include contacting cells with one or more RNAs. In some embodiments, the RNAs are present in unequal molar amounts to provide separate expression levels of the RNAs in the cells. Methods for generating an autologous population of immune cells are provided and can include contacting the cells with one or more RNAs. The one or more RNAs can encode polypeptides that render the immune cells specific for tumor, virus, bacteria or fungal antigens expressed on the surface of the cells of a host.

Kits are also provided. In some embodiments, the kit includes an effective amount of vector-free nucleic acids encoding at least one heterologous polypeptide to render a population of immune cells specific for a tumor, virus, bacteria or fungal antigen expressed on the surface of the cells of a subject.

BRIEF DESCRIPTION OF THE DRAWINGS

After completion of transcription polyA tail can be additionally extended with poly(A) polymerase.

FIGS. 6A-6D are a series of histograms showing FACS analysis of transfectants demonstrating various levels of anti-CD19-CAR expression. Cells were mock transfected (FIG. 6A) or transfected with anti-CD19-CAR mRNA at 13.3 μg/ml (FIG. 6B), 40 μg/ml (FIG. 6C), or 120 μg/ml (FIG. 6D). FIGS. 6E-6G are line graphs showing cytotoxicity of CD8+ T lymphocytes (CTLs) transfected with various amounts of anti-CD19-CAR mRNA and analyzed for cytotoxicity with different targets at the indicated E:T ratio. T lymphocytes were incubated for 4 hr with different target cells, loaded with $^{51}$Cr: FIG. 6E, autologous cells CD19+B cells; FIG. 6F, allogeneic CD19+B lymphoblasts; FIG. 6G, CD19 negative K562 cells. (-○-)=mock; (-■-)=13.3 μg/ml; (-▲-)=40 μg/ml; (-●-)=120 μg/ml.

FIGS. 8A-8B show cytotoxicity of anti-CD19 CAR in CTLs activated 1 day (FIG. 8A) or 7 days (FIG. 8B) in the presence of CD3-CD28 beads and IL2. FIG. 8C shows cytotoxicity (percent lysis) of delta (4-1BB) anti-CD19 CAR CTLs after 7 days of activation. (-■-)=anti-CD19 CAR; (-♦-)=mock FIGS. 9A-9D are line graphs showing the cytotoxicity of different lymphocyte subpopulations against autologous B cells. The different lymphocytes subpopulations were: $CD8^+$ (FIG. 9A), CD4+ (FIG. 9B) T cells and their (1:1) mix (FIG. 9C), and NK cells (FIG. 9D) transfected with anti-CD19 CAR mRNA. Targets, autologous CD19+ B cells, were loaded with $^{51}$Cr and analyzed for cytotoxicity at the indicated E:T ratio. (-■-)=mock; (-♦-)=anti-CD19 CAR.

FIGS. 10B-10F are line graphs showing the cytotoxicity of CD276 CAR+CTLs against solid tumors: T47D (FIG. 10C) and MCF7 (FIG. 10F) breast cancer cell, HTB82 rhabdomyosarcoma (FIG. 10D), and autologous melanoma (FIG. 10E) which do not express the CD276 antigen, but not control K562 cells (FIG. 10B). CTLs were transfected with CD276 CAR mRNA. Target cells (K562-negative control, and other cells expressing CD276 antigen), were loaded with $^{51}$Cr and analyzed for cytotoxicity at the indicated E:T ratio. (-■-)=CAR; (-♦-)=mock.

DETAILED DESCRIPTION OF THE INVENTION

I. Definitions

Figure 1:
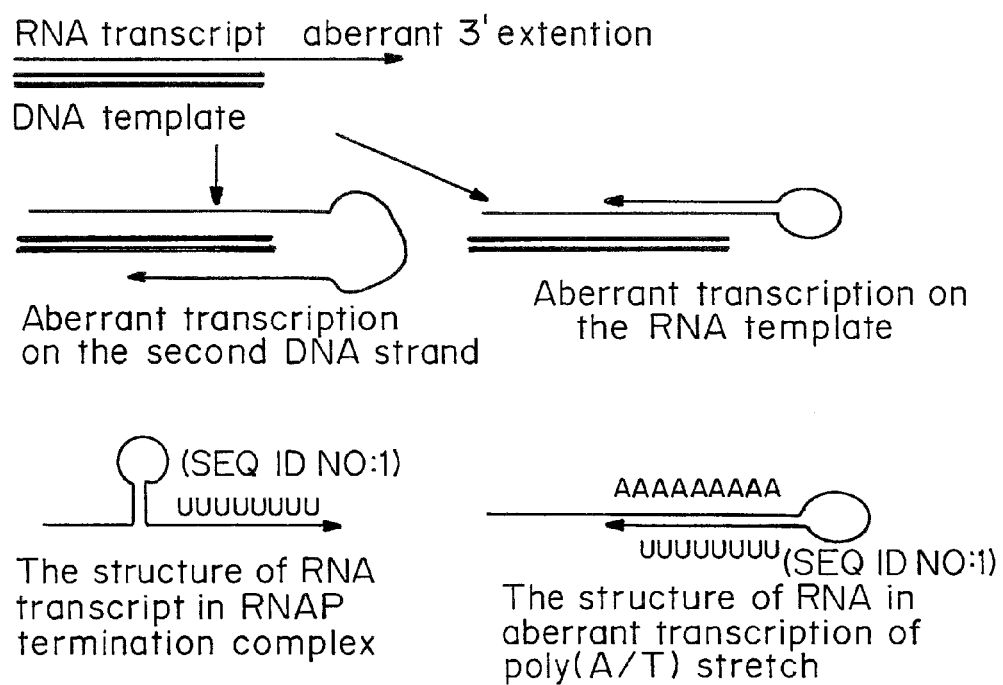
FIG. 1 shows a model of an aberrant T7 RNAP transcription in vitro, which explains why only those DNA templates which contain a polyA/T sequence are suitable for efficient transcription. On a linear DNA template, phage T7 RNA polymerase can extend the 3' end of the transcript beyond the last base of the template. This can lead to runoff transcript bending followed by template exchange with the second DNA strand or transcription of RNA itself, and then to the aberrant transcription in a reverse direction and accumulation of double stranded RNA, which can inhibit gene expression. DNA linearization itself was not sufficient for correct transcription (Triana-Alonso et al., 1995; Dunn and Studier 1983; Arnaud-Barbe et al., 1998; Macdonald et al., 1993; Nakano et al., 1999). It was hypothesized that the presence of a polyT stretch at the 3' end of the DNA template during runoff transcription creates a terminator-like hairpin which can dissociate the RNA polymerase from the template.

The brief life of an mRNA molecule begins with transcription and ultimately ends in degradation. During its life, an mRNA molecule may be processed, edited, and transported prior to translation. During transcription, RNA polymerase makes a copy of a gene from the DNA to mRNA as needed. Eukaryotic RNA polymerase associates with mRNA processing enzymes during transcription so that processing can proceed quickly after the start of transcription. The short-lived, unprocessed or partially processed, product is termed pre-mRNA; once completely processed, it is termed mature mRNA. Eukaryotic pre-mRNA, however, requires extensive processing.

As used herein, a 5' cap (also termed an RNA cap, an RNA 7-methylguanosine cap or an RNA m$^7$G cap) is a modified guanine nucleotide that has been added to the "front" or 5' end of a eukaryotic messenger RNA shortly after the start of transcription. The 5' cap consists of a terminal group which is linked to the first transcribed nucleotide. Its presence is critical for recognition by the ribosome and protection from RNases. Cap addition is coupled to transcription, and occurs co-transcriptionally, such that each influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

As used herein, "polyadenylation" refers to the covalent linkage of a polyadenylyl moiety, or its modified variant, to a messenger RNA molecule. In eukaryotic organisms, most messenger RNA (mRNA) molecules are polyadenylated at the 3' end. The 3' poly(A) tail is a long sequence of adenine nucleotides (often several hundred) added to the pre-mRNA through the action of an enzyme, polyadenylate polymerase. In higher eukaryotes, the poly(A) tail is added onto transcripts that contain a specific sequence, the polyadenylation signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but additionally can also occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

Eukaryotic mRNA that has been processed and transported to the cytoplasm (i.e. mature mRNA) can then be translated by the ribosome. Translation may occur at ribosomes free-floating in the cytoplasm, or directed to the endoplasmic reticulum. After a certain amount of time, the message is degraded by RNases into its component nucleotides. The limited longevity of mRNA enables a cell to alter protein synthesis rapidly in response to its changing needs.

Different mRNAs within the same cell have distinct lifetimes. In bacterial cells, individual mRNAs can survive from seconds to more than an hour; in mammalian cells, mRNA lifetimes range from several minutes to days. The greater the stability of an mRNA, the more protein may be produced from that transcript. The presence of AU-rich motifs in some mammalian mRNAs tends to destabilize those transcripts through the action of cellular proteins that bind these motifs. Rapid mRNA degradation via AU-rich motifs is a critical mechanism for preventing the overproduction of potent cytokines such as tumor necrosis factor (TNF) and granulocyte-macrophage colony stimulating factor (GM-CSF). Base pairing with a small interfering RNA (siRNA) or microRNA (miRNA) can also accelerate mRNA degradation.

As used herein, "transient" refers to expression of a non-integrated transgene for a period of hours, days or weeks, wherein the period of time of expression is less than the period of time for expression of the gene if integrated into the genome or contained within a stable plasmid replicon in the host cell.

As used herein, a "promoter site" is a sequence of nucleotides to which an RNA polymerase, such as the DNA-dependent RNA polymerase originally isolated from bacteriophage, described by Davanloo, et al., *Proc. Natl. Acad. Sci. USA*, 81:2035-39 (1984), or from another source, binds with high specificity, as described by Chamberlin, et al., *Nature*, 228:227-231 (1970).

As used herein, a poly(A) is a series of adenosines attached by polyadenylation to the mRNA. In the preferred embodiment of a construct for transient expression, the polyA is between 50 and 5000, preferably greater than 64, more preferably greater than 100, most preferably greater than 300 or 400. poly(A) sequences can be modified chemically or enzymatically to modulate mRNA functionality such as localization, stability or efficiency of translation.

As used herein, an "open reading frame" or "ORF" is a series of nucleotides that contains a sequence of bases that could potentially encode a polypeptide or protein. An open reading frame is located between the start-code sequence (initiation codon or start codon) and the stop-codon sequence (termination codon).

II. Methods of Making mRNA for Use in Transient Transfection

RNA for transient transfection is produced by in vitro transcription using a polymerase chain reaction (PCR)-generated template.

A. Sources of DNA for PCR

DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA.

In one embodiment, the DNA to be used for PCR contains an open reading frame. The DNA can be from a naturally occurring DNA sequence from the genome of an organism. In one embodiment, the DNA is a full length gene of interest of a portion of a gene. The gene can include some or all of the 5' and/or 3' untranslated regions (UTRs). The gene can include exons and introns. In one embodiment, the DNA to be used for PCR is a human gene. In another embodiment, the DNA to be used for PCR is a human gene including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

Genes that can be used as sources of DNA for PCR include genes that encode polypeptides that provide a therapeutic or prophylactic effect to an organism or that can be used to diagnose a disease or disorder in an organism. Preferred genes are genes which are useful for a short term treatment, or where there are safety concerns regarding dosage or the expressed gene. For example, for treatment of cancer, autoimmune disorders, parasitic, viral, bacterial, fungal or other infections, the transgene(s) to be expressed may encode a polypeptide that functions as a ligand or receptor for cells of the immune system, or can function to stimulate or inhibit the immune system of an organism. It is not desirable to have prolonged ongoing stimulation of the immune system, nor necessary to produce changes which last after successful treatment, since this may then elicit a new problem. For treatment of an autoimmune disorder, it may be desirable to inhibit or suppress the immune system during a flare-up, but not long term, which could result in the patient becoming overly sensitive to an infection.

Genes that can be used as sources of DNA for PCR include genes that encode peptides that are important for regulating cellular differentiation. Preferred genes include transcription factors and mRNA-binding proteins, for example, transcription factors that regulate the self-renewal and/or proliferation of stein cells. In some embodiments, the DNA encodes inhibitory RNAs, such as small interfering RNA (siRNA) or micro RNA (miRNA). For example, the DNA may encode an interfering RNA that prevents expression of an mRNA encoding an allogenic antigen. The DNA may encode an RNA that is a pre-RNA, for example pre-miRNA, or a mature RNA, for example mature miRNA. The DNA may encode an RNA that is a fragment or variant of an RNA that retains the biological activity of the RNA.

B. PCR to Produce Templates for in vitro Transcription

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. "Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5' to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Any DNA polymerase useful for PCR can be used in the methods disclosed herein. The reagents and polymerase are commercially available from a number of sources.

1. Untranslated Regions

Chemical structures with the ability to promote stability and/or translation efficiency may also be used. The RNA preferably has 5' and 3' UTRs. Inclusion of 44 base pairs of 5' UTR into the PCR template enables greater translation efficiency of transcribed RNA, for example green fluorescent protein (GFP), when compared to PCR templates containing only 6 base pairs of 5' UTR. The addition of 113 base pairs of 3' UTR enables greater translation efficiency of transcribed GFP RNA when compared to PCR templates containing only 11 base pairs of 3' UTR. In general, the length of the 3' UTR exceeds 100 nucleotides, and therefore 3' UTR longer than 100 nucleotides is preferred. For example, the 3' UTR sequence is between 100 and 5000 nucleotides. The length of the 5' UTR is not as critical as the length of the 3' UTR and can be shorter. For example, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences increase the efficiency of translation of some RNA transcripts, but do not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

2. RNA Polymerase Promoter

To enable synthesis of RNA from a DNA template without the need for gene cloning, a promoter of transcription should be attached to the DNA template upstream of the sequence to be transcribed. Bacteriophage RNA polymerase promoter sequences can be attached to the 5' UTR by different genetic engineering methods, such as DNA ligation, or can be added to the forward primer (5') of the sequence that is substantially complementary to the target DNA. When a sequence that functions as a promoter for an RNA polymerase is added to 5' end of the forward primer, the RNA polymerase promoter becomes incorporated into the PCR product upstream of the open reading frame that is to be transcribed. In one preferred embodiment, the promoter is a T7 polymerase promoter. Other useful promoters include, but are not limited to, T3 and SP6 RNA polymerase promoters. Consensus nucleotide sequences for T7, T3 and SP6 promoters are known in the art.

3. Poly(A) Tail and 5' Cap

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

Figure 2A:
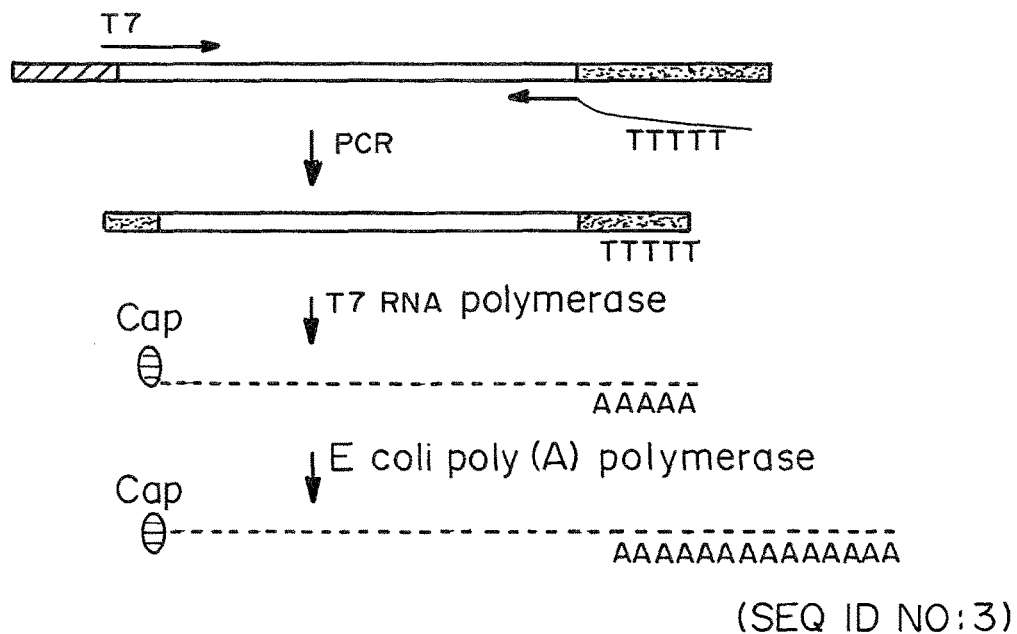
FIG. 2A is a scheme for mRNA synthesis using a DNA template obtained by PCR with use of specially designed primers. The forward primer contains a bacteriophage promoter suitable for in vitro transcription and the reverse primer contains a polyT stretch. The PCR product is an expression cassette suitable for in vitro transcription. Polyadenylates on the 3' end of the nascent mRNA can prevent aberrant RNA runoff synthesis and creation of double strand RNA product.

On a linear DNA template, phage T7 RNA polymerase can extend the 3' end of the transcript beyond the last base of the template (Schenborn and Mierendorf, *Nuc Acids Res.*, 13:6223-36 (1985); Nacheva and Berzal-Herranz, *Eur. J. Biochem.*, 270:1485-65 (2003). This could lead to runoff transcript bending followed by template exchange with the second DNA strand or transcription of RNA itself (Triana-Alonso et al., *J. Biol. Chem.*, 270:6298-307 (1995); Dunn and Studier, *J. Mol. Biol.*, 166:477-535 (1983); Arnaud-Barbe, et al., *Nuc. Acids Res.*, 26:3550-54 (1998); Macdonald et al., 1993), and then to the aberrant transcription in a reverse direction and accumulation of double stranded RNA, which can inhibit gene expression. DNA linearization itself is not sufficient for correct transcription (Triana-Alonso et al., *J. Biol. Chem.*, 270:6298-307 (1995); Dunn and Studier, *J. Mol. Biol.*, 166:477-535 (1983); Arnaud-Garbe et al., 1998 *Nuc. Acids Res.*, 26:3550-54 (1998); Macdonald et al., *J. Mol. Biol.*, 232:1030-47 (1993); Nakano et al., *Biotechnol. Bioeng.*, 64:194-99 (1999). plasmid DNA linearized downstream of a poly(A/T) stretch of 64-100 nucleotides results in good templates (Saeboe-Larssen et al., *J. Immunol. Meth.*, 259:191-203 (2002); Boczkowski et al., *Cancer Res.*, 60:1028-34 (2000); Elango et al., *Biochem Biophys Res Commun.*, 330:958-966 2005). An endogenous termination signal for T7 RNA polymerase encodes an RNA that can fold into a stem-loop structure followed by a track of uridine residues (Dunn and Studier, *J. Mol. Biol.*, 166:477-535 (1983); Arnaud-Barbe et al., 1998 *Nuc. Acids Res.*, 26:3550-54 (1998)). Even without a hairpin, a track of synthesized uridines can attenuate transcription (Kiyama and Oishi, *Nucleic Acids Res.*, 24:4577-4583 (1996). It was hypothesized that the linearization of plasmid DNA downstream of the poly(A/T) stretch probably formed a type of "dynamic" terminator preventing potential aberrant transcription: a 3' extension of the RNA transcript over a poly(A/T) stretch and transcription in the reverse direction will create a growing termination-like signal—an extended poly(U) stretch and a poly(A/U) hairpin (FIG. 1). Based on this presumption, reversed PCR primers can be designed with a 3' anchoring sequence downstream of the GFP gene and a 5' 100 base stretch of poly(T) (FIG. 2A).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, typically 50-5000T, for example a 100T tail, or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines. The examples below demonstrate that a 100 base pair stretch of poly(A) is sufficient to enable efficient translation of an RNA transcript.

Figure 2B:
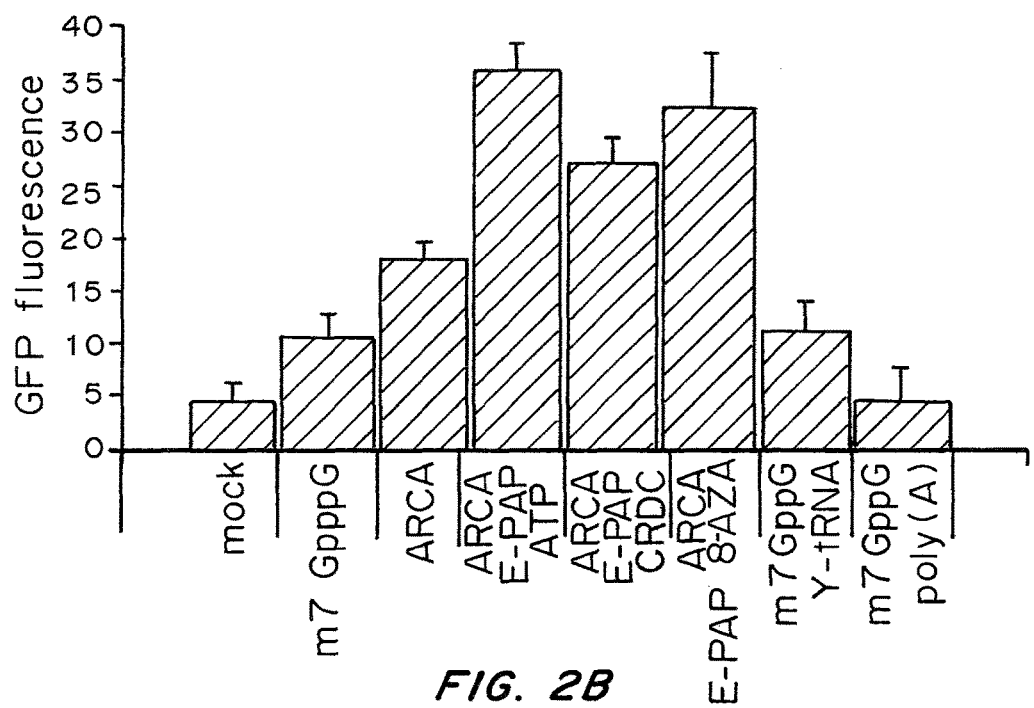
FIG. 2B shows the efficiency of mRNA transfection depending on its structure. EML cells were transfected with 60 µg/ml GFP mRNAs made with a standard cap analog dinucleotide or cap analog, 3'-O-Methyl-m7G[5']ppp[5']G (ARCA). Certain transcripts were treated with E. coli Poly(A) polymerase in the presence of ATP, ATP analogs: cordycepin (CDCP) or 8-aza-adenosine (8-AZA). Certain transfections were performed in the presence of 1 mg/ml polyadenylate RNA or yeast tRNA. GFP expression was analyzed by FACS. The expression efficiency was calculated as the geometric mean of fluorescence intensity (±SD; n=3) as reported by the FACS instrument. Capping as well polyadenylation increased GFP expression. Incorporation of ATP analogs in the 3' end of the mRNA also increased expression, probably by protecting the 3' end from RNAse.

Poly(A) tails of RNAs can be further extended following in vitro transcription with the use of a poly(A) polymerase, such as *E. coli* polyA polymerase (E-PAP). The examples below demonstrate that increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA. Suitable ATP analogs include, but are not limited to, cordiocipin and 8-azaadenosine (FIG. 2B).

5' caps can also provide stability to RNA molecules. In a preferred embodiment, RNAs include a 5' cap. The 5' cap may, for example, be $m^7G(5')ppp(5')G$, $m^7G(5')ppp(5')A$, $G(5')ppp(5')G$ or $G(5')ppp(5')A$ cap analogs, which are all commercially available. The 5' cap can also be an anti-reverse-cap-analog (ARCA) (FIG. 2 B and also Stepinski, et al., *RNA*, 7:1468-95 (2001)) or any other suitable analog. The 5' cap is provided using techniques known in the art and described herein (Cougot, et al., *Trends in Biochem. Sci.*, 29:436-444 (2001); Stepinski, et al., *RNA*, 7:1468-95 (2001); Elango, et al., *Biochim. Biophys. Res. Commun.*, 330:958-966 (2005)).

The RNAs produced by the methods disclosed herein can also contain an internal ribosome entry site (XRES) sequence. The TRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

In some embodiments, the RNA can include modified or artificial nucleotides, or nucleotide analogs or derivatives. Such nucleotides can, for example, reduce degradation of the RNA, minimize toxicity of the RNA for sensitive cells, etc. The most common RNA analogues are 2'-O-methyl-substituted RNA, locked nucleic acid (LNA) or BNA (Bridged Nucleic Acid), morpholino, and peptide nucleic acid (PNA).

III. Methods of Making Reprogrammed and Dedifferentiated Cells

RNA, for example RNA prepared by in vitro transcription using a polymerase chain reaction (PCR)-generated template as described above, can be introduced into a cell to modulate cell activity. This method is particularly useful in de-differentiating somatic cells to unipotent, pluripotent or multipotent cells; re-differentiating stem cells into differentiated cells, or reprogramming of somatic cells to modulate cell activities such as metabolism. Cells can also be transfected with inhibitory RNAs, such as small interfering RNA (siRNA) or micro RNA (miRNA), or combinations thereof to induce reprogramming of somatic cells, for example, by preventing expression of allogenic antigens.

A. Introduction of RNA into Target Cells

RNA can be introduced into target cells using different methods, for instance, commercially available methods which include, but are not limited to, electroporation (Maxcyte System (Maxcyte, Inc.), Amaxa Nucleofector-II (Amaxa Biosystems, Cologne, Germany), ECM 830 (Harvard Instruments, Boston, Mass.) or the Gene Pulser II (BioRad, Denver, Colo.), Multiporator (Eppendorf, Hamburg Germany), cationic liposome mediated transfection (TransIT, MirusBio LLC, Lipofectin, Invitrigen), polymer encapsulation, peptide mediated transfection, or biolistic particle delivery systems such as "gene guns" (see, for example, Nishikawa, et al. *Hum Gene Ther.,* 12(8):861-70 (2001).

B. Applications

The methods and reagents have a wide range of applications in therapy and research. The methods are useful for expressing one or multiple RNAs in different cell populations such as fully differentiated cells, partially differentiated cells, multipotent cells, and non-differentiated cells, such as pluripotent cells.

The RNA construct can be delivered into different types of eukaryotic cells as well as into tissues and whole organisms using transfected cells as carriers or cell-free local or systemic delivery of encapsulated, bound or naked RNA. The methods can be used for any purpose where a transient expression is required or sufficient. The methods can be applied to modulation of cell activity in basic research and therapy, in the fields of cancer, stem cells, acute and chronic infections, genetic disorders, neurological disorders, and autoimmune diseases, including modulation of the developmental pathways. Thus, cells containing an RNA construct introduced according to the disclosed methods can be used therapeutically.

1. Cells

Cells suitable for use with the method include, but are not limited to, primary cells and established cell lines, embryonic cells, immune cells, stem cells, and differentiated cells including, but not limited to, cells derived from ectoderm, endoderm, and mesoderm, including fibroblasts, parenchymal cells, hematopoietic cells, and epithelial cells. As used herein, stem cells include unipotent cells, multipotent cells, and pluripotent cells; embryonic stem cells, and adult stem cells such as hematopoietic stem cells, mesenchymal stem cells, epithelial stem cells, and muscle satellite cells.

In some embodiments, somatic cells are de-differentiated, reprogrammed, or a combination thereof. Any suitable somatic cell can be used. Representative somatic cells include fibroblasts, keratinocytes, adipocytes, muscle cells, organ and tissue cells, and various blood cells including, but not limited to, hematopoietic cells including hematopoietic stem cells, and cells that provide short- or long-term hematopoietic engraftment. Preferred cell types include, but are not limited to, human fibroblasts, keratinocytes, hematopoietic stem cells, and immune cells including, but not limited to, T lymphocytes, Natural Killer cells, dendritic cells, antigen presenting cells, B cells, and macrophages. The methods are particularly useful for reprogramming, trans-differentiating, de-differentiating and optionally re-differentiating cells, without permanent alteration of cell genomes.

Other sources and cells include, but are not limited to, peripheral lymphocytes, fibroblasts, keratinocytes primary cell lines, or cells harvested directly from the patient or an allographic donor. In preferred embodiments, the target cells to be administered to a subject will be autologous, e.g. derived from the subject, or syngenic. Allogeneic cells can also be isolated from antigenically matched, genetically unrelated donors (identified through a national registry), or by using target cells obtained or derived from a genetically related sibling or parent.

2. RNAs

RNAs useful in the disclosed method include mRNAs, regulatory RNAs, or small RNAs such as siRNA or miRNA wherein the one or more mRNAs encode polypeptides that function to de-differentiate or reprogram the cell. The efficiency of transfection is high. Typically more than 90% of the transfected cell population will express the introduced RNA. Therefore, it is possible to transfect cells with one or more distinct RNAs. For example, it is possible to generate an autologous lymphocyte population with multiple sets of receptors to recognize and destroy targets which otherwise escape cytotoxic T lymphocyte (CTL) surveillance or to increase the specificity of the CTL towards selected targets. Similar procedures could be used with NK or NKT cells or other types of immune effector cells to target them to specific cells or tissues or increase their avidity for specific cells or tissues. The method can also be used to introduce various mRNAs and/or siRNAs that render the T cell resistant to inhibitory molecules in vivo. Also, mRNAs that encode transcription factors and/or effector proteins characteristic of $CD8^+$ cytotoxic T cells can be introduced into a mixed population of T lymphocytes in order to convert them all to a cytotoxic T cell phenotype.

RNAs can be delivered in a single administration, or multiple administrations which can be staggered minutes, hours, days, or weeks apart. Transfection of multiple distinct RNAs may be staggered. For example, if it is desirable for a first RNA to be expressed prior to expression of one or more additional RNAs.

The level of expression of the transfected RNA can be manipulated over a wide range by changing the amount of input RNA, making it possible to individually regulate the expression level of each transfected RNA. The effective amount of input RNA is determined based on the desired result. Furthermore, the PCR-based technique of mRNA production facilitates the design of mRNAs with different structures and combinations domains. RNAs useful in the disclosed methods are known in the art, and will be selected based on the target host cell type as well as the pathway or cellular activity to be manipulated, or the therapeutic application.

IV. Therapeutic Strategies

In vitro de-differentiation, re-differentiation, and/or reprogramming can be applied to a variety of different starting cell types and allows fast and safe generation of cells over a diverse range of de-differentiated, re-differentiated, and reprogrammed states. As used herein, in vitro de-differentiation, re-differentiation, and reprogramming includes de-differentiation, re-differentiation, and reprogramming of isolated cells ex vivo. In some embodiments, the technology is used for personalized therapy. Target cells can be first isolated from a donor using methods known in the art, contacted with one or more RNA's causing the cells to be de-differentiated, re-differentiated, or reprogrammed in vitro (ex vivo), and administered to a patient in need thereof.

For example, for treatment of tumors, the patient's blood or cells can be collected by an appropriate method such as apheresis, biopsy or venapuncture. The cells can be cultured for at least 24 hours during which time the cells are transfected with an appropriate construct (e.g., to treat the tumor). In particular embodiments, a lymphocyte cell population is withdrawn from a patient, transfected with different RNA constructs, and then reintroduced into the patient. The transfected cell population would then target lymphoma or other cancer cells, which contain the CD19 or other target antigen. The cells can be stored frozen before transfection, if necessary.

Cells can optionally be sorted, cloned, or otherwise separated to collect a heterogeneous or homogenous subpopulation. Cells can be selected by positive and/or negative selection techniques. For example, antibodies binding a particular cell surface protein may be conjugated to magnetic beads and immunogenic procedures utilized to recover the desired cell type. It may be desirable to enrich the target cells prior to transient transfection. As used herein in the context of compositions enriched for a particular target cell, "enriched" indicates a proportion of a desirable element (e.g. the target cell) which is higher than that found in the natural source of the cells. A composition of cells may be enriched over a natural source of the cells by at least one order of magnitude, preferably two or three orders, and more preferably 10, 100, 200 or 1000 orders of magnitude. Once target cells have been isolated, they may be propagated by growing in suitable medium according to established methods known in the art. Established cell lines can also be used in for the disclosed methods. The cells can be stored frozen before transfection, if necessary. These cells can then returned and administered back to the patient.

Next the cells can be contacted with one or more RNAs in vitro, for example using a transfection technique known in the art. De-differentiation, re-differentiation, and/or re-programming can be monitored, and the desired cell type can be selected for therapeutic administration.

Following de-differentiation, and/or re-differentiation and/or reprogramming, the cells can be administered to a patient in need thereof. In the most preferred embodiments, the cells are isolated from and administered back to the same patient. In alternative embodiments, the cells are isolated from one patient, and administered to a second patient. The method can also be used to produce frozen stocks of RNA-reprogrammed or dedifferentiated cells stored long-term, for later use. As discussed in more detail below, in some embodiments, fibroblasts, keratinocytes, hematopoletic stem cells, or lymphocytes are isolated from a patient and de-differentiated and/or re-differentiated and/or reprogrammed in vitro to provide iPS cells, or CAR T or NK cells for the patient.

A unique trait of mRNA-based methods is the ability to introduce in each cell, in a single step, multiple mRNAs with an efficiency that is not possible via DNA transfer.

Cells, such as T cells, can be successfully electroporated with different combinations of mRNAs encoding CD19 CAR, CD276 CAR, BCL-2, BCL-XL, and IL-2 proteins, etc., without any detrimental effect over a wide range of mRNA concentrations up to 600 ug/ml. For example, using 30 ug/ml for each mRNA allows 20 RNAs in a single electroporation.

As discussed in the examples below, gene expression of each transgene is typically proportional to the amount of its mRNA during electroporation, and independent of the presence of other transgenes in the range of 0-300 µg/ml total mRNA. Routinely, electroporation of cells with 30 µg/ml mRNA generated a sufficient level of CAR directed cytotoxicity for at least 4 days after transfection (Rabinovich, et al., *Human Gene Therapy,* 17:1027-1035 (2006)). mRNA electroporation (Amaxa) leads to a relatively rapid onset (4-8 hr) of highly uniform expression of multiple mRNAs with ~40-55% viability and ~90% efficiency. In order to preserve the polyclonal repertoire of the lymphocytes, the full protocol can be completed within two days, with isolation and activation on the first day and electroporation on the second.

An illustrative result is provided in Example 4 below, and FIGS. 6A-6D. Human CD8+ T cells were electroporated with 0 (mock), 13.3, 40 or 120 µg/ml CD19 CAR mRNA. Although the CAR expression varies by FACS detection (FIG. 6A), cytotoxicity is equivalent for autologous or allogeneic B cells (FIG. 6B-6D). Mock transfected or CD19 negative cells show no cytotoxicity. These findings indicate that increased killing might not be achieved by increased expression alone, in this dose range. An alternative tact, therefore, may be the simultaneous use of multiple CARs.

Additionally, as discussed in more detail below, the methods can include simultaneous expression of multiple beneficial proteins in a single cell. As illustrated in the Examples below, in some embodiments, transfection of multiple mRNA can be carried out in a single step with up to ~90% efficiency (Rabinovich, et al., *Human Gene Therapy,* 20:51-61 (2009); Rabinovich, et al., *Human Gene Therapy,* 17:1027-1035 (2006). Although discussed in detail below in the context of immunology and dedifferentiation strategies, all of disclosed compositions and methods are also explicitly disclosed for use in other cell types and treatment strategies. For example, methods can also be used to reprogram somatic cells wherein RNAs are introduced into cells in order to modulate their viability. In an exemplary embodiment, mRNA coding dominant-negative mutant p53 protein can temporarily block p53 function. This mRNA can be introduced into cells to protect them from p53-mediated apoptosis caused by metabolic disturbances during de-differentiation.

A. Immunomodulation

Many of the advantages of the disclosed RNA-based methods make them particular suitable in the field of immunomodulation. Genetic transduction of different types of cytotoxic lymphocytes to express desired receptors for adoptive immunotherapy is a valuable method to redirect the specificity of lymphocytes for tumor antigens, which are not readily recognized by the endogenous $\alpha\beta$ T-cell or NK receptors.

However, a potential disadvantage of such DNA-based methods is genome integration of transgenes as well as the technical complexity of the method. In addition, DNA transfer protocols require an extensive ex vivo expansion step of patient derived T cells over several weeks, by establishing permanent, proliferating, CAR-T cell clones which often generates predominantly T effector cells with limited proliferative potential (Hinrichs, et al., *Immunological Reviews,* 257:56-71 (2014)). It takes weeks or months to clone and accumulate a desirable homogeneous specific lymphocyte population suitable for the treatment. Another problem of cloning is that lymphocyte diversity, an important factor which determines immune response, is an unavoidable complication of such procedure. Cytotoxic lymphocytes propagated ex vivo are presented as heterogeneous subpopulations, including for example, CD3+ T cells, CD3-NK cells, and also natural killer T (NKT) and cytokine induced killer (CIK) cells with additional sub diversity among each subpopulation. The whole cytotoxic potential can be influenced by cooperation of different cell types.

In contrast to DNA-based protocols, which introduce CARs by retroviral DNA transfer and carry the risk of insertional mutagenesis and oncogene activation (Hacein-Bey-Abina, et al., *The New England Journal of Medicine*, 348:255-256 (2003)), RNA transfection is essentially transient and is free from foreign (vector) sequences: mRNA transgene can be delivered and expressed into the lymphocytes after brief in vitro cell activation, as a minimal expressing cassette without any additional viral sequences. In these conditions genome integration of the transgene is quite improbable. The typically transient nature of the methods allows fine-tuning of the active T cell load with adjustable levels of mRNA expression, and therapy can be include repeat cell transfusions over the course of treatment. A benefit of the use of mRNA transfected cells is that mRNA transgene has a limited half-life. The encoded protein will only be produced by the transfected cell for a limited period of time. This may reduce unintended consequences when genetically modified cells are reintroduced into a patient. As a result, the methods avoid complications of an uncontrolled expansion and permanent, circulating chimeric T cells, including massive killing of target cells followed by a cytokine storm (Kalos, et al., *Science Translational Medicine*, 3:95ra73 (2011)), depletion of normal CD19+ B cells, and the need for gamma-globulin replacement (Porter, et al., *The New England Journal of Medicine*, 365:725-733 (2011), and/or to detrimental, off-target cytotoxicity.

Cell cloning is unnecessary because of the efficiency of mRNA transfection and its ability to uniformly modify the entire lymphocyte population. The RNA-based methods can rely on T cell expansion of at least one order of magnitude less than DNA-based methods and are not dependent on T cell clonal efficiency or their proliferative potency, which can be important for autologous therapy of patients with impaired immune systems. For example, two or more different types of lymphocytes such as CD3+CD8+, CD3+ CD4+ T cells, natural killer T cells (NKT), cytokine induced killer cells (CIK), CD56+ and CD16+ NK cells, can be simultaneously transfected with CAR mRNA and used together to increase their potential synergistic effect. CD16 NK, NKT and CIK (or NKT class II) of different origin/marker expression can be useful as well. The lymphocytes can be a heterogeneous population, heterogeneous subpopulation, or homogenous population. Preferred lymphocytes include those discussed above, and others, though CD8+ and CD4+ T cells, and NK cells are the most preferred.

In preferred embodiments, the cells are transfected with two or more different RNAs. Also referred to multifactor or multifactor transfection, two or more RNAs can be used to induce or introduce two more related or unrelated modifications in the transfected cell. For example, as discussed in more detail below, preferred modifications include (1) CAR reprogramming, (2) improved survival and metabolic stability, (3) ability to distinguish tumor from normal cells, (4) ability to avoid immunosuppression. In some embodiments, cells are transfected with one or more RNAs that modulate (1), (2), (3), or (4) individually, or co-transfected with multiple factors to modulate any combination of two, three, or all four of (1), (2), (3), or (4). For example, in some embodiments, cells are co-transfected with a CAR and one or more additional constructs that (1) CAR cell survival and metabolic stability, (2) ability to distinguish tumor from normal cells, (3) ability to avoid immunosuppression, and combinations thereof. Each of these modifications is discussed in more detail below.

1. Chimeric Antigen Receptors a. Chimeric Antigen Receptor

The disclosed compositions and methods are particularly useful in the context of preparing lymphocytes expressing immune receptors, particularly chimeric immune receptor (CIR) such as chimeric antigen receptors (CAR). Artificial immune receptors (also known and referred to herein, as chimeric T cell receptors, chimeric immunoreceptors, chimeric antigen receptors (CARs), and chimeric immune receptors (CIR)) are engineered receptors, which graft a selected specificity onto a cell. Cells modified according to the discussed methods can be utilized, as discussed in more detail below, in a variety of immune therapies for treatment of cancers, infections, inflammation, and autoimmune diseases. In particularly preferred embodiments, immune cells, such as lymphocytes, are transiently transfected with mRNA encoding a chimeric antigen receptor. Strategies for the design and development of chimeric antigen receptors are reviewed in Dotti, et al., *Immunol Rev.* 2014 January; 257(1):. doi:10.1111/imr.12131 (35 pages), which is a specifically incorporated by reference herein in its entirety, as well as Dotti, *Molecular Therapy*, 22(5):899-890 (2014), Karlsson, et al., *Cancer Gene Therapy*, 20:386-93 (2013), Charo, et al., *Cancer Res.*, 65(5):2001-8 (2005), Jensen, et al., *Immunol Rev.*, 257(1): 127-144 (2014), Eaton, et al., *Gene Therapy*, 9:527-35 (2002), Barrett, et al., *Annu Rev Med.*, 65: 333-347 (2014), Cartellieri, et al., *Journal of Biomedicine and Biotechnology*, Volume 2010, Article ID 956304, 13 pages doi:10.1155/2010/956304; and U.S. Published Application Nos. 2015/0017120, 2015/0283178, 2015/0290244, 2014/0050709, and 2013/0071414.

CARs combine the antigen-binding property of monoclonal antibodies with the lytic capacity and self-renewal of T cells and have several advantages over conventional T cells (Ramos and Dotti, *Expert Opin Biol Ther.*, 11:855-873 (2011), Curran, et al., *J Gene Med.*, 14:405-415 (2012), Maher, *ISRN Oncol.* 2012:278093 (2012)). CAR-T cells recognize and kill cancer cells independently of the major histocompatibility complex (MHC). Thus target cell recognition is unaffected by some of the mechanisms by which tumors evade MHC-restricted T-cell recognition, for example downregulation of human leukocyte antigen (HLA) class I molecules and defective antigen processing.

Chimeric immune receptors were initially developed in the 1980s and originally included the variable (antigen binding) regions of a monoclonal antibody and the constant regions of the T-cell receptor (TCR) α and β chains (Kuwana, et al., *Biochem Biophys Res Commun.*, 149:960-968 (1987)). In 1993 this design was modified to include an ectodomain, from a single chain variable fragment (scFv) from the antigen binding regions of both heavy and light chains of a monoclonal antibody, a transmembrane domain, and an endodomain with a signaling domain derived from CD3-ζ. Later CARs have generally followed a similar structural design, with a co-stimulatory signaling endodomain. Accordingly, the CAR constructs utilized in the methods herein can include an antigen binding domain or ectodomain, a hinge domain, a transmembrane domain, an endodomain, and combinations thereof.

In some embodiments the ectodomain is an scFv. The affinity of the scFv predicts CAR function (Hudecek, et al., *Clin Cancer Res.*, 19(12):3153-64 (2013), Chmielewski, et al., *J Immunol.*, 173:7647-7653 (2004)). Antigen binding and subsequent activation can also be modified by adding a flexible linker sequence in the CAR, which allows for expression of two distinct scFvs that can recognize two different antigens (Grada, et al., *Mol Ther Nucleic Acids*, 2:e105 (2013)) (referred to as tandem CARs (TanCARs)). Tandem CARS may be more effective in killing cancers expressing low levels of each antigen individually and may also reduce the risk of tumor immune escape due by single antigen loss variants. Other ectodomains include IL13Rα2 (Kahlon, et al., *Cancer Res.*, 64:9160-9166 (2004), Brown, et al., *Clin Cancer Res.*, 18(8):2199-209 (2012), Kong, et al., *Clin Cancer Res.*, 18:5949-5960 (2012), NKG2D-ligand and CD70 receptor, peptide ligands (e.g., TiE peptide ligand), and so-called "universal ectodomains" (e.g., avidin ectodomain designed to recognize targets that have been contacted with biotinylated monoclonal antibodies, or FITC-specific seFv designed to recognize targets that have been contacted with FITC-labeled monoclonal antibodies (Zhang, et al., *Blood*, 106:1544-1551 (2005), Barber, et al., *Exp Hematol.*, 36:1318-1328 (2008), Shaffer, et al., *Blood*, 117:4304-4314 (2011), Davies, et al., *Mol Med.*, 18:565-576 (2012), Urbanska, et al., *Cancer Res.*, 72:1844-1852 (2012), Tamada, et al., *Clin Cancer Res.*, 18:6436-6445 (2012)).

In some embodiments, the CAR includes a hinge region. While the ectodomain is important for CAR specificity, the sequence connecting the ectodomain to the transmembrane domain (the hinge region) can also influence CAR-T-cell function by producing differences in the length and flexibility of the CAR. Hinges can include, for example, a CH2CH3 hinge, or a fragment thereof, derived from an immunoglobulin such as IgG1. For example, Hudecek et al. (Hudecek, et al., *Clin Cancer Res.*, 19(12):3153-64 (2013)) compared the influence of a CH2-CH3 hinge [229 amino acids (AA)], CH3 hinge (119 AA), and short hinge (12AA) on the effector function of T cells expressing 3rd generation ROR1-specific CARs and found that T cells expressing 'short hinge' CARs had superior antitumor activity, while other investigators found that a CH2-CH3 hinge impaired epitope recognition of a 1st generation CD30-specific CAR (Hombach, et al., *Gene Ther.*, 7:1067-1075 (2000)).

Between the hinge (or ectodomain if no hinge domain) and the signaling endodomains typically lies a transmembrane domain, most typically derived from CD3-ζ, CD4, CD8, or CD28 molecules. Like hinges, the transmembrane domain can also influence CAR-T-cell effector function.

Upon antigen recognition, CAR endodomains transmit activation and costimulatory signals to T cells. T-cell activation relies on the phosphorylation of immunoreceptor tyrosine-based activation motifs (ITAMs) present in the cytoplasmic domain to the cytoplasmic CD3-ζ domain of the TCR complex (Irving, et al., *Cell*, 64:891-901 (1991)). Although the majority of CAR endomains contain an activation domain derived from CD3-ζ, others can include ITAM-containing domains such as the Fc receptor for IgE-γ domain (Haynes, et al., *J Immunol.*, 166:182-187 (2001)).

b. Exemplary Antigens and CAR Embodiments

The target specificity of the cell expressing a CAR is determined by the antigen recognized by the antibody/ectodomain. The disclosed compositions and methods can be used to create constructs, and cells expressing the constructs, that target any antigen. In the context of immunotherapy, particularly cancer immunotherapy, numerous antigens, and suitable ectodomains for targeting them, are well known. Unlike the native TCR, the majority of scFv-based CARs recognize target antigens expressed on the cell surface rather than internal antigens that are processed and presented by the cells' MHC, however, CARs have the advantage over the classical TCR that they can recognize structures other than protein epitopes, including carbohydrates and glycolipids Dotti, et al., *Immunol Rev.* 2014 January; 257(1): .doi:10.1111/imr.12131 (35 pages) thus increasing the pool of potential target antigens. Preferred targets include antigens that are only expressed on cancer cells or their surrounding stroma (Cheever, et al., *Clin Cancer Res.*, 15:5323-5337 (2009)), such as the splice variant of EGFR (EGFRvIII), which is specific to glioma cells (Sampson, et al., *Semin Immunol.*, 20(5):267-75 (2008)). However, human antigens meet this requirement, and the majority of target antigens are expressed either at low levels on normal cells (e.g. GD2, CAIX, HER2) and/or in a lineage restricted fashion (e.g. CD19, CD20).

Preferred targets, and CARs that target them are known in the art (see, e.g., Dotti, et al., *Immunol Rev.* 2014 January; 257(1):. doi:10.1111/imr.12131 (35 pages). For example, CAR targets for hematological malignancies include, but are not limited to, CD19 (e.g., B-cell) (Savoldo, et al., *J Clin Invest.*, 121:1822-1826 (2011), Cooper, et al., *Blood*, 105: 1622-1631 (2005); Jensen, et al., *Biol Blood Marrow Transplant* (2010), Kochenderfer, et al., *Blood*, 119:2709-2720 (2012), Brentjens, et al., *Molecular Therapy*, 17:5157 (2009), Brentjens, et al., *Nat Med.*, 9:279-286 (2003), Brentjens, et al., *Blood*, 118:4817-4828 (2011), Porter, et al., *N Engl J Med.*, 365:725-733 (2011), Kalos, et al., *Sci Transl Med.*, 3:95ra73 (2011), Brentjens, et al., *Sci Transl Med.*, 5:177ra38 (2013), Grupp, et al., *N Engl J Med* (2013)); CD20 (e.g., B-cell) (Jensen, et al., *Biol Blood Marrow Transplant* (2010), Till, et al., *Blood*, 112:2261-2271 (2008), Wang, et al., *Hum Gene Ther.*, 18:712-725 (2007), Wang, et al., *Mol Ther.*, 9:577-586 (2004), Jensen, et al., *Biol Blood Marrow Transplant*, 4:75-83 (1998)); CD22 (e.g., B-cell) (Hasa, et al., *Blood*, 121:1165-1174 (2013)); CD30 (e.g., B-cell) (Di Stasi, et al., *Blood*, 113:6392-6402 (2009), Savoldo, et al., *Blood*, 110:2620-2630 (2007), Hombach, et al., *Cancer Res.*, 58:1116-1119 (1998)); CD33 (e.g., Myeloid) (Finney, et al., *J Immunol*, 161:2791-2797 (1998)); CD70 (e.g., B-cell/T-cell) (Shaffer, et al., *Blood*, 117:4304-4314 (2011)); CD123 (e.g., Myeloid) (Tettamanti, et al., *Br J Haematol.*, 161:389-401 (2013)); Kappa (e.g., B-cell) (Vera, et al., *Blood*, 108:3890-3897 (2006)); Lewis Y (e.g., Myeloid) (Peinert, et al., *Gene Ther.*, 17:678-686 (2010), Ritchie, et al., *Mol Ther.* (2013)); NKG2D ligands (e.g., Myeloid) (Barber, et al., *Exp Hematol.*, 36:1318-1328 (2008), Lehner, et al., *PLoS One.*, 7:e31210 (2012), Song, et al., *Hum Gene Ther.*, 24:295-305 (2013), Spear, et al., *J Immunol.* 188:6389-6398 (2012)); ROR1 (e.g., B-cell) (Hudecek, et al., *Clin Cancer Res.* (2013)).

CAR targets for solid tumors include, but are not limited to, B7H3 (e.g., sarcoma, glioma) (Cheung, et al., *Hybrid Hybridomics*, 22:209-218 (2003)); CAIX (e.g., kidney) (Lamers, et al., *J Clin Oncol.*, 24:e20-e22. (2006)), Weijtens, et al., *Int J Cancer*, 77:181-187 (1998)); CD44 v6/v7 (e.g., cervical) (Hekele, et al., *Int J Cancer*, 68:232-238 (1996)), Dail, et al., *Cancer Immunol Immunother*, 54:51-60 (2005); CD171 (e.g., neuroblastoma) (Park, et al., *Mol Ther.*, 15:825-833 (2007)); CEA (e.g., colon) (Nolan, et al., *Clin Cancer Res.*, 5:3928-3941 (1999)); EGFRvIII (e.g., glioma) (Bullain, et al., *J Neurooncol.* (2009), Morgan, et al., *Hum Gene Ther.*, 23:1043-1053 (2012)); EGP2 (e.g., carcinomas) (Meier, et al., *Magn Reson Med.*, 65:756-763 (2011), Ren-Heidenreich, et al., *Cancer Immunol Immunother.*, 51:417-423 (2002)); EGP40 (e.g., colon) (Daly, et al., *Cancer Gene Ther.*, 7:284-291 (2000); EphA2 (e.g., glioma, lung) (Chow, et al., *Mol Ther.*, 21:629-637 (2013)); ErbB2(HER2) (e.g., breast, lung, prostate, glioma) (Zhao, et al., *J Immunol.*, 183:5563-5574 (2009), Morgan, et al., *Mol Ther.*, 18:843-851 (2010), Pinthus, et al., 114:1774-1781 (2004), Teng, et al., *Hum Gene Ther.*, 15:699-708 (2004), Stancovski, et al., *J Immunol.*, 151:6577-6582 (1993), Ahmed, et al., *Mol Ther.*, 17:1779-1787 (2009), Ahmed, et al., *Clin Cancer Res.*, 16:474-485 (2010), Moritz, et al., *Proc Natl Acad Sci*

U.S.A., 91:4318-4322 (1994)); ErbB receptor family (e.g., breast, lung, prostate, glioma) (Davies, et al., *Mol Med.*, 18:565-576 (2012)); ErbB3/4 (e.g., breast, ovarian) (Muniappan, et al., *Cancer Gene Ther.*, 7:128-134 (2000), Altenschmidt, et al., *Clin Cancer Res.*, 2:1001-1008 (1996)); HLA-A1/MAGE1 (e.g., melanoma) (Willemsen, et al., *Gene Ther.*, 8:1601-1608 (2001), Willemsen, et al., *J Immunol.*, 174:7853-7858 (2005)); HLA-A2/NY-ESO-1 (e.g., sarcoma, melanoma) (Schuberth, et al., *Gene Ther.*, 20:386-395 (2013)); FR-α (e.g., ovarian) (Hwu, et al., *J Exp Med.*, 178:361-366 (1993), Kershaw, et al., *Nat Biotechnol.*, 20:1221-1227 (2002), Kershaw, et al., *Clin Cancer Res.*, 12:6106-6115 (2006), Hwu, et al., *Cancer Res.*, 55:3369-3373 (1995)); FAP (e.g., cancer associated fibroblasts) (Kakarla, et al., *Mol Ther.* (2013)); FAR (e.g., rhabdomyosarcoma) (Gattenlohner, et al., *Cancer Res.*, 66:24-28 (2006)); GD2 (e.g., neuroblastoma, sarcoma, melanoma) (Pule, et al., *Nat Med.*, 14:1264-1270 (2008), Louis, et al., *Blood*, 118: 6050-6056 (2011), Rossig, et al., *Int J Cancer.*, 94:228-236 (2001)); GD3 (e.g., melanoma, lung cancer) (Yun, et al., *Neoplasia.*, 2:449-459 (2000)); HMW-MAA (e.g., melanoma) (Burns, et al., *Cancer Res.*, 70:3027-3033 (2010)); IL11Rα (e.g., osteosarcoma) (Huang, et al., *Cancer Res.*, 72:271-281 (2012)); IL13Rα2 (e.g., glioma) (Kahlon, et al., *Cancer Res.*, 64:9160-9166 (2004), Brown, et al., *Clin Cancer Res.* (2012), Kong, et al., *Clin Cancer Res.*, 18:5949-5960 (2012), Yaghoubi, et al., *Nat Clin Pract Oncol.*, 6:53-58 (2009)); Lewis Y (e.g., breast/ovarian/pancreatic) (Peinert, et al., *Gene Ther.*, 17:678-686 (2010), Westwood, et al., *Proc Natl Acad Sci U.S.A.*, 102:19051-19056 (2005), Mezzanzanica, et al., *Cancer Gene Ther.*, 5:401-407 (1998)); Mesothelin (e.g., mesothelioma, breast, pancreas) (Lanitis, et al., *Mol Ther.*, 20:633-643 (2012), Moon, et al., *Clin Cancer Res.*, 17:4719-4730 (2011)); Muel (e.g., ovarian, breast, prostate) (Wilkie, et al., *J Immunol.*, 180:4901-4909 (2008)); NCAM (e.g., neuroblastoma, colorectal) (Gilham, et al., *J Immunother.*, 25:139-151 (2002)); NKG2D ligands (e.g., ovarian, sacoma) (Barber, et al., *Exp Hematol.*, 36:1318-1328 (2008), Lehner, et al., *PLoS One*, 7:e31210 (2012), Song, et al., *Gene Ther.*, 24:295-305 (2013), Spear, et al., *J Immunol.*, 188:6389-6398 (2012)); PSCA (e.g., prostate, pancreatic) (Morgenroth, et al., *Prostate*, 67:1121-1131 (2007), Katari, et al., *HPB*, 13:643-650 (2011)); PSMA (e.g., prostate) (Maher, et al., *Nat Biotechnol.*, 20:70-75 (2002), Gong, et al., *Neoplasia.*, 1:123-127 (1999)); TAG72 (e.g., colon) (Hombach, et al., *Gastroenterology*, 113:1163-1170 (1997), McGuinness, et al., *Hum Gene Ther.*, 10:165-173 (1999)); VEGFR-2 (e.g., tumor vasculature) (*J Clin Invest.*, 120:3953-3968 (2010), Niederman, et al., *Proc Natl Acad Sci U.S.A.*, 99:7009-7014 (2002)).

2. Metabolic Stability

In some embodiments, cells' (e.g., CAR cells') metabolic stability is improved by equipping them with the capacity to make the very growth factors that are limiting in vivo. Exemplary results presented in the working Examples below show that electroporation with BCL-XL mRNA preserved greater than 95% cell viability for 5 days after transfection when cells were cultured in IL-2-depeleted medium. In some embodiments, cells are transiently transfected with an mRNA encoding an anti-apoptotic factor such as BCL-XL. B-cell lymphoma-extra large (Bcl-XL, or BCL2-like 1 isoform 1) is a transmembrane protein in the mitochondria. It is a member of the Bcl-2 family of proteins, and acts as a pro-survival protein in the intrinsic apoptotic pathway by preventing the release of mitochondrial contents such as cytochrome c, which would lead to caspase activation. Both amino acid and nucleic acid sequences encoding BCL-XL are known in the art and include, for example, UniProtKB-Q07817 (B2CL1_HUMAN), Isoform Bcl-X(L) (identifier: Q07817-1) (amino acid sequence); ENA|U72398|U72398.1 Human Bcl-x beta (bcl-x) gene, complete cds (genomic nucleic acid sequences); ENA|Z23115|Z23115.1 *H. sapiens* bcl-XL mRNA (mRNA/cDNA nucleic acid sequences).

Exemplary results presented in the working Examples below show that electroporation of 30 μg/ml of IL-2 mRNA resulted in a 3.5 fold T cell expansion over 7 days. In some embodiments, cells are transiently transfected with an mRNA encoding proliferation inducing factor such as IL-2. Both amino acid and nucleic acid sequences encoding IL-2 are known in the art and include, for example, UniProtKB-P60568 (IL2_HUMAN) (amino acid sequence); ENA|X00695|X00695.1 Human interleukin-2 (IL-2) gene and 5' flanking region (genic nucleic acid sequence); and ENA|V00564|V00564.1 Human mRNA encoding interleukin-2 (IL-2) (mRNA/cDNA nucleic acid sequence).

However, the production of secreted IL-2 may have the unwanted side effect of also stimulating the proliferation of the lymphoma and Treg cells, and impairing the formation of memory T cells (Zhang, et al., *Nature Medicine*, 11:1238-1243 (2005)). In addition, the use of IL-2 in patients treated with Tumor Infiltrating Lymphocytes (TILs) led to increased toxicity (Heemskerk, et al., *Human Gene Therapy*, 19:496-510 (2008)). To avoid this potentiality, in addition or alternative to IL-2, cells can be transiently transfected with mRNA encoding a chimeric γc cytokine receptor (CγCR) such as one composed of Interleukin-7 (IL-7) tethered to IL-7Rα/CD127 that confers exogenous cytokine independent, cell intrinsic, STAT5 cytokine signals (Hunter, et al., *Molecular Immunology*, 56:1-11 (2013)). The design is modular in that the IL-2Rβ/CD122 cytoplasmic chain can be exchanged for that of IL-7Rα/CD127, to enhance Shc activity. The constructs mimic wild type IL-2 signaling in human CD8+ T cells (Hunter, et al., *Molecular Immunology*, 56:1-11 (2013)) and should, therefore, work similarly to the IL-2 mRNA, without the unwanted to side effects.

Additionally and alternatively other antiapoptotic molecules and cytokines can be used to preserve cell viability in the native state. Exemplary factors include, but are not limited to:

Myeloid Cell Leukemia 1 (MCL-1) (e.g., UniProtKB-Q07820 (MCL1_HUMAN) (amino acid sequence); ENA|AF147742|AF147742.1 *Homo sapiens* myeloid cell differentiation protein (MCL1) gene, promoter and complete cds (genomic nucleic acid sequence); ENA|AF118124AP118124.1 *Homo sapiens* myeloid cell leukemia sequence 1 (MCL1) mRNA, complete cds. (mRNA/cDNA nucleic acid sequence)) which is an anti-apoptotic factor;

IL-7 (e.g., UniProtKB-P13232 (IL7_HUMAN) (amino acid sequence); ENA|EF064721|EF064721.1 *Homo sapiens* interleukin 7 (IL7) gene, complete cds. (genomic nucleic acid sequence); ENA|J04156|J04156.1 Human interleukin 7 (IL-7) mRNA, complete cds. (mRNA/cDNA nucleic acid sequence) which is important for T cell survival and development, and IL-15 (e.g., UniProtKB-P40933 (IL15_HUMAN) (amino acid sequence); ENA|X91233|X91233.1 *H. sapiens* IL15 gene (genomic nucleic acid sequence); ENA|U14407|U14407.1 Human interleukin 15 (IL15) mRNA, complete cds. (mRNA/cDNA nucleic acid sequence)) which promotes T and NK cell survival (Oferman, et al., *Nature*, 426: 671-676 (2003); Meazza, et al., *Journal of Biomedicine & Biotechnology*, 861920, doi: 10.1155/2011/861920 (2011); Michaud, et al., *Journal of*

*Immunotherapy,* 33:382-390 (2010)). These cytokine mRNAs can be used either independently or in combination with BCL-XL, IL-2, and/or CγCR mRNA. Accordingly, in some embodiments, cells transfected with an mRNA encoding MCL-1, IL-7, IL-15, or a combination thereof.

3. Inhibitory CAR (iCAR)

In some embodiments, the CAR cells are transfected with T cell therapies that have demonstrated long-term efficacy and curative potential for the treatment of some cancers, however, their use is limited by damage to non-cancerous tissues reminiscent of graft-versus-host disease after donor lymphocyte infusion. Any of the disclosed compositions and methods can be used in combination with a non-specific immunosuppression (e.g., high-dose corticosteroid therapy, which exert cytostatic or cytotoxic effects on T cells, to restrain immune responses), irreversible T cell elimination (e.g., so-called suicide gene engineering strategies), or a combination thereof. However, in some preferred embodiments, off-target effects are reduced by introducing into the CAR cell a construct encoding an inhibitory chimeric antigen receptor (iCAR). T cells with specificity for both tumor and off-target tissues can be restricted to tumor only by using an antigen-specific iCAR introduced into the T cells to protect the off-target tissue (Fedorov, et al., *Science Translational Medicine,* 5:215ra172 (2013)). The iCAR can include a surface antigen recognition domain combined with a powerful acute inhibitory signaling domain to limit T cell responsiveness despite concurrent engagement of an activating receptor (e.g., a CAR). In preferred embodiments, the iCAR includes a single-chain variable fragment (scFv) specific for an inhibitory antigen fused to the signaling domains of an immunoinhibitory receptor (e.g., CTLA-4, PD-1, LAG-3, 2B4 (CD244), BTLA (CD272), KIR, TIM-3, TGF beta receptor dominant negative analog etc.) via a transmembrane region that inhibits T cell function specifically upon antigen recognition. Once the CAR cell encounters a cell (e.g., a cancer cell) that does not express the inhibitory antigen, iCAR-transduced T cells can mount a CAR-induced response against the CAR's target antigen. A DNA iCAR using an scFv specific for PSMA with the inhibitory signaling domains of either CTLA-4 or PD-1 is discussed in (Fedorov, et al., *Science Translational Medicine,* 5:215ra172 (2013)).

Design considerations include that observation that PD-1 was a stronger inhibitor than CTLA-4, CTLA-4 exhibited cytoplasmic localization unless a Y165G mutant was used, and that the iCAR expression level is important.

iCAR can be designed against cell type specific surface molecules. In some embodiments the iCAR is designed to prevent T cell, NK cells, or other immune cell reactivity against certain tissues or cell types.

4. Reducing Endogenous Inhibitory Signaling

In some embodiments the cells are contacted with one or more RNA(s) that reprogram the cells to prevent expression of one or more antigens. For example, as discussed in more detail below, the RNA may be an interfering RNA that prevents expression of an mRNA encoding antigens as CTLA-4 or PD-1. This method can be used to prepare universal donor cells. RNAs used to alter the expression of allogenic antigens may be used alone or in combination with RNAs that result in de-differentiation of the target cell.

Although the section above provides compositions and methods that utilized inhibitory signaling domains e.g., CTLA-4 or PD-1 in an artificial iCAR to restrict on-target/ off-tumor cytotoxicity, additionally or alternatively overall CAR cell on-tumor effector efficiency can be increased by reducing the expression of endogenous inhibitory signaling in the CAR cells so that the CAR cells become resistant to the inhibitory signals of the hostile tumor microenvironment.

CTLA-4 and PD-1 inhibit T cells at different stages in activation and function. CTLA-4 regulates T cell responses to self-antigens, as knockout mice spontaneously develop organ damage due to highly active, tissue-infiltrating T cells without specific antigen exposure (Tivol, et al., *Immunity,* 3:541-547 (1995); Waterhouse, et al., Science, 270:985-988 (1995)). Interestingly, conditional knockout of CTLA-4 in Treg cells recapitulates the global knockout indicating that it normally functions within Tregs (Wing, et al., Science, 322:271-275 (2008)). In contrast, PD-L1 knockout mice are autoimmune prone, but do not spontaneously develop massive inflammatory cell infiltration of normal organs, indicating that it's major physiological function is to mediate negative feedback control of ongoing tissue inflammation in an inducible manner (Dong, et al., Immunity, 20:327-336 (2004)). Indeed, according to the "adaptive resistance" hypothesis most tumors up-regulate PD-L1 in response to IFNγ; a key cytokine released by effector T cells including CART cells (Greenwald, et al., *Annu Rev Immunol,* 23:515-548 (2005); Carreno, et al., *Annu Rev Immunol,* 20:29-53 (2002); Chen, et al., *The Journal of Clinical Investigation,* 125:3384-3391 (2015); Keir, et al., *Annu Rev Immunol,* 26:677-704 (2008); Pentcheva-Hoang, et al., *Immunological Reviews,* 229:67-87 (2009)). PD-L1 then delivers an inhibitory signal to T cells decreasing their proliferation, and cytokine and perforin production (Butte, et al., *Immunity,* 27:111-122 (2007); Chen, et al., *Immunology,* 4:336-347 (2004); Park, et al., Blood, 116:1291-1298 (2010); Wherry, et al., *Nat Immunol,* 12:492-499 (2011); Zou, et al., *Immunology,* 8:467-477 (2008)). In addition, reverse signaling from the T cell through B7-H1 on cancer cells induces an anti-apoptotic effect that counteracts Fas-L signaling (Azuma, et al., *Blood,* 111:3635-3643 (2008)). Azuma, et al., *Blood,* 111:3635-3643 (2008)

In light of the up-regulation of B7-H1 by cancer cells and the association of its expression with cancer progression and poor clinical outcome (Flies, et al., Journal of Immunotherapy, 30:251-260 (2007); Nishimura, et al., *Immunity,* 11:141-151 (1999); Wang, et al., *Curr Top Microbiol Immunol,* 344:245-267 (2011)), antibodies antagonizing the PD-1 and CTLA-4 pathways have shown dramatic efficacy in solid tumors, particularly melanoma, with the combination of the two showing even more activity. The anti-CTLA-4 antibody, ipilimumab, improves overall survival in metastatic melanoma with increased T cell infiltration into tumors and increased intratumoral CD8+:Treg ratios, predominantly through inhibition of Treg cells (Hamid, et al., *J Transl Med,* 9:204 (2011); Ribas, et al., *Clinical Cancer Research: An Official Journal of the American Association for Cancer Research,* 15:6267-6276 (2009); Twyman-Saint, et al., *Nature,* 520:373-377 (2015)). The anti-PD-1 antibody, nivolumab, shows an overall response rate of 30-40% in metastatic melanoma (Robert, et al., *The New England Journal of Medicine,* 372:320-330 (2015); Topalian, et al., *J Clin Oncol,* 32:1020-1030 (2014)), with similar findings in early phase clinical trials for other solid tumors including metastatic renal cancer, non-small cell lung cancer and relapsed Hodgkin's Lymphoma (Ansel, et al., *The New England Journal of Medicine,* 372:311-319 (2015); Brahmer, et al., *J Clin Oncol,* 28:3167-3175 (2010); Topalian, et al., *The New England Journal of Medicine,* 366:2443-2454 (2012)). As resistance to anti-CTLA-4 antibodies in mouse melanoma models is due to up-regulation of PD-L1[81], the combination of both ipilimumab and nivolumab demonstrates further efficacy in both mouse models and human patients (Larkin, et al., *The New England Journal of Medicine*, 373:23-34 (2015); Spranger, et al., *J Immunother Cancer*, 2, 3, doi:10.1186/2051-1426-2-3 (2014); Yu, et al., *Clinical Cancer Research: An Official Journal of the American Association for Cancer Research*, 16:6019-6028 (2010)). Given the importance of the checkpoint inhibition pathway, it is believed that PD-1/CTLA-4 inhibition will release the brake, while the chimeric antigen receptor will push on the gas pedal. Importantly, transient transfection can be utilized to only transiently release the brake so that these cells will not lead to future autoimmune disease.

a. CRISPRi

To avoid permanent genome modification and inactivation of inhibitory signals such as PD-1 and CTLA-4, the dCAS9 CRISPRi system (Larson, et al., *Nat Protoc*, 8:2180-2196 (2013)) can be utilized. mRNAs corresponding to the enzymatically-inactive dCAS9-KRAB-repression domain, fusion protein, and sgRNAs to the inhibitory signaling protein (e.g. CTLA-4, PD-1, LAG-3, 2B4 (CD244), BTLA (CD272), KIR, TIM-3, TGF beta receptor dominant negative analog, etc.) can be co-transfected into the CAR cell. One or multiple sgRNA can be utilized. sgRNA can be designed to target the proximal promoter region and the coding region (nontemplate strand). Although Cas9 is a long transcript (>4,100 nt), synthesis and electroporation has been successful with mRNA molecules over 6 Kb. Furthermore, electroporation of sgRNA-Cas9 ribonucleoproteins into primary human T cells was able to direct recombination repair with 20-40% efficiency at the PD-1 and CXCR4 loci (Schumann, et al., *Proceedings of the National Academy of Sciences of the United States of America*, 112:10437-10442 (2015)) and inhibition of gene expression by CRISPRi achieves up to 80% efficiency (Gilbert, et al., *Cell*, 154:442-451 (2013)). An alternative approach utilizes the single-component Cpf1 CRISPR system, which is a smaller RNA to electroporate and express (Zetsche, et al., *Cell*, doi: 10.1016/j.cell.2015.09.038 (2015)). Although broad inhibition of CTLA-4 with ipilimumab results in autoimmune sequelae, it is believed these side-effects will be decreased by restricting loss to CAR cells and transient nature of the mRNA transfection. Inhibitory function will be regained in time.

b. Inhibitory RNAs

Cells can also be transfected with a functional RNA or an mRNA encoding a functional nucleic acid or polypeptide designed to target and reduce or inhibit expression or translation of an inhibitory signaling molecule mRNA; or to reduce or inhibit expression, reduce activity, or increase degradation of inhibitory signaling molecule protein. Suitable technologies include, but are not limited to, antisense molecules, siRNA, miRNA, aptamers, ribozymes, triplex forming molecules, RNAi, etc. In some embodiments, the mRNA encode antagonist polypeptide that reduce inhibitory signaling.

In some embodiments, the cells can be transiently transfected with one or more functional RNAs suitable to reducing or silencing expression of CTLA-4, PD-1, LAG-3, 2B4 (CD244), BTLA (CD272), KIR, TIM-3, TGF beta receptor dominant negative analog, etc. alone or in combination. For example, gene expression can be effectively silenced in a highly specific manner through RNA interference (RNAi). This silencing was originally observed with the addition of double stranded RNA (dsRNA) (Fire, et al. (1998) Nature, 391:806-11; Napoli, et al. (1990) Plant Cell 2:279-89; Hannon, (2002) Nature, 418:244-51). Once dsRNA enters a cell, it is cleaved by an RNase III-like enzyme, Dicer, into double stranded small interfering RNAs (siRNA) 21-23 nucleotides in length that contains 2 nucleotide overhangs on the 3' ends (Elbashir, et al. (2001) Genes Dev., 15:188-200; Bernstein, et al. (2001) Nature, 409:363-6; Hammond, et al. (2000) Nature, 404:293-6). In an ATP dependent step, the siRNAs become integrated into a multi-subunit protein complex, commonly known as the RNAi induced silencing complex (RISC), which guides the siRNAs to the target RNA sequence (Nykanen, et al. (2001) Cell, 107:309-21). At some point the siRNA duplex unwinds, and it appears that the antisense strand remains bound to RISC and directs degradation of the complementary mRNA sequence by a combination of endo and exonucleases (Martinez, et al. (2002) Cell, 110:563-74). However, the effect of iRNA or siRNA or their use is not limited to any type of mechanism.

Short Interfering RNA (siRNA) is a double-stranded RNA that can induce sequence-specific post-transcriptional gene silencing, thereby decreasing or even inhibiting gene expression. In one example, a siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends, herein incorporated by reference for the method of making these siRNAs.

Sequence specific gene silencing can be achieved in mammalian cells using synthetic, short double-stranded RNAs that mimic the siRNAs produced by the enzyme dicer (Elbashir, et al. (2001) Nature, 411:494 498) (Ui-Tei, et al. (2000) FEBS Lett 479:79-82). siRNA can be chemically or in vitro-synthesized or can be the result of short double-stranded hairpin-like RNAs (shRNAs) that are processed into siRNAs inside the cell.

In some embodiments, the RNA is an mRNA that encodes a polypeptide that reduces bioavailability or serves as an antagonist or other negative regulator or inhibitor of CTLA-4, PD-1, LAG-3, 2134 (CD244), BTLA (CD272), KIR, TIM-3, TGF beta receptor dominant negative analog, or another protein in an immune inhibitory pathway. The protein can be a paracrine, endocrine, or autocrine. It can regulate the cell intracellularly. It can be secreted and regulate the expressing cell and/or other (e.g., neighboring) cells. It can be a transmembrane protein that regulates the expressing cell and/or other cells. The protein can be fusion protein, for example an Ig fusion protein.

5. Pro-apoptotic Factors

Compositions and methods for activating and reactivating apoptotic pathways are also provided. In some embodiments, subjects are treated with a combination of transiently transfected cells, such as CAR T cells prepared by transient transfection, and a factor or agent that activates, reactivates, or otherwise enhances or increases the intrinsic apoptosis pathway. Preferably the factor activates, reactivates, or otherwise enhances the intrinsic apoptosis pathway in cancer (e.g., tumor) cells, and is more preferably specific or targeted to the cancer cells.

In some embodiments, cells transfected with an anti-apoptotic factor or pro-proliferation factor, such as those discussed above or otherwise known in the art, are more resistant or less sensitive to induced apoptosis than untransfected cells. In an exemplary strategy, a subject is administered a combination of (1) transfected cells, e.g., CART cells, co-transfected with a CAR construct and an anti-apoptotic or pro-viability factor such as BCL-XL, IL-2, CγCR, or a combination thereof, and (2) a pro-apoptotic factor. The pro-apoptotic factor induces or increases apoptosis in untransfected cells relative to the transfected T cells, and is preferably selective for cancer cells. The regimen results in a two-pronged attack, one cellular and one molecular, against the cancer cells.

The intrinsic apoptosis pathway can be activated, reactivated, or otherwise enhanced by targeting BCL-2 family members. BCL-2 family members are classified into three subgroups based on function and Bcl-2 Homology (BH) domains: multi-domain anti-apoptotic (e.g. BCL-2 or BCL-XL), multi-domain pro-apoptotic (e.g. BAX and BAK), and BH3-only pro-apoptotic (e.g. BIM) proteins. Members of the BH3-only subgroup, such as BIM, function as death sentinels that are situated throughout the cell, poised to transmit a variety of physiological and pathologic signals of cellular injury to the core apoptotic machinery located at the mitochondrion (Danial, et al., *Cell*, 116:205-219 (2004)). Depending on the nature of apoptotic stimuli and cellular context, the BH3-only protein's death signal will either be neutralized by anti-apoptotic proteins or delivered to the mitochondrial executioners, BAX and BAK (Green, et al., *Cell*, 121:671-674 (2005)). Upon activation, BAX and BAK oligomerize and induce permeabilization of the outer mitochondrial membrane, enabling released mitochondrial factors to activate caspases that execute the cell death program (Antonsson, et al., *J Biol Chem*, 276:11615-11623 (2001); Jurgensmeier, et al., *Proc Natl Acad Sci USA*, 95:4997-5002 (1998); Degenhardt, et al., *J Biol Chem*, 277:14127-14134 (2002); Antonsson, et al., Biochem J, 345 Pt 2:271-278 (2000)).

In some embodiments, the pro-apoptotic factor is a pro-apoptotic BH3-mimetic. Various pro-apoptotic BH3-mimetics can simulate the native pro-apoptotic activities of BIM and afford the ability to manipulate multiple points of the apoptotic pathway. For example, BIM SAHB (Stabilized Alpha Helix of BCL-2 domains), ABT-737, and ABT-199 are pro-apoptotic BH3-mimetics designed by structural studies of the interaction between the pro-apoptotic BH3-only helical domain and the hydrophobic groove formed by the confluence of the BH1, BH2 and BH3 domains of anti-apoptotic proteins (Oltersdorf, et al., *Nature*, 435:677-681 (2005)). BIM SAHB is a synthetic peptide modeled on the BIM BH3 death domain with an all-hydrocarbon cross-link inserted that stabilizes its a-helical structure, enhances its half-life, and confers cellular permeability such that the genetic pathway of apoptosis can be reactivated in cancer cells in vivo (LaBelle, et al., *The Journal of Clinical Investigation*, 122:2018-2031 (2012)).

The sequence of BIM SAHB corresponds with BIM BH3 helix amino acids 146-166. In some embodiments the pro-apoptotic BH3-mimetic is a BIM SAHB, for example a polypeptide including the sequence IWIAQELRXIGDXF-NAYYARR (SEQ ID NO:1), wherein "X" denotes the position of the nonnatural S-pentenyl alanine derivative (Schafmeister, et al., *J. Am. Chem. Soc.*, 122, 5891-5892 (2000); Williams and Im, *J. Am. Chem. Soc.* 113, 9276-9286 (1991)), or a functional fragment or variant of SEQ ID NO:1 that activates, reactivates, or enhances cell death in a BH3 sequence-dependent fashion, and preferably preferentially affects cells driven by a deregulated apoptotic pathway. An intramolecular all-hydrocarbon crosslink can subsequently be generated by ruthenium catalyzed olefin metathesis (Blackwell and Grubbs, *Angew. Chem. Int. Ed. Engl.*, 37, 3281-3284 (1994); Schafmeister, et al., *J. Am. Chem. Soc.*, 122, 5891-5892 (2000)). Introduction of an all-hydrocarbon crosslink into the native BH3 peptide sequence overcomes many of the shortcomings of synthetic peptides, and successfully: (1) restores and stabilizes α-helical structure, (2) enhances peptide half-life, and (3) confers cellular permeability.

BIM SAHB targets the broad range of anti-apoptotic proteins (e.g. BCL-2, BCL-XL, BCL-w, MCL-1 and BFL1/A1) as well as directly activates the multi-domain pro-apoptotic proteins, BAX and BAK (LaBelle, et al., *The Journal of Clinical Investigation*, 122:2018-2031 (2012); Gavathiotis, et al., *Nature*, 455:1076-1081 (2008)). Furthermore, BIM SAHB induced apoptosis in multiple hematologic cancer cell lines in vitro and in xenograft models in vivo (LaBelle, et al., *The Journal of Clinical Investigation*, 122:2018-2031 (2012)). BIM SAHB also appears to impose a preferential toxicity upon cancer cells driven by deregulated apoptosis, as BIM SAHB did not induce a significant change in viability for non-malignant fibroblasts in vitro or in TUNEL positivity in other mouse tissues in vivo at the same dosing levels (LaBelle, et al., *The Journal of Clinical Investigation*, 122:2018-2031 (2012)).

In some embodiments, the pro-apoptotic BH3-mimetic is a small molecule such as ABT-737, ABT-263, or ABT-199. ABT-737 and the oral derivative ABT-263 are small molecules designed to selectively inhibit BCL-2, BCL-XL and BCL-w with high affinity (Oltersdorf, et al., *Nature*, 435: 677-681 (2005); Tse, et al., *Cancer Research*, 68:3421-8 (2008)). Finally, ABT-199 was developed to exclusively inhibit BCL-2; since ABT-737 results in thrombocytopenia due to on target inhibition of BCL-XL in platelets (Sowers, et al., *Nature Medicine*, 19:202-208 (2013)). Like CAR-T cells, pro-apoptotic BCL-2 family inhibitors have enjoyed remarkable efficacy with minimal adverse events in preclinical and early clinical trials for various hematopoietic neoplasms, including MCL (Beltran, et al., Proceedings of the National Academy of Sciences of the United States of America, 108:12461-12466 (2011); Gandhi, et al., *Journal of Clinical Oncology: Official Journal of the American Society of Clinical Oncology*, 29:909-916 (2011); Roberts, et al., *Journal of Clinical Oncology: Official Journal of the American Society of Clinical Oncology*, 30:488-496 (2012); Touzeau, et al., *Clinical Cancer Research: An Official Journal of the American Association for Cancer Research*, 17:5973-5981 (2011); Wilson, et al., *The Lancet Oncology*, 11:1149-1159 (2010)).

Previous studies have shown that ABT-737 potentiates dendritic cell immunotherapy (Begley, et al., *Cancer Immunology, Immunotherapy: CII*, 58:699-708 (2009)), synergizes with TRAIL (Song, et al., *The Journal of Biological Chemistry*, 283:25003-25013 (2008)) and enhances CD19 CAR-T cell cytoxoicity (Karlsson, et al., *Cancer Gene Therapy*, 20:386-393 (2013)). However, this last study required pre-treatment with ABT-737 before introducing the CAR-T cells in order to avoid ABT 737-mediated death of the transfused CAR-T cells.

It is believed that mRNA mediated overexpression of anti-apoptotic proteins and cytokine signaling proteins, in CAR immune cells will confer them with resistance to ABT-199 or ABT-737 and thereby maximize the effect of a combination of pro-apoptotic and CAR therapies. For example, ABT-199 exclusively inhibits BCL-2 and not BCL-XL, MCL-1 or other family members. Therefore, electroporation of cells with BCL-XL mRNA should protect them from ABT-199.

Likewise, cytokine mRNAs such as IL-2 or a CγCR can make the reprogrammed cells resistant to apoptosis. CγCR cytokine signaling mimics IL-2 signaling and should, therefore, also promote CAR-T cell apoptotic resistance by decreasing BIM expression and increasing BCL-2 expression (Hunter, et al., *Molecular Immunology*, 56:1-11 (2013); Chougnet, et al., *Journal of Immunology*, 186:156-163 (2011); Scheel-Toellner, et al., *Apoptosis: An International Journal on Programmed Cell Death*, 13:109-117 (2008)). In addition, since the cytokine is tethered to the receptor, the CAR-T cells receive the anti-apoptotic, proliferative, and metabolic benefits of the cytokine independence in an autocrine fashion, without paracrine effects on the lymphoma or Treg cells. Whereas permanent cytokine independence of T cells might be dangerous and lead to uncontrollable T cell activation in a T cell reprogrammed with DNA, the transitory nature of mRNA reprogramming avoids this complication. Moreover, CAR-T cells resistant to apoptosis and with their own supply of IL-2 signaling by CγCR, may resist the suppression observed in some patients and not have to compete with resident T cells for a limited supply of growth factors, thus avoiding the need for prior lymphodepletion with cyclophosphamide, a strategy often employed by current protocols (Barrett, et al., *Human Gene Therapy*, 24:717-727 (2013)).

In particular embodiments, a BH3 mimetic and CD8+ T cells transfected with the combination of CD19 CAR, BCL-XL and CγCR mRNAs are administered to a subject in need thereof, for example by intravenously (iv) injection. The regimen can treat one or more symptoms of can relative to No BH3 mimetic, no T cells, T cells mock electroporated or T cells reprogrammed with only CD19 CAR controls. In specific embodiments, the subject is treated every three days.

6. Cell Selection

Different type of cells can be utilized for immunodulation and CAR-based therapies. The cell population chosen for reprogramming can be just as important to the treatment efficacy as the mRNAs used to reprogram them. The optimal engineered T cells will likely vary depending on the tumor and goals of the adoptive therapy. Effector T cells are typically preferred because they secreted high levels of effector cytokines and were proficient killers of tumor targets in vitro (Barrett, et al., *Annu Rev Med.*, 65: 333-347 (2014). Two complimentary lymphocyte populations with robust CAR mediated cytotoxicity are CD3-CD56+ NK cells and CD3+CD8+ T cells. Use of CD8+ T cells with CD4+ helper T cells leads to the increased presence of suppressive T-reg cells and dampened CD8+ T cell cytotoxicity. Since mRNA-reprogrammed CD8+ T cells are pre-activated so that they act directly on tumor cells without the need for activation in the lymph node, CD4+ T cell support is not essential.

Additionally, there is evidence that infusion of naive T cells (Rosenberg, et al. *Adv. Cancer Res.*, 25:323-388 (1977)), central memory T cells ($T_{CM}$ cells) (Berger, et al. *J. Clin. Invest.*, 118:294-305 (2008)), Th17 cells (Paulos, et al., *Sci. Transl. Med.*, 2:55-78 (2010)), and T stem memory cells (Gattinoni, et al., *Nat. Med.*, 17:1290-1297 (2012)) may all have certain advantages in certain applications due, for example, to their high replicative capacity. Tumor Infiltrating Lymphocytes (TILs) also have certain advantages due to their antigen specificity and may be used in RNA-based transfection strategies disclosed herein. Although sometime referred to as CAR cells, CAR immune, cells, and CART cells (or CAR T cells), it will be appreciated that the CAR and other RNA-based transfection strategies disclosed herein can also be carried out in other cell types, particularly different types of immune cells, including those discussed herein (e.g., lymphocytes, Natural Killer Cells, dendritic cells, B cells, antigen presenting cells, macrophage, etc.) and described elsewhere (see, e.g., Barrett, et al., *Annu Rev Med.*, 65: 333-347 (2014)).

7. Exemplary Therapeutic Strategies

The disclosed compositions and methods of use are modular in nature and can be combined in virtually any combination to create an irnmunotherapeutic strategy tailored to a subject's disease or condition. As is known in art, the CAR construct, particularly the antigen binding (ectodomain) portion can be selected based on the target cancer cells and the antigens expressed by them. The CAR modified cells can be further transfected with (1) mRNA encoding CAR cell survival and metabolic stability factors (e.g., anti-apoptotic factors, pro-viability factors, etc.), (2) factors controlling the ability to distinguish tumor from normal cells (e.g., iCAR), (3) factors that reduce immunosuppression (e.g., CRISPRi, inhibitory RNA, etc.), and combinations thereof. Cells can also be administered to subjects in combination with pro-apoptotic factors such as BIM SAHB, ABT-737, ABT-263, or ABT-199, and/or traditional compositions of cancer treatment such as chemotherapy and radiation therapy. In some embodiments, one or more RNAs are introduced into the cells that code for a molecule that attracts the transfected cell (such as T cells, NK cells, macrophages, dendritic cells etc.) to a specific tissue or anatomic site, such as lymphoid follicles. Exemplary therapeutic strategies tailored to more specific disease conditions are described in more detail below.

a. Mantle Cell Lymphoma

Mantle Cell Lymphoma (MCL) accounts for 5-10% of all non-Hodgkin lymphomas and has an aggressive clinical course with a median survival of approximately 3 to 5 years and few long-term survivors (Bertoni, et al., *Int J Biochem Cell Biol*, 39:1747-1753 (2007)). There is currently no curative standard therapy for MCL and even bone marrow transplantation suffers from a high failure rate (Fisher, et al., *J Clin Oncol*, 23:657-658 (2005)). Thus, there is an urgent need to advance new therapeutic strategies to treat MCL. Virtually all cases of MCL contain a t(11; 14)(q13; q32) translocation, placing the cyclin D1 gene under control of the immunoglobulin heavy chain promoter (Li, et al., *Am J Pathol*, 154:1449-1452 (1999)). This translocation results in the overexpression of cyclin D1, which phosphorylates the retinoblastoma protein, leading to unrestrained cell proliferation (Hinds, et al., *Proc Natl Acad Sci USA*, 91:709-713 (1994); Deshpande, et al., *Oncogene*, 24:2909-2915 (2005)).

Interestingly, transgenic mouse models of cyclin D1 overexpression alone do not recapitulate an MCL phenotype (Bodrug, et al., *Embo J*, 13:2124-2130 (1994); Lovec, et al., *Embo J*, 13:3487-3495 (1994)). Indeed, comparative genomic hybridization (CGH) and chromosomal banding studies have identified many additional genetic aberrations in MCL (Mestre-Escorihuela, et al., *Blood*, 109:271-280 (2007); Tagawa, et al., *Oncogene*, 24:1348-1358 (2005)). Of particular interest, the pro-apoptotic BCL-2 family member BIM showed biallelic deletion in 42% of 12 MCL cell lines and loss of expression in 32% of 22 patient samples by tissue microarray. In addition, anti-apoptotic BCL-2 overexpression is seen in almost 97% of cases (Tracey, et al., *The Journal of Pathology*, 206:123-134 (2005)) with 15% showing specific genomic gains or amplifications at the BCL-2 locus (Beltran, et al., *Proceedings of the National Academy of Sciences of the United States of America*, 108:12461-12466 (2011)). Immune stimulation of cyclin D1 transgenic mice bearing Bim-deficient B-cells induces a Mantle Cell Lymphoma phenotype (Katz, et al., *Blood*, 123:884-893 (2014)). These data indicate that prevention of apoptosis is important for MCL survival.

CD19 CAR-T cells are reprogrammed, tumor-selective and highly cytotoxic cells that harness the power of the immune system and direct it towards tumors. BH3 mimetics are small molecules and cell-permeable peptides that retain the specificity of native BH3 death ligands. Accordingly, in some embodiments a multidisciplinary approach is employed that combines mRNA reprogrammed CAR-T cells with a pro-apoptotic BM mimetic stimulus to overcome a clinically-relevant apoptotic blockade in Mantle Cell Lymphoma. In particular, the multifactorial nature of mRNA reprogramming of T cells can be utilized to additionally protect the CAR-T cells from BH3-mimetic induced apoptosis, while simultaneously activating apoptosis in this chemoresistant lymphoma.

In a particularly preferred strategy for treating MCL subjects with MCL are administered a combination of (1) CAR cells such as CART cells or CAR-NK cells transiently transfected with mRNAs encoding (i) a CD19 chimeric antigen receptor and (ii) one or more cell survival and metabolic stability factors such as BCL-XL, IL-2, and CγCR; and (2) a pro-apoptotic factor such as BIM SAHB, ABT-737, ABT-263, or ABT-199. Typically, the CAR cells are transfected ex vivo with mRNA prepared in vitro using a DNA template designed according to the guidelines disclosed herein.

b. Solid Tumors

CD276 (B7-H3) is a glycoprotein that is present on a broad spectrum of human solid tumors, including 88% of neuroectodermal tumors (e.g. melanoma, neuroblastoma, glioblastoma), 96% of mesenchymal tumors (e.g. rhabdomyosarcoma, osteosarcoma) and 80-90% of epithelial tumors (e.g. breast, hepatocellular, ovarian, pancreas, lung, colorectal). However, like many tumor associated antigens there is very low to absent expression on normal tissues, which could lead to on-target, off-tumor toxicity (Boland, et al., *Clin Lung Cancer*, 14:157-163 (2013); Chen, et al., *Proceedings of the National Academy of Sciences of the United States of America*, doi:10.1073/pnas.1516991112 (2015); Flies, et al., *Journal of Immunotherapy*, 30:251-260 (2007); Greenwald, et al., *Annu Rev Immunol*, 23:515-548 (2005); Ingebrigtsen, et al., *BMC Cancer*, 14:602 (2014); Kang, et al., *Oncol Rep*, 33:274-282 (2015); Liu, et al., *Mol Med Rep*, 7:134-138 (2013); Modak, et al., *Cancer Research*, 61:4048-4054 (2001); Sun, et al., *Cancer Immunol Immunother*, 61:2171-2182 (2012); Wang, et al., Cancer Invest, 32:262-271, doi:10.3109/07357907.2014.909826 (2014); Zang, et al., Mod Pathol, 23:1104-1112 (2010); Zhang, et al., Cell Mol Immunol, 2:307-311 (2005)). This type of toxicity has had lethal consequences in CART clinical trials for renal cell carcinoma against the CAIX antigen, which is also expressed at low levels in the liver (Lamers, et al., *Molecular Therapy: The Journal of the American Society of Gene Therapy*, 21:904-912 (2013)) as well as for colon cancer with an ERBB2 CAR that led to pulmonary toxicity (Morgan, et al., *Molecular Therapy: The Journal of the American Society of Gene Therapy*, 18:843-851 (2010).

While CD276 is upregulated in a diverse array of solid tumors, there is also a low level of expression in monocytes and dendritic cells (Zhang, et al., Cell Mol Immunol, 2:307-311 (2005)) that might hamper its utility for CART cell therapy of solid tumors. One elegant solution for imperfect targeting antigens is the development of inhibitory CARs (iCARs) shown in proof-of-principle experiments by the Sadelain group (Fedorov, et al., *Science Translational Medicine*, 5:215ra172 (2013)) and discussed in more detail above. iCARs recognize antigens unique to the normal tissue and deliver an inhibitory signal to counteract the CAR activation signal. CD123 is also expressed on monocytes and dendritic cells (Li, et al., *Mol Immunol*, 48:1121-1127 (2011); MacDonald, et al., *Blood*, 100:4512-4520 (2002); Shi, et al., *Cancer Lett*, 270:19-29 (2008)) as well as Acute Myeloid Leukemia myeloblasts (Gill, et al., *Blood*, 123: 2343-2354 (2014); Mardiros, et al., *Blood*, 122:3138-3148 (2013); Tettamanti, et al., *British Journal of Haematology*, 161:389-401 (2013)), which has led to its development as a CD123 CAR for AML, making it an attractive target for an iCAR. An exemplary CD123 iCAR includes the scFv clone 32716 (Du, et al., *Journal of Immunotherapy*, 30:607-613 (2007)), the CD8 transmembrane and hinge domains and the cytoplasmic domain of either CTLA-4 (amino acids 161-223) or PD-1 (amino acids 145-288). The CTLA-4 cytoplasmic domain can contain a Y165F mutation to prevent cytoplasmic localization by tyrosine phosphorylation, but retain similar amino acid structure as opposed to a glycine, which can break alpha-helices.

The original report of the anti-CD276 antibody revealed heterogeneous expression in the liver (Modak, et al., *Cancer Research*, 61:4048-4054 (2001)). A later study of human hepatocellular carcinoma revealed weak CD276 expression in 94% of normal, peritumor liver cells and moderate expression in 6% (Sun, et al., *Cancer Immunol Immunother*, 61:2171-2182 (2012)). In addition to the CD276 CAR, development of a hepatocyte iCAR could be useful for the CD33 CAR being developed for AML. Although no adverse, hepatotoxic reactions have been seen in mice (Kenderian, et al., *Leukemia: Official Journal of the Leukemia Society of America, Leukemia Research Fund*, doi:10.1038/leu.2015.52 (2015); Pizzitola, et al., Leukemia: Official Journal of the Leukemia Society of America, Leukemia Research Fund, U.K., 28:1596-1605 (2014)), there is some evidence for CD33 expression in the liver (Maniecki, et al., *Leukemia Research*, 35: e84-86 (2011)) that potentially led to hepatotoxicity in a clinical trial of gemtuzumab ozogamicin, an anti-CD33 monoclonal antibody (Kung, et al., *Blood*, 122:1455-1463 (2013)), as well as in a single patient treated with CD33 CART cells (Wang, et al., *Molecular Therapy: The Journal of the American Society of Gene Therapy*, 23:184-191 (2015). An hepatocyte iCAR can be constructed similarly to the myeloid iCAR described above, but the extracellular scFv portion can be taken from the anti-hepatic asialoglycoprotein receptor scFv (C1) (Wang, et al., *Cell Biochem Funct*, 31:698-706 (2013))

In order to both increase specificity with less broad toxicity and to increase efficacy by spatially and temporally linking both signals, one or more inhibitor signals such as CTLA-4 and PD-1 can be targeted in the same cells reprogrammed with CD276 CAR.

Accordingly, in a particularly preferred strategy for treating solid tumors, a subject is administered CAR cells such as CART or CAR-NK cells, transiently transfected with mRNAs encoding (1) a CD276 chimeric antigen receptor, in combination with (2) (i) one or more cell survival and metabolic stability factors such as BCL-XL, IL-2, and CγCR; a (ii) one or more iCAR constructs targeting, for example an myeloid/dendritic cell antigen (e.g. CD123), a hepatocyte antigen (e.g., hepatic asialoglycoprotein receptor), or combination thereof; (iii) one or more factors that reduce immunosuppression (e.g., CRISPRi, inhibitory RNA, etc.); or (iv) any combination of (i), (ii), and (iii).

Furthermore, although intratumoral delivery of short lived mRNA reprogrammed CART cells can induce target epitope spreading as a consequence of inflammation and tumor destruction (Beatty, et al., *Cancer Immunology Research*, 2:112-120 (2014)), it is believed that T cells could stop expressing the CAR before reaching tissues outside the tumor. By accurately adjusting the CAR mRNA load of the T cells used for intratumoral delivery, one can achieve the duration of CAR expression sufficient for effector function within the tumor and with much less pronounced effects outside. Thus in some embodiments, the CAR cells are administered locally to site of the tumor, for example, by injection into the tumor or its microenvironment.

c. Acute Myeloid Leukemia (AML)

Acute Myeloid Leukemia (AML) and Myelodysplastic Syndrome (MDS) are heterogeneous groups of acquired hematopoietic stem cell disorders that affect over 30,000 patients each year in the US (National Cancer Institute. Myelodysplastic Sundromes Treatment—for health professionals http://www.cancer.gov/types/myeloproliferative/hp/ myelodysplastic-treatment-pdq section/a112015 (2015); National Cancer Institute. Adult Acute Myeloid Leukemia Treatment—for health professionals (PDQ) http://www.cancer.gov/types/leukemia/hp/adult-aml-treatment-pdq2015 (2015)). The hallmarks of MDS include bone marrow failure from dysplastic maturation of hematopoietic stem cells (HSCs), clonal expansion of progenitors, and a propensity to transform to Acute Myeloid Leukemia (AML). Despite the introduction of new classes of drugs for the therapy of MDS (such as immunomodulators and hypomethylating agents), the only curative therapy is allogeneic stem cell transplant (SCT).

However, allogeneic SCT is associated with significant morbidity and mortality due to the significant toxicity of current preparative regimens, thus precluding the application of this treatment to a large number of patients, especially including the elderly. For AML, the standard therapy of 3 days of daunorubicin plus 7 days of cytarabine ("3+7") was devised over 30 years ago, and yet, although it varies by subtype, the overall 5-year survival is only 20-25% (Geiger, et al., Discovery medicine, 19(105):275-284 (2015); Jaffe, et al., Hematopathology, 1 ed. (2011)). Targeted therapies to date allow cellular differentiation and blast reduction, but not cure (Randhawa, et al., 56th American Society of Hematology Annual Meeting; Dec. 8, 2014; San Francisco 2014; Stein, et al., 56th American Society of Hematology Annual Meeting; Dec. 17, 2014; San Francisco 2014; Stein, et al., 56th American Society of Hematology Annual Meeting; Dec. 8, 2014; San Francicsio2014), Improved therapy is direly needed and the compositions and methods disclosed herein are well suited to the task.

For example, transient transfection-based multifactor adoptive chimeric antigen receptor T and NK (CAR-T and -NK) cell therapy for highly efficient treatment of MDS and AML, with minimal non-hematopoietic toxicity by specific elimination of myeloid cancer progenitor and stem cells can be carried out utilizing the disclosed compositions and methods.

CD33 and CD123 are two myeloid antigens that have been targeted by retroviral DNA CARs. CD33 is a transmembrane myeloid differentiation antigen expressed on at least a subset of AML blasts in most patients and on leukemia stem cells (Laszlo, et al., *Blood*, 123(4):554-561 (2014); Walter, et al., *Blood*, 119(26):6198-6208 (2012)). Highlighting the feasibility of CD33 in immunotherapy is Gemtuzumab Ozogamicin (GO), a CD33 monoclonal antibody conjugated to a cytotoxin, which showed modest improvement in relapse and survival rates among intermediate-risk AML patients in a meta-analysis (Hills, et al., *The Lancet Oncology*, 15(9):986-996 (2014)). Although GO was compromised due to inefficient drug toxicity, drug resistance and hepatotoxicity, the principle of targeting CD33 persists in the form of phase trials with a new cytotoxic conjugate that exhibits increased induction of apoptosis (Kung, et al., *Blood*, 122(8):1455-1463 (2013)). In addition, bi-specific CD33/CD3 T-cell engager (BiTE) and CD33/CD16 NK-cell engager (BIKE) antibodies are demonstrating good efficacy in preclinical models (Laszlo, et al., *Blood*, 123(4):554-561 (2014); Gleason, et al., *Blood*, 123(19):3016-26 (2014); Krupka, et al., Blood, 123(3):356-365 (2014); Singer, et al., Journal of Immunotherapy, 33(6):599-608 (2010)). Similarly, increased efficiency of CD33 CAR-T may overcome the limitations of the ozogamicin conjugate of GO, but potentially result in greater myelosuppressive toxicity.

CD123 is another promising and yet potentially controversial target (Gill, et al., *Blood*, 123(15):2343-2354 (2014); Mardiros, et al., *Blood*, 122(18):3138-3148 (2013); Tettamanti, et al., British Journal of Haematology, 161(3):389-401 (2013)). CD123, the alpha chain of the IL-3 receptor, is overexpressed in AML leukemia stem cells and is associated with their resistance to apoptosis, a higher proliferation rate and poor prognosis (Graf, et al., 72(2):89-106 (2004); Testa, et al., Blood, 100(8):2980-2988 (2002); Vergez, et al., Haematologica, 96(12):1792-8 (2011)). As with CD33, CD123 may also be expressed in the normal HSC and the multipotent progenitor (MPP), common myeloid progenitor (CMP), myeloid/erythroid progenitor (MEP), and granulocyte/monocyte progenitor (GMP) populations with CAR-T toxicity against these populations (Gill, et al., *Blood*, 123(15):2343-2354 (2014)). It is believed that personalizable CAR expression level in each effector cell and transient mRNA reprogramming will allow accurate titration of the effector cell load in order to reach maximal efficiency. This is because mRNA reprogramming of T and NK cells will increase the potential of killing. By generating mRNA-reprogrammed CART cells, CD33 and CD123 CARs can also be studied head-to-head at specified concentrations as well as in tandem or simultaneous administration, taking advantage of synergistic target toxicity of combination regimens.

Thus, particular embodiments include cell-based therapy following introduction of mRNA encoding CD33 CAR and/or CD123 CAR into T and/or NK cells to modulate myeloid lineage-specific targeting, and introduction of mRNAs encoding anti-apoptotic proteins like BCL-XL and/or proliferation-inducing cytokines like IL-2 to prolong T and NK cell lifespan by increasing their independence from paracrine stimulation and their metabolic stability in vivo. In some embodiments, modified lymphocyte persistence is optimized to induce maximal MDS/AML cytotoxicity with minimal off target killing.

Since CD33 and CD123 are expressed on an overlapping, but not identical, spectrum of MDS/AML stem and progenitor cells, the use of CARs targeting both antigens simultaneously can broaden the scope of treatable MDS/AML cell populations. Whereas 12% of AML are negative for CD33 and 22% are negative for CD123, only 4% of patients are negative for both (Ehninger, et al., *Blood Cancer Journal*, 4:e218 (2014)). Moreover, the use of both CARs can decrease the incidence of "escape clones" that loose expression of one of the antigens. While targeting both antigens concurrently with two distinct populations of reprogrammed cells might afford the above benefits, targeting both antigens with CARs expressed in the same cell may additionally invoke the advantage of cooperative binding.

In some embodiments, the CD33 CAR is a humanized CD33 CAR (GeneBank sequence AM402974.1, derived from gemtuzumab) with an IgG4 hinge (Kenderian, et al., *Leukemia: Official Journal of the Leukemia Society of America, Leukemia Research Fund, UK* (2015)). In addition, this CAR contains the 4-1BB and CD3 Zeta signaling domains. While this construct been shown to work well in T cells (Kenderian, et al., *Leukemia: Official Journal of the Leukemia Society of America, Leukemia Research Fund, UK* (2015)), it has not yet been explored in NK cells. In some embodiments, the CD123 CAR includes the CD123 scFv clone 32716 (Du, et al., Journal of Immunotherapy, 30(6): 607-613 (2007), with the CD8 hinge and the 4-1BB and CD3 Zeta signaling domains. Additionally or alternatively several different CD33 and CD123 CAR constructs with different linker domains and recognition epitopes have been published and can be utilized in the disclosed compositions and methods of transient transfection. Jonnalagadda et al. have indicated that the IgG4 hinge can be further improved by modification to remove a recognition site for Fc receptor binding (Jonnalagadda, et al., *Molecular Therapy: The Journal of the American Society of Gene Therapy,* 23(4):757-768 (2015)). Accordingly, in some embodiments, this mutated version is utilized. In some embodiments the CD8 hinge used for the CD19 CAR is utilized. For the CD123 CAR, the 26292 scFv clone can be substituted for the 32716 clone. Other CARs that target myeloid cells include ones developed against WT-1 (Zhao, et al., *Leukemia: Official Journal of the Leukemia Society of America, Leukemia Research Fund, UK* (2015)), LeY (Ritchie, et al., *Molecular Therapy: The Journal of the American Society of Gene Therapy,* 21(11):2122-9 (2013)) and Folate receptor beta (Lynn, et al., *Blood* (2015)).

The effector cell population chosen for reprogramming can be just as important to the treatment efficacy as the mRNAs used to reprogram them. Two complimentary lymphocyte populations with robust CAR mediated cytotoxicity are CD3-CD56+ NK cells and CD3+CD8+ T cells. Use of CD8+ T cells with CD4+ helper T cells leads to the increased presence of suppressive T-reg cells and dampened CD8+ T cell cytotoxicity. Since mRNA-reprogrammed CD8+ T cells are pre-activated so that they act directly on tumor cells without the need for activation in the lymph node, CD4+ T cell support is not essential. Taken together, multifactor mRNA electroporation of the appropriate lymphocyte population is a powerful technology that solves many of the problems of DNA reprogramming and can transform CAR-T cell therapy into an efficient and transient immune-mediated intervention to cure MDS/AML or as a preparative regimen for stem cell transplant.

d. Autoimmune Diseases

SLE affects approximately a quarter of a million people in the United States with over 100,000 hospitalizations per year, a 70% 10-year survival and a disproportionately higher prevalence in women and minorities (Lawrence, et al., *Arthritis and Rheumatism,* 41:778-799 (1998); Owings, et al., *Series 13, Data from the National Health Survey,* 1-157 (1999); Tsokos, et al., *The New England Journal of Medicine,* 365:2110-2121 (2011)). The disease is characterized by flares and remissions affecting multiple organs including nephritis, skin rashes, oral ulcers, arthritis, serositis, neurological defects, and blood cytopenias and thrombosis (Tsokos, et al., *The New England Journal of Medicine,* 365:2110-2121 (2011)). Major causes of death include renal impairment, infections, and vascular disease including atherosclerotic cardiovascular disease (Craft, et al., *Science Translational Medicine,* 3:73-79 (2011); Liu, et al., *Nature Medicine,* 18:871-882 (2012)).

While multiple defects in the immune system contribute to SLE, the disclosed compositions and methods can address at least two central factors involved: control of autoimmune B cell expansion and improvement of T cell functionality (Tsokos, et al., The New England Journal of Medicine, 365:2110-2121 (2011); Craft, et al., *Science Translational Medicine,* 3:73-79 (2011); Liu, et al., *Nature Medicine,* 18:871-882 (2012)). In the preclinical phase of SLE there is a clonal expansion of auto reactive B cells (Arbuckle, et al., *The New England Journal of Medicine,* 349:1526-1533 (2003)), which correlates with disease severity (Jacobi, et al., *PloS One,* 4:e5776, doi:10.1371/journal.pone.0005776 (2009)). Defective negative selection allows auto-reactive B cells to expand and differentiate into pathogenic memory and plasma cells (Cappione, et al., *The Journal of Clinical Investigation,* 115:3205-3216 (2005)). Auto-antibodies from these cells promote multi-organ failure through direct injury of target cells, deposition of inflammatory immune complexes and continued stimulation of auto-reactive B cells, which all contribute to further inflammation, fibrosis and pathologic tissue remodeling (Tsokos, et al., *The New England Journal of Medicine,* 365:2110-2121 (2011); Liu, et al., Nature Medicine, 18:871-882 (2012)). Even beyond auto-antibody production, B cells contribute to SLE pathogenesis by antigen presentation and signaling resulting in T cell over-activation and polarization and dendritic cell modulation (Anolik, et al., *Immunologic Research,* 45:144-158 (2009); Chan, et al., Immunological Reviews, 169:107-121 (1999); Park, et al., Expert Opinion on Therapeutic Targets, 9:431-445 (2005)). In fact, lupus prone mice with B cells incapable of secreting antibody retain some SLE symptoms, potentially due to persistent B cell promotion of T cell activation and cellular infiltration (Chan, et al., *The Journal of Experimental Medicine,* 189:1639-1648 (1999)). T cell impairment due to CD3ζ functional and genetic abnormalities (Martins, et al., *Genes and Immunity, doi:*10.1038/gene.2014.73 (2015); Moulton, et al., *Arthritis Research & Therapy,* 13:207 (2011)) increased apoptosis (Gergely, et al., *Arthritis and Rheumatism,* 46:175-190 (2002); Karpouzas, et al., *European Journal of Immunology,* 34:2489-2499 (2004)), and deficient IL-2 production (Crispin, et al., *Rheumatology,* 6:317-325 (2010); Crispin, et al., *Trends in Molecular Medicine,* 16:47-57 (2010); Juang, et al., *The Journal of Clinical Investigation,* 115:996-1005 (2005); Mizui, et al., Journal of Immunology, 193:2168-2177 (2014)) further contribute to the uncontrolled B cells and SLE pathogenesis.

Since aberrant B cell expansion, signaling, and auto-antibody production are universal components of SLE, the development of an adequate B cell depleting strategy is a high priority. Indeed, anti-CD20 antibodies showed initial promise in animal models (Ahuja, et al., *Journal of Immunology,* 179:3351-3361 (2007); Haas, et al., *Journal of Immunology,* 184:4789-4800 (2010); Wang, et al., *Journal of Immunology,* 192:3011-3020 (2014)), and small clinical case series (Looney, et al., *Arthritis and Rheumatism,* 50:2580-2589 (2004); Lu, et al., *Arthritis and Rheumatism,* 61:482-487 (2009); Ramos-Casals, et al., *Lupus,* 18:767-776 (2009)). However, in two larger, randomized clinical trials the anti-CD20 antibody, Rituximab, did not help patients with moderate to severe disease (Merrill, et al., *Arthritis and Rheumatism,* 62:222-233 (2010)). Possible causes can be attributed both to the fact that plasma cells, which no longer express CD20, are resistant to rituximab (Merrill, et al.,

*Arthritis and Rheumatism*, 62:222-233 (2010)) and to the ability of the spleen to protect B cells from being killed by antibody. The first possibility is supported by the finding of secreting plasma cells that are enriched in the kidneys of lupus-prone, NZB/W F1 mice (Espeli, et al., *Journal of the American Society of Nephrology: JASN*, 22: 296-305 (2011); Lacotte, et al., *Journal of Immunology*, 184:3937-3945 (2010); Starke, et al., *European Journal of Immunology*, 41:2107-2112 (2011)). The second fact is seen by persistent, protected splenic B cells found in both NZB/W F1 mice and MRL/MpJ-Faslpr mice, another lupus-prone mouse model, after treatment with rituximab (Ahuja, et al., *Journal of Immunology*, 179:3351-3361 (2007)).

The disclosed compositions and methods provide an efficient and transient immunosuppressive intervention for disease flares that is self-limiting and thereby absent during periods of disease quiescence. Here multifactor cell reprogramming by electroporation of T cells with three mRNAs in order to correct crucial functional defects related to SLE is provided.

The disclosed compositions and methods can be used to rapidly reprogram autologous T cells against B cells with multiple mRNAs concurrently, rather than a single mRNA or DNA. The approach is essentially transient and can be applied quickly at the specific time of disease development. It is not dependent on T cell proliferative potency, which is especially important for autologous therapy of patients with impaired immune systems. Reprogrammed T cells exhibit uniform mRNA expression and, since there is no clonal selection, are highly diverse. The obtained T cells are without risk of insertional mutagenesis and potential tumorigenicity, making safety a considerable additional advantage. The implementation of this approach will shift the clinical practice paradigm to a safe, rapid, flexible and controlled treatment format that is better suited for auto-immune diseases.

First, the introduction of CD19 CAR mRNA will kill B cells and also re-establish appropriate signaling through the CD3(chain and ZAP-70, as opposed to the altered FcRy chain and Syk pathway that is predominant in SLE T cell TCR signaling (Moulton, et al., *Arthritis Research & Therapy*, 13:207 (2011)). Since T cells from SLE patients and SLE-prone mice display abnormally high levels of apoptosis (Gergely, et al., *Arthritis and Rheumatism*, 46:175-190 (2002); Karpouzas, et al., *European Journal of Immunology*, 34:2489-2499 (2004)), therapeutic cells can be co-transfected (e.g., co-electroporated) an mRNA for anti-apoptotic BCL-XL to improve the viability of T cells. In addition, since T cells isolated from SLE patients have poor cytotoxic activity due to deficient IL-2 production (Crispin, et al., *Rheumatology*, 6:317-325 (2010); Crispin, et al., *Trends in Molecular Medicine*, 16:47-57 (2010); Juang, et al., *The Journal of Clinical Investigation*, 115:996-1005 (2005)), this defect can be corrected through reprogramming T cells with IL-2 mRNA. Even for T cells with appropriate CD3ζ signaling, low antigen and cytokine stimulation in vivo is an important factor that can undermine adoptive T cell efficacy (Gattinoni, et al., *The Journal of Experimental Medicine*, 202:907-912 (2005); Muranski, et al., *Oncology*, 3:668-681 (2006)). Co-introduction of BCL-XL and IL-2 mRNAs will not only compensate functional defects of T cells, but also increase their independence from paracrine stimulation and their metabolic stability in vivo. Since IL-2 protects lupus-prone mice from end-organ damage (Mizui, et al., *Journal of Immunology*, 193:2168-2177 (2014)), local delivery of IL-2 into SLE damaged organs like the kidney, lungs and skin from T cells reprogrammed with IL-2 mRNA might also be beneficial.

Whereas Rituximab efficacy is limited only to CD20 positive B cells, the CD19 CAR recognizes a wider range of B cell development that extends further into the plasma cell stage. This is hypothesized to be advantageous since anti-CD20 use in mouse SLE models, noted continued disease mediated by renal plasma cells (Espeli, et al., *Journal of the American Society of Nephrology: JASN*, 22: 296-305 (2011); Lacotte, et al., *Journal of Immunology*, 184:3937-3945 (2010); Starke, et al., *European Journal of Immunology*, 41:2107-2112 (2011); DiLillo, et al., *Journal of Immunology*, 180:361-371 (2008); Sekine, et al., *Journal of Immunology*, 172:3913-3921 (2004)). In addition, the mechanism of CAR T cell cytotoxicity is cardinally different from antibody-mediated killing, in that it is independent of macrophage and NK assistance, complement-mediated or direct antibody cytotoxicity. Furthermore, CAR T cells undergo active transport in tissues and organs, which can be especially important when secondary lymphoid organs are resistant to antibody (Ahuja, et al., *Journal of Immunology*, 179:3351-3361 (2007)).

In addition to CD19 CAR, Bcl-XL and IL-2 mRNAs can be utilized to confer upon the reprogrammed T cells resistance to apoptosis and increased homeostatic stability. In other compositions, CXCR5 mRNA can be utilized to confer upon the reprogrammed T cells the ability to localize to regions rich in B cells.

In some embodiments, a method of treating a subject with autoimmune disease includes administering the subject an effective amount of therapeutic immune cells to reduce one or more symptoms of the auto-immune disease.

B. Dedifferentiation, Transdifferentiation, Redifferenation

The methods can also be widely used for transient reprogramming of cells, for example, modulation of cell metabolism and differentiation, or for dedifferentiation of cells. An appropriate construct can be selected based on the target host cell type as well as the pathway or cellular activity to be manipulated, or the therapeutic application.

The disclosed methods are particularly useful in the field of stem cell therapy. In some embodiments, the methods are applied in the context of personalized therapy, for example, to generate iPS cells for introduction into a subject in need thereof. Constructs useful for de-differentiating cells, for example, converting adult, differentiated somatic cells into stem cells, can be constructed based on known genes, mRNAs, or other nucleotide or protein sequences. See, for example, Yu, et al., *Science*, 318:1917-1920 (2007) and Yamanaka, *Cell Prolif.*, 41:51-56 (2008), which describes induced pluripotent stem (iPS) cells obtained from differentiated primary cells by ectopic expression of combinations of transcription factors such as OCT4, SOX2, NANOG, and LIN28, or OCT3/4, SOX2, KLF4 and c-MYC.

Exemplary genomic, mRNA (cDNA), and protein sequences for OCT4 are known in the art, see, for example, (OCT4) POU5F1 POU class 5 homeobox 1 [*Homo sapiens*] Gene ID: 5460, which provides mRNA (cDNA) sequences Genbank accession no. NM_001173531.1 entitled *Homo sapiens* POU class 5 homeobox 1 (POU5F1), transcript variant 3, mRNA; Genbank accession no. NM_002701.4 entitled *Homo sapiens* POU class 5 homeobox 1 (POU5F1) transcript variant 1, mRNA; and Genbank accession no. NM_203289.4 entitled *Homo sapiens* POU class 5 homeobox 1 (POU5F1), transcript variant 2, mRNA. Exemplary genomic, mRNA (eDNA), and protein sequences for SOX2 are also known in the art, see, for example, SOX2 SRY (sex determining region Y)-box 2 [*Homo sapiens*], Gene ID: 6657, which provides mRNA (cDNA) sequence Genbank Accession no. NM_003106.2 entitled mRNA sequence *Homo sapiens* SRY (sex determining region Y)-box 2 (SOX2), mRNA. Exemplary genomic, mRNA (cDNA), and protein sequences for NANOG are also known in the art, see for example NANOG Nanog homeobox [*Homo sapiens*], Gene ID: 79923, which provides the mRNA (cDNA) sequence Genbank accession no. NM_024865.2 entitled *Homo sapiens* Nanog homeobox (NANOG), mRNA. Exemplary genomic, mRNA (cDNA), and protein sequences for LIN28 are also known in the art, see for example LIN28A lin-28 homolog A (*C. elegans*) [*Homo sapiens*], Gene ID: 79727, which provides the mRNA (cDNA) sequence Genbank accession no. NM_024674.4 entitled *Homo sapiens* lin-28 homolog A (*C. elegans*) (LIN28A), mRNA. Exemplary genomic, mRNA (cDNA), and protein sequences for KLF4 are known in the art, see, for example, KLF4 Kruppel-like factor 4 (gut) [*Homo sapiens*], Gene ID: 9314, which provides the mRNA (cDNA) sequence Genbank accession no. NM_004235.4 entitled *Homo sapiens* Kruppel-like factor 4 (gut) (KLF4), mRNA. mRNA sequences for MYC are also known in the art, see for example MYC v-myc myelocytomatosis viral oncogene homolog (avian) [*Homo sapiens*], Gene ID: 4609, which provides the mRNA (cDNA) sequence Genbank accession no. NM_002467.4 entitled *Homo sapiens* v-myc myelocytomatosis viral oncogene homolog (avian) (MYC), mRNA.

Following transfection with one or more RNAs, the cells can be maintained or expanded in culture. Methods for culturing both transfected and non-transfected cells are known in the art, and may include providing additional reagents or supplements to enhance viability and/or growth, for example, growth factors or a feeder layer of cells.

Although transfection using the disclosed mRNAs is transient, once the cells have been induced to de-differentiate, the de-differentiated cells can be maintained in their induced state using tissue culture conditions that are known in the art. For examples, differentiated somatic cells such as fibroblasts that are induced to de-differentiate into iPS cells can be maintained as iPS cells using methods consistent with culturing undifferentiated iPS cells.

The methods can also be widely used for re-differentiating or reprogramming of cells, for example, to produce iPS cells that can be further modulated to form hematopoietic stem cells, mesenchymal stem cells, epithelial stem cells, and muscle satellite cells, or differentiated cells of human tissues, including, but not limited to, red blood cells, white blood cells including lymphocytes, platelets, stromal cells, fat cells, bone cells including osteoclasts, epithelial tissue including skin cells, muscle tissue including smooth muscle, skeletal muscle, and cardiac muscle, vascular tissue including endothelial cells, liver tissue including hepatocytes, and nervous tissue including neurons. Methods of inducing differentiation of iPS cells into various differentiated cells types, including, but not limited to, cardiomyocytes, hematopoietic stem cells, bone cells such as, osteoclasts, hepatocytes, retinal cells, and neurons, are known in the art (Song at al., *Cell Res.*, 19(11):1233-42 (2009), Lamba at al, *PLoS One,* 5(1):e8763 (2010), Gai et al., *Cell Biol Int.* 200933 (11): 1184-93 (2009). Grigoriadis et al., *Blood,* 115(14):2769-76 (2010)). Stem cells including, but not limited to, isolated embryonic stem cells, hematopoietic stem cells, and induced pluripotent stem cells can be induced to differentiate by transient transfection with RNAs that induce differentiation. Additionally, or alternatively, cells can be re-differentiated by culturing the cells under cell type-specific conditions. For example, iPS cells can be maintained on CF-1 feeders and subsequently adapted to feeder-free conditions. iPS cells can be induced to form differentiated retinal cells by culturing the cells in the presences of noggin, Dkk-1, and IGF-1 (see for example Lamba at al, *PLoS One,* 5(1):e8763 (2010)).

In some embodiments, cells are re-programmed by transient transfection. For example, mRNA from transcription factors such as FoxP3 can be introduced into lymphocytes to increase the formation of regulatory T cells. FoxP3 (forkhead box P3) is a master regulator of development and function of regulatory T cells. Exemplary genomic, mRNA (cDNA), and protein sequences for FoxP3 are known in the art, see, for example Gene ID: 50943, which provides the mRNA (cDNA) sequences Genbank accession no. NM_014009.3 entitled *Homo sapiens* forkhead box P3 (FOXP3), transcript variant 1, mRNA; and Genbank accession no. Nm_001114377.1 entitled *Homo sapiens* forkhead box P3 (FOXP3), transcript variant 2, mRNA.

iPS cells can be monitored and selected by identification of specific antigens, such as Nanog, Sox2, SSEA-3, SSEA-4, TRA-1-60, TRA-1-81, Oct 3/4 and alkaline phosphatase, and purified by different methods including magnetic column separation and flow cytometry.

In some embodiments, one or more RNAs are used in combination to induce transdifferentiation from one type of cell to another, such as T cells or heniatopoietic precursors or other blood cells into T regs, or into erythroid cells or megakaryocytes.

C. Effective Amounts, Dosages, and Treatment Regimens

RNAs prepared according to the disclosed compositions and methods, and cells transfected therewith can be administered to a patient in need thereof in a pharmaceutical composition. Pharmaceutical compositions containing nucleic acids or cells may be for systemic or local administration, such as intratumoral. Dosage forms for administration by parenteral (intramuscular (IM), intraperitoneal (IP), intravenous (IV), intra-arterial, intrathecal or subcutaneous injection (SC)), routes of administration can be formulated. In some embodiments, the nucleic acids or cells are delivered by local injection preferably into, at, or near the tumor itself or the tumor's microenvironment. In a particular embodiment the composition, particularly those including transfected cells, is injected directly into the tumor. The compositions can be formulated for and delivered via catheter into the tumor resection cavity through convection-enhanced delivery (CED).

1. Formulations

The term "pharmaceutically acceptable" means a non-toxic material that does not interfere with the effectiveness of the biological activity of the active ingredients. The term "pharmaceutically-acceptable carrier" means one or more compatible solid or liquid fillers, diluents or encapsulating substances which are suitable for administration to a human or other vertebrate animal. The term "carrier" refers to an organic or inorganic ingredient, natural or synthetic, with which the active ingredient is combined to facilitate the application. Pharmaceutical compositions may be formulated in a conventional manner using one or more physiologically acceptable carriers including excipients and auxiliaries which facilitate processing of the active compounds into preparations which can be used pharmaceutically. The compositions may be administered in combination with one or more physiologically or pharmaceutically acceptable carriers, thickening agents, co-solvents, adhesives, antioxidants, buffers, viscosity and absorption enhancing agents and agents capable of adjusting osmolarity of the formulation. Proper formulation is dependent upon the route of administration chosen. If desired, the compositions may also contain minor amounts of nontoxic auxiliary substances such as wetting or emulsifying agents, dyes, pH buffering agents, or preservatives.

In a preferred embodiment, compositions are administered in an aqueous solution, by parenteral injection or infusion. The formulation may also be in the form of a suspension or emulsion. In general, pharmaceutical compositions are provided including effective amounts of the composition, and optionally include pharmaceutically acceptable diluents, preservatives, solubilizers, emulsifiers, adjuvants and/or carriers. Such compositions include diluents such as sterile water, buffered saline of various buffer content (e.g., Tris-HCl, acetate, phosphate), pH and ionic strength; and optionally, additives such as antioxidants (e.g., ascorbic acid, sodium metabisulfite), and preservatives and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate.

The formulations should not include agents could inactivate or kill the RNAs or therapeutic cells. In some embodiments, the pharmaceutical composition for cells is a saline solution, preferably a buffered saline solution phosphate buffered saline or sterile saline, or tissue culture medium.

2. Effective Amounts

As generally used herein, an "effective amount" is that amount which is able to induce a desired result in a transfected cell or a treated subject.

For example, an effective amount of RNA can be an amount effective to achieve a desired molecular, biochemical, or histological results in a cell transfected therewith. If the RNA encodes a polypeptide, the effective amount of RNA is typically sufficient that the polypeptide can be detected in the cell. If the polypeptide is a surface or transmembrane protein such as CAR, the amount is preferably sufficient for the polypeptide to be detected on the surface of the cell. If the RNA is an inhibitory RNA, the effective amount of RNA should be sufficient to reduce expression of its target in transfected cells relative to untransfected cells. RNA should also be transfected into cells in an amount effective to make the desired change in the cell. For example, if the cell is transfected with a CAR construct, the cell should express sufficient CAR protein on the surface of the cell to engage and preferable kill its target cell. If the cell is transfected with a functional or inhibitory RNA that reduces expression of an inhibitory molecule within the cell, the RNA should be transfected into the cell in a sufficient amount to reduce inhibitory signaling in the cell relative to an untransfected cell. If the cell is transfected with an RNA that encodes a factor that improves cellular metabolism including, but not limited to anti-apoptotic factors and pro-viability factors, the RNA should be transfected in an effective amount to improve the desire metabolic readout (e.g., e.g., cell survival, longevity, etc.), relative to untransfected cells. If the cell is transfected with an RNA encoding a de-differentiation factor, the cells should be transfected with an effective amount to change the somatic cells to a less differentiated state. Preferred dosages of RNA for transfecting cells in vitro (or ex vivo) can be, for example, can vary from 1 to 3000 ug/ml; in some embodiments. Cell concentrations can vary from 1 to 500 million per ml.

When RNA or transfected cells are administered to a subject, the desired results will depend on the disease or condition to be treated. The precise dosage will vary according to a variety of factors such as subject-dependent variables (e.g., age, immune system health, etc.), the disease, and the treatment being effected. For example, an effective amount of RNA or cell transfected therewith can be an amount sufficient to reduce or improve one or more symptoms of disease or condition to be treated. Therapeutically effective amounts of the composition, particularly those including transfected cells, used in the treatment of cancer will generally kill tumor cells or reduce proliferation or metastasis of the tumor cells. Symptoms of cancer may be physical, such as tumor burden, or biological such as proliferation of cancer cells. For example, the transfected cells can be administered in an amount effective to increase cancer cell death, improve survival of a subject with cancer, or a combination thereof. Although the actual effective amounts of the composition can vary according to factors including the specific composition administered, the particular composition formulated, the mode of administration, and the age, weight, condition of the subject being treated, as well as the route of administration and the disease or disorder, exemplary dosage ranges for therapeutic cells can be, for example, from $10^1$ to $10^{12}$ T cells per patient per day.

An effective amount of the composition can be compared to a control. Suitable controls are known in the art. A typical control can be a comparison of a condition or symptom of a subject prior to and after administration of the treatment. The condition or symptom can be a biochemical, molecular, physiological, or pathological readout. In other embodiments, the control is a matched subject that is administered a different therapeutic agent. Accordingly, the compositions disclosed here can be compared to other art recognized treatments for the disease or condition to be treated. If the treatment is a co-therapy, for example a combination of transfected cells and a pro-apoptotic agent, the combination to the two (or more) elements of the co-therapy, and be (1) greater than administration of one or both the elements individually, (2) the additive effect of administering both of the elements individually, or (3) more than the additive effect of administering both of the elements individually.

3. Treatment Regimens

Because RNA does not typically integrate into the genome and typically degrades over hours, days, or weeks, the effect on cells transfected with RNA can be transient (e.g., non-permanent), For example, a cell transfected with RNA encoding a polypeptide such as a CAR may express the CAR on its surface for hours, days, or weeks, until the RNA has degraded and the translated protein has been metabolized. Accordingly, in some embodiments, the same cells are transfected with RNA multiple times: hours, days, or weeks apart. Additionally, in some therapeutic applications, a subject can receive multiple administrations of treated cells. For example, subjects can be administered transfected cells one, two, three, four, five, six, seven times a week; or one, two, three, four, five, six, seven or eight times a month. In some embodiments, the composition is administered every two, three, or four days, or on average about 1 to about 3 times about week.

4. Combination Therapies

The RNAs and cells transfected therewith can be administered alone or in any combination and further in combination with one or more additional active agents. In all cases, the combination of agents can be part of the same admixture, or administered as separate compositions. In some embodiments, the separate compositions are administered through the same route of administration. In other embodiments, the separate compositions are administered through different routes of administration.

In some embodiments, an additional agent such a pro-apoptotic agent is administered to the subject prior to administration of the cells to the subject. The additional agent can be administered to the subject, for example, 1, 2, 3, 4, 5, 6, 8, 10, 12, 18, or 24 hours, or 1, 2, 3, 4, 5, 6, or 7 days, or any combination thereof prior to administration of the cells to the subject.

In some embodiments, the cells are administered to the subject prior to administration of an additional agent to the subject. The cells can be administered to the subject, for example, 1, 2, 3, 4, 5, 6, 8, 10, 12, 18, or 24 hours, or 1, 2, 3, 4, 5, 6, or 7 days, or any combination thereof prior to administration of the additional agent to the subject.

Preferred combinations include therapeutic cells and pro-apoptotic cells such as BH3 mimetics discussed above. In some embodiments, the cells are administered to a subject in need thereof in combination with one or more additional therapeutic agents selected based on the condition, disorder or disease to be treated. A description of the various classes of suitable pharmacological agents and drugs may be found in Goodman and Gilman, *The Pharmacological Basis of Therapeutics*, (11th Ed., McGraw-Hill Publishing Co.) (2005).

Additional therapeutic agents include conventional cancer therapeutics such as chemotherapeutic agents, cytokines, chemokines, and radiation therapy. The majority of chemotherapeutic drugs can be divided into: alkylating agents, antimetabolites, anthracyclines, plant alkaloids, topoisomerase inhibitors, and other antitumour agents. All of these drugs affect cell division or DNA synthesis and function in some way. Additional therapeutics include monoclonal antibodies and the tyrosine kinase inhibitors e.g., imatinib mesylate (GLEEVEC® or GLIVEC®), which directly targets a molecular abnormality in certain types of cancer (chronic myelogenous leukemia, gastrointestinal stromal tumors).

Representative chemotherapeutic agents include, but are not limited to, amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epipodophyllotoxins, epirubicin, etoposide, etoposide phosphate, fludarabine, fluorouracil, gemcitabine, hydroxycarbamide, idarubicin, ifosfamide, irinotecan, leucovorin, liposomal doxorubicin, liposomal daunorubicin lomustine, mechlorethamine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, teniposi de, tegafur-uracil, temozolomide, teniposide, thiotepa, tioguanine, topotecan, treosulfan, vinblastine, vincristine, vindesine, vinorelbine, taxol and derivatives thereof, trastuzumab (HERCEPTIN®), cetuximab, and rituximab (RITUXAN® or MABTHERA®), bevacizumab (AVASTIN®), and combinations thereof. Representative pro-apoptotic agents include, but are not limited to, fludarabinetaurosporine, cycloheximide, actinomycin D, lactosylceramide, 15d-PGJ(2), and combinations thereof.

Preferred chemotherapeutics will affect tumors or cancer cells, without diminishing the activity of T cells. For example, in a preferred embodiment, the additional therapeutic agent inhibits proliferation of cancer cells.

The compositions can be administered with an antibody or antigen binding fragment thereof specific for growth factor receptors or tumor specific antigens. Representative growth factors receptors include, but are not limited to, epidermal growth factor receptor (EGFR; HER1); c-erbB2 (HER2); c-erbB3 (HER3); c-erbB4 (HER4); insulin receptor; insulin-like growth factor receptor 1 (IGF-1R); insulin-like growth factor receptor 2/Mannose-6-phosphate receptor (IGF-II RIM-6-P receptor); insulin receptor related kinase (IRRK); platelet-derived growth factor receptor (PDGFR); colony-stimulating factor-1receptor (CSF-1R) (c-Fms); steel receptor (c-Kit); Flk2/Flt3; fibroblast growth factor receptor 1 (Flg/Cek1); fibroblast growth factor receptor 2 (Bek/Cek3/K-Sam); Fibroblast growth factor receptor 3; Fibroblast growth factor eceptor 4; nerve growth factor receptor (NGFR) (TrkA); BDNF receptor (TrkB); NT-3-receptor (TrkC); vascular endothelial growth factor receptor 1 (Flt1); vascular endothelial growth factor receptor 2/Flk1/KDR; hepatocyte growth factor receptor (HGF-R/Met); Eph; Eck; Eek; Cek4/Mek4/HEK; Cek5; Elk/Cek6; Cek7; Sek/Cek8; Cek9; Cek10; HEK11; 9 Ror1; Ror2; Ret; Axl; RYK; DDR; and Tie.

D. Diseases to be Treated

Cells prepared according the disclosed methods are particularly useful in the context of cancer, including tumor therapy. In a mature animal, a balance usually is maintained between cell renewal and cell death in most organs and tissues. The various types of mature cells in the body have a given life span; as these cells die, new cells are generated by the proliferation and differentiation of various types of stem cells. Under normal circumstances, the production of new cells is so regulated that the numbers of any particular type of cell remain constant. Occasionally, though, cells arise that are no longer responsive to normal growth-control mechanisms. These cells give rise to clones of cells that can expand to a considerable size, producing a tumor or neoplasm. A tumor that is not capable of indefinite growth and does not invade the healthy surrounding tissue extensively is benign. A tumor that continues to grow and becomes progressively invasive is malignant. The term cancer refers specifically to a malignant tumor. In addition to uncontrolled growth, malignant tumors can exhibit metastasis. In this process, small clusters of cancerous cells dislodge from a tumor, invade the blood or lymphatic vessels, and are carried to other tissues, where they continue to proliferate. In this way a primary tumor at one site can give rise to a secondary tumor at another site.

The compositions and methods described herein are useful for treating subjects having benign or malignant tumors by delaying or inhibiting the growth of a tumor in a subject, reducing the growth or size of the tumor, inhibiting or reducing metastasis of the tumor, and/or inhibiting or reducing symptoms associated with tumor development or growth.

Malignant tumors which may be treated are classified herein according to the embryonic origin of the tissue from which the tumor is derived. Carcinomas are tumors arising from endodermal or ectodermal tissues such as skin or the epithelial lining of internal organs and glands. The disclosed compositions are particularly effective in treating carcinomas. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

The types of cancer that can be treated with the provided compositions and methods include, but are not limited to, vascular cancers such as multiple myeloma, adenocarcinomas and sarcomas, of bone, bladder, brain, breast, cervical, colo-rectal, esophageal, kidney, liver, lung, nasopharangeal, pancreatic, prostate, skin, stomach, and uterine. In some embodiments, the disclosed compositions are used to treat multiple cancer types concurrently. The compositions can also be used to treat metastases or tumors at multiple locations.

In some embodiments, cells are reprogrammed to modulate the immune response. The methods are also useful for organ regeneration, and for restoration or supplementation of the immune system. For example, cells at different stages of differentiation such as iPS cells, hematopoietic stem cells, multipotent cells or unipotent cells such as precursor cells, for example, epithelial precursor cells, and others can be administered intravenously or by local surgery. The methods can be used in combination with other conventional methods, such as a prescription medication regime, surgery, hormone therapy, chemotherapy and/or radiotherapy.

The compositions and methods can also be used for cell replacement or supplementation, or stem cell therapy. The methods can be used to generate cells which may be useful in the treatment of a variety of diseases and disorders, including, but not limited to, neurodegenerative diseases such as Parkinson's, Alzheimer disease, and multiple sclerosis. For example, lymphocytes can be reprogrammed into regulatory T cells which can be administered to a patient in need thereof to increase or transfer immune tolerance, especially self-tolerance. The induction or administration of reprogrammed or dedifferentiated cells, including Foxp3 positive T cells, may be useful in reducing autoimmune responses such graft rejection, and/or reducing, inhibiting or mitigating one or more symptoms of an autoimmune diseases or disorder such as diabetes, multiple sclerosis, asthma, inflammatory bowel disease, thyroiditis, renal disease, rheumatoid arthritis, systemic lupus erythematosus, alopecia areata, anklosing spondylitis, antiphospholipid syndrome, autoimmune Addison's disease, autoimmune hemolytic anemia, autoimmune hepatitis, autoimmune inner ear disease, autoimmune lymphoproliferative syndrome (ALPS), autoimmune thrombocytopenic purpura (ATP), Behcet's disease, bullous pemphigoid, cardiomyopathy, celiac sprue-dermatitis, chronic fatigue syndrome immune deficiency syndrome (CFIDS), chronic inflammatory demyelinating polyneuropathy, cicatricial pemphigoid, cold agglutinin disease, Crest syndrome, Crohn's disease, Dego's disease, dermatomyositis, dermatomyositis—juvenile, discoid lupus, essential mixed cryoglobulinemia, fibromyalgia—fibromyositis, Grave's disease, Guillain-Barre, Hashimoto's thyroiditis, idiopathic pulmonary fibrosis, idiopathic thrombocytopenia purpura (ITP), IgA nephropathy, insulin dependent diabetes (Type I), juvenile arthritis, Meniere's disease, mixed connective tissue disease, multiple sclerosis, myasthenia gravis, pemphigus vulgaris, pernicious anemia, polyarteritis *nodosa*, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiff-man syndrome, Takayasu arteritis, temporal arteritis/giant cell arteritis, ulcerative colitis, uveitis, vasculitis, vitiligo, and Wegener's granulomatosis.

V. Kits

In one embodiment, a kit includes RNAs, cells, and a means for transfecting the RNA into the cells. The RNAs can be lyophilized or in solution. Kits may optionally include other materials such as cell culture reagents. In an alternative embodiment, a kit provides re-differentiated, dedifferentiated, or reprogrammed cells prepared according to the disclosed methods, and stored and/or shipped refrigerated or frozen for later use. Cells are typically stored in a solution maintaining viability. Kits containing cells should be stored or shipped using a method consistent with viability such as in a cooler containing dry ice so that cells are maintained below 4° C., and preferably below −20° C.

The kits optionally include one or more of the following: bioactive agents, media, excipients and one or more of: a syringe, a needle, thread, gauze, a bandage, a disinfectant, an antibiotic, a local anesthetic, an analgesic agent, surgical thread, scissors, a scalpel, a sterile fluid, and a sterile vessel. Components of the kit may be packaged individually and can be sterile. The kits are generally provided in a container, e.g., a plastic, cardboard, or metal container suitable for commercial sale. Any of the kits can include instructions for use.

The present invention will be further understood by the following non-limiting examples.

EXAMPLES

Material and Methods:

Cells

*Escherichia coli* cells were grown on LB broth with 100 µg/ml ampicillin

Mouse: EML cells were grown on Iscove's Medium (Gibco) supplemented with 20% Donor Horse serum with BHK conditioned media and non-essential amino acids.

Human Cell Lines

Hela and Human Non-Hodgkin's B cell Lymphoma line CRL2261 cells were grown on DMEM (GIBCO) supplemented with 10% fetal bovine serum (FBS), glutamate. Bjab, BL2, Palo, NB4, Jurkat cells were grown in RPMI Medium supplemented with 10% FBS.

Primary Human Cells

Activated B cells were received by cultivating mononuclear cells (MNC) in the presence of CD40 ligand activation as described by Schultze, et al., *Proc. Natl. Acad. Sci.,* 92:8200-8204 (1995). MNCs were washed and plated on pre-formed layer of previously irradiated (96Gy) 3T3-CD40L on IMDM (Gibco), with 10% human serum (Gemini Bio-Products, CA, USA), 200 U/ml IL-4 and in the presence of Cyclosporin A (Sigma). The cultured B-cells were transferred in new pre-layered plates and re-stimulated every 3-4 days. Cultures were kept up to 21 days. The percentage of CD19-positive cells was 85-95% after day 10 of cultivation.

Populations of activated CD3+ cells were obtained from MNCs using XCYTE DYNABEADS® (Xcyte Therapies) with covalently attached anti-CD3 and anti-CD28 monoclonal antibodies. MNCs were resuspended at $10 \times 10^6$/ml in DPBS, 0.5% HA and XCYTE DYNABEADS® (50 µl per ml of sample) were added. The mixture then was incubated 30 min in a refrigerator with rotation. The positive (CD3+) fraction was isolated by Dynal MPC and cultivated 7-10 days in IMDM (Gibco), with 5% human serum (Gemini Bio-Products), in the presence of 100 IU/ml Interleukin-2 (PeproTech, NJ, USA). The beads were removed from the culture before electroporation.

CD8+ cells were isolated from CD3+ cells by Cd8+ T Cell Isolation Kit II (Miltenyi Biotec, Germany) according to the manufacturer's recommendations. The purity of selected CD8+ cells was 96%.

Reagents: Yeast tRNA and DNA ladders were purchased from Invitrogen, 8-azaadenosine-5'-triphosphate and cordiocipin—from TrfiLink Biotechnologies, polyadenilic acid—from MP Biomedicals.

RNA Synthesis mRNA constructs based on the Pontelina plumata green fluorescent protein ("GFP") sequence of pmaxGFP plasmid (Amaxa Biosystems) were produced in vitro using T7 RNA polymerase (RNAP). Forward primer contained T7 RNA P promoter and anchoring sequence to the proximal part of the GFP expression cassette. Reverse primer with anchoring sequence to distal part of GFP expression cassette contained a stretch of 100 oligo-dT. mRNA synthesis was provided with mMESSAGE mMASHINE® kit (Ambion), using the procedure recommended by the manufacturer. In some cases the product was additionally polyadenylated using the reagent of the same kit. The final product was treated with DNaseI and purified by Ambion MEGAclear kit or by LiCI precipitation.

Transfections

Electroporation was performed using an Amaxa NUCLEOFECTOR™-II (Amaxa Biosystems, Cologne, Germany) in accordance with manufacturer recommendations. Jurkat and B cell lines were transfected using NUCLEOFECTOR™-II solution V and the set of recommended regimes for electroporation. EML cells were transfected using solutions V, T and R and different regimes of electroporation. T lymphocytes were transfected using T cell NUCLEOFECTOR™-II solution and different regimes of electroporation. Alternative methods of nucleic acids delivery were also used: cationic liposome mediated transfection was performed using LIPOFECTIN® or LIPOFECTAMIN® (Invitrogen). Electroporation was also performed with the ECM 830 (BTX) (Harvard Instruments, Boston, Mass.) or the Gene Pulser II (BioRad, Denver, Colo.), Multiporator (Eppendorf, Hamburg Germany). All procedures were performed as directed by the manufacturers. pmaxGFP plasmid DNA (Amaxa Biosystems) was used as the DNA control. The efficiency of transfection (ET) was determined 18h after transfection by fluorescence activated cell sorting (FACS). In some experiments transfectants were further analyzed each 24h until GFP could not longer be detected. Cell viability was determined by trypan blue dye exclusion.

Flow Cytometry

Flow cytometry was performed using the fluorescent activated cell sorting (FACS®) assay. Flow cytometry was performed on cell subpopulations was performed at the Yale Cancer Center Flow Cytometry Shared Resource, using a FACS® Calibur flow cytometer (Becton-Dickinson, San Jose, Calif.) equipped with 488 nm laser and the standard filter setup. Fluorescence signals were collected on a logarithmic scale. A minimum of ten thousand cells were interrogated for each sample. Analysis of data was performed using FlowJo software (Tree Star, Inc., San Carlos, Calif.). The expression efficiency was calculated as the difference between the geometric mean of fluorescence of the transfectants and control (mock transfected) cells. Mouse anti-human CD4 FITC (anti-CD4 antibody, fluorescein isothiocyanate conjugated), CD8 PE (anti CD8 antibody, phycoerythrin conjugated, CD19PE (anti-CD19, PE conjugated), and CD3 PerCP-Cy5.5 (anti-CD3 antibody, peridinin chlorophyll protein [PerCP]-Cy5.5 conjugated), were purchased from BD Biosciences Pharmingen (San Diego, Calif.), Streptavidin-PerCP (streptavidin, PerCP conjugated)—from BD Immunocytometry Systems (Philadelphia, Pa.), and Biotin-conjugated goat anti-mouse IgG was from Jackson ImmunoResearch Laboratories (West Grove, Pa.). Cells were stained according to the manufacturer's recommendation.

Electrophoresis:

DNA samples were run in 1% agarose in Tris-acetate buffer, 2 v/cm RNA samples were run in 1% agarose in MOPS-formaldehyde buffer, 2 v/cm, using RNA Millenium marker (Invitrogen) as size standard.

Cytotoxicity Assay

The cytotoxic activity of electroporated CD3+CD8+ cells were evaluated by a standard $^{51}$Cr release method. CRL2261 and lymphoblastoid B cells were used as targets. The target B cells, CRL2261 and K562 cells were labeled with 0.25 mCi of $^{51}$ Cr-sodium chromate (MP Biomedicals, Inc., Irvine, Calif., USA) for 1 hour, extensively washed and seeded at a density of 10×104 in V-bottom 96 well microplates. Transfected CD8+ CD3+ effector (E) cells were suspended in IMDM (Gibco), 10% FBS medium and added to target cells at different E:T ratios. The plates were incubated at 37° C. for 4h, and aliquots of each sample were harvested for gamma counting in order to assess 51Cr release. Calculations were carried out in triplicate. Specific lysis was calculated as lysis %=

$$\frac{\text{Observed release}(c.p.m.) - \text{spontaneous release}(c.p.m.)}{\text{Total release}(c.p.m.) - \text{spontaneous release}(c.p.m.)} \times 100$$

where c.p.m. is the count/min released by targets incubated with effector cells. Spontaneous release was determined from wells to which 100 μl of complete medium was added instead of effector cells. Total releasable radioactivity was measured after treating the targets with 100 μl of 1% Tritobx100.

Xenograft Tumor Model

On day 0, 6 week-old female NOD/Scid (NOD/LtSz-Prkdc Scid/J) mice (Jackson Laboratory) were injected in the peritoneum with $3 \times 10^6$ ffLuc+Daudi cells. On days 2 and 3 tumor engraftment was evaluated by biophotonic imaging. Mice with progressively growing tumors were segregated into 3 treatment groups (8 mice per group) receiving additional intraperitoneal (ip) injection of RPMI medium (medium control) (Group 1) or $5 \times 10^6$ CTLs: mock transfected CTLs (Group 2) or anti-CD19 CAR mRNA transfected CTLs (Group 3).

Biophotonic Tumor Imaging

Anesthetized mice were imaged using Xenogen IVIS 100 system beginning 15 minutes after ip injection of 150 ml of a freshly thawed aqueous solution of D-luciferin (Xenogen, Alameda, Calif.). Each animal was serially imaged in an anterior-posterior orientation at the same relative time point after D-luciferin injection. Photons emitted from ffLuc Daudi xenografts were quantified using the software program Living Image (Xenogen), and the bioluminescence signal was measured as total photon flux normalized for exposure time and surface area and expressed in units of photons (p) per second per cm2 per steradian (sr). For anatomic localization, a pseudocolor image representing light intensity (blue, least intense; red, most intense) was superimposed over a digital grayscale body-surface reference image.

Statistical Methods to Analyze Biophotonic Data

To measure the differences between mouse treatment groups, evaluating tumor biophotonic signal over time was considered. The signals were normalized for the initial values on day 3 after tumor injection (also the day of first CTLs injection) which was taken as 1 for each mouse. Data obtained for each group were presented as geometrical mean+/− geometrical SD.

The present invention will be further understood by reference to the following non-limiting examples.

Example 1

RNA Transfection in EML Cells

EML cells are a murine cell line that grows in suspension and has the capacity to differentiate into cells of several hematopoietic lineage in vitro. These cells would be of considerable interest for manipulation in vitro, but, unfortunately, they are relatively resistant to standard transfection methods. EML cells were therefore used as a model for exploring various DNA and RNA transfection methods with difficult cells. For convenience of assaying, a DNA plasmid expressing green fluorescent protein (GFP) was used. The following transfection methods were tested: LIPOFECTIN® and LIPOFECTAMIN® lipofection, electroporation using square wave BTX ECM 830 apparatus or BioRad Gene Pulser II, exponential diminishing wave electroporation using Eppendorf Multiporator, and also Amaxa nucleofector. All methods were optimized according to the recommendations of the manufacturers. The Amaxa nucleofection protocol gave the highest efficiency of transfection. The Amaxa procedure was optimized using different combinations of one of three solutions (V, R, and T) and 8 programs of electroporation.

The best result that could be obtained for plasmid DNA transfection was that 12% of the initial cells showing GFP expression, with slightly less than half the initial cells remaining viable after electroporation. Therefore 25% of the surviving cells expressed GFP under these conditions. Further optimization using the programs recommended by the manufacturer was not effective.

The DNA template was designed from the GFP sequence of the pmaxGFP plasmid. To avoid aberrant transcription of PCR-made DNA templates, a T7 promoter and 3' transcription terminator was introduced in the DNA template directly during PCR. The forward PCR primer contained a T7 RNA polymerase promoter and an anchoring sequence from the 5' untranslated region (5'UTR) of the GFP gene. The reverse primer needed a structure that allowed the correct transcriptional termination (FIGS. 1, 2A). The PCR product was used for in vitro transcription by T7 RNA polymerase. The mRNA was purified and delivered into mouse EML cells by nucleofection. PmaxGFP plasmid DNA was used as a control.

Effect of the 5' and 3' UTRs on Expression

GFP mRNA with short UTRs: 6 nucleotides upstream of ATG codon and 35 nucleotides downstream of stop codon, was virtually unexpressed. mRNA which included 44 nucleotides upstream of the ATG codon, and 113 nucleotides downstream of the stop codon, were efficiently expressed (Table 1).

TABLE 1

Transfectability of the GFP mRNA constructs

| Coordinates of ends of DNA matrix for mRNA synthesis | | |
|---|---|---|
| Left end Distance from first GFP codon (b) | Right end Distance from last GFP codon | Transfectability of GFP mRNA |
| −6 | +11 | − |
| −6 | +113 | − |
| −44 | +11 | − |
| −44 | +113 | + |
| −44 | +122 | + |

Effect of the 5'-Cap on the mRNA

It is well known that capping highly increases the efficiency of mRNA translation (Cougot et al., *Trends Biochem. Sci.*, 29:436-444 (2004); Pestova, et al., *Proc. Natl. Acad. Sci.*, 98:7029-36 (2001)). The standard $m^7G(5')ppp(5')G$ in vitro capping analog can be incorporated in two orientations, therefore only one half of the mRNA product is active. Recently, Ambion and others introduced a new anti-reverse-cap-analog (ARCA) (Stepinski et al., *RNA*, 7:1486-95 (2001)), which lacks one of the 3'OH groups and can be incorporated in mRNA only in the correct orientation.

Using ARCA, a two-fold increase of GFP expression compared to the standard capping procedure was obtained, as demonstrated by (FIG. 2B).

Effect of the mRNA 3' Poly (A) Tail Length

There are two basic methods of construction of a poly(A) tail: insertion of a terminal poly(A/T) segment into the DNA template or direct addition of poly(A) residues to the RNA transcripts by a poly(A) polymerase. In these studies, a 3' terminal poly(A/T) stretch introduced by PCR with a reverse primer containing 100 b of poly(T) was sufficient for mRNA expression. However, posttranscriptional RNA polyadenylation by *E. coli* poly(A) polymerase (E-PAP), which expanded the poly(A) tail from 100 up to 300-400 nucleotides, resulted in an additional two-fold increase in expression. The expression could also be increased without tail extension when the ATP in the E-PAP reaction was replaced by modified ATP analogs: cordycepin or 8-azaadenosine (FIG. 2B). The stimulation of expression by poly(A) extension or by the insertion of ATP analogs probably provided better mRNA protection from 3'-exonuclease degradation. GFP expression was not affected by an excess of yeast tRNA, but was inhibited by an excess of free polyadenylate (FIG. 2B).

An optimized GFP mRNA construct contained 44b and 113b flanking UTR sequences, an ARCA cap, and a 300-400 b polyadenylate tail. The efficiency of mRNA and DNA transfection had the same pattern of dependence on the electroporation programs used: increasing strength of electroporation resulted in increasing the intensity of GFP expression for DNA and mRNA samples and decreasing of cell viability. Therefore the same nucleofector programs were effective for both DNA and RNA electroporation. After DNA electroporation using the most efficient program-T01, only one fourth of the EML cells were transfected, and these showed highly heterogeneous levels of expression. After mRNA electroporation, almost all cells appeared as a population uniformly expressing GFP. The level of GFP expression caused by plasmid DNA as well as by mRNA in EML cells was highest the day after transfection, and decreased to zero in 4 days (FIG. 3A).

The optimized mRNA construct was used to transfect different human cell lines. Nucleofector programs for each cell line were chosen in accordance with Amaxa cell line protocols. FACS analysis was conducted for EML and Jurkat cells transfected with green fluorescent protein ("GFP") mRNA: 6, 17, 50 and 150 mg mRNA/ml and 10 mg DNA/ml.

Figure 3A:
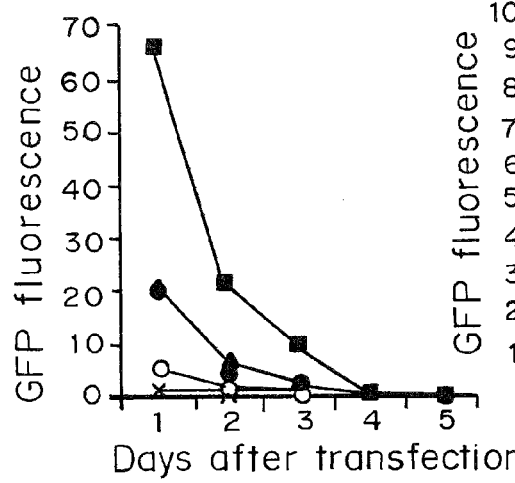
FIGS. 3A and 3B are line graphs showing the duration in days of GFP mRNA or DNA expression in Jurkat (3A) and EML (3B) cells. Cells transfected with GFP mRNA or DNA were analyzed by FACS during the duration of GFP expression. The expression efficiency was calculated as the difference between the geometric mean of fluorescence of the transfectants and control (mock transfected) cells. The fluorescence value of mock transfected cells was approximately 3 units (negative control). Therefore 63 and 603 units of total fluorescence correspond to 60 and 600 units increase of fluorescence above the control.
Figure 3B:
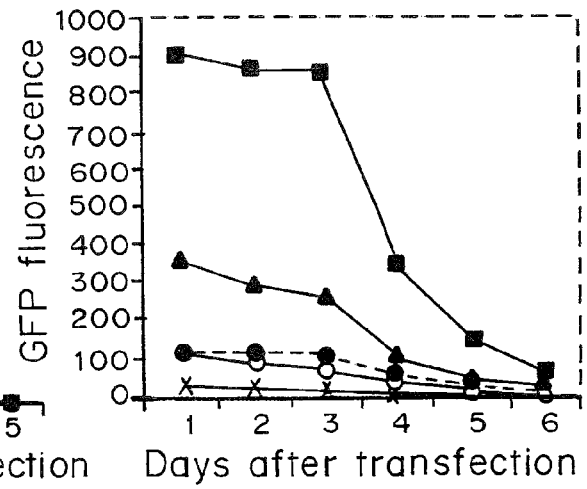

In all experiments mRNA transfected almost all of the cells, and resulted in highly efficient and uniform gene expression as shown in FIGS. 3A and 3B. Efficiency of transfection measured as the difference between mRNA transfected and mock transfected cell fluorescence.

TABLE 2

Efficiency of transfection measured as the difference between mRNA transfected and mock transfected cell fluorescence.

| | mRNA (mg/ml) | | | | DNA (mg/ml) |
|---|---|---|---|---|---|
| | 6 | 17 | 50 | 150 | 10 |
| EML | 3.9% | 54.4% | 89.8% | 95% | 27.4% |
| Jurkat | 88.8% | 96.2% | 97.1% | 97.0% | 81.4% |

Human cells can sustain GFP expression caused by plasmid DNA as well as by mRNA for a longer time than mouse EML cells, up to 10 days. Efficiency of transfection for different human cells calculated as the geometric mean fluorescence of the transfected population, showed striking superiority of mRNA expression to that of DNA Relatively long tem) GFP expression was also observed in the human B cell lines Bjab, BL2 and Palo.

Figure 3C:
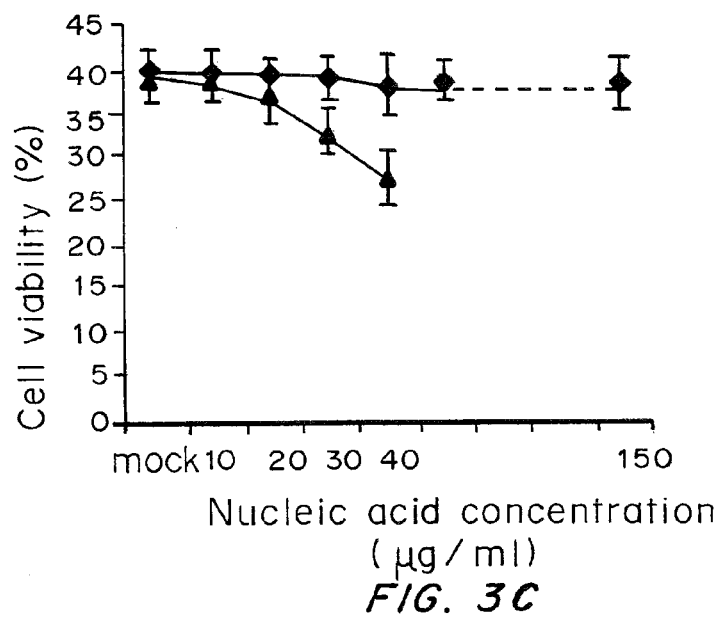
FIG. 3C is a line graph showing the viability of EML cells transfected with different levels of GFP plasmid DNA or mRNA. Viability was calculated by Trypan Blue dye exclusion (Phelach, In: Current protocols in Cell biology, John Wiley & Sons, Inc., 2006). The mean percent (±SD; n=3) of the cells collected 18 h after transfection is shown.

Plasmid DNA was toxic for the cells in a concentration of more than 20 μg/ml. In contrast, no toxicity of GFP mRNA was observed even when it was used at concentrations of more than 150 μg/ml (FIG. 3C).

Example 2

Transfection of Human Primary T Lymphocytes

Figure 4:
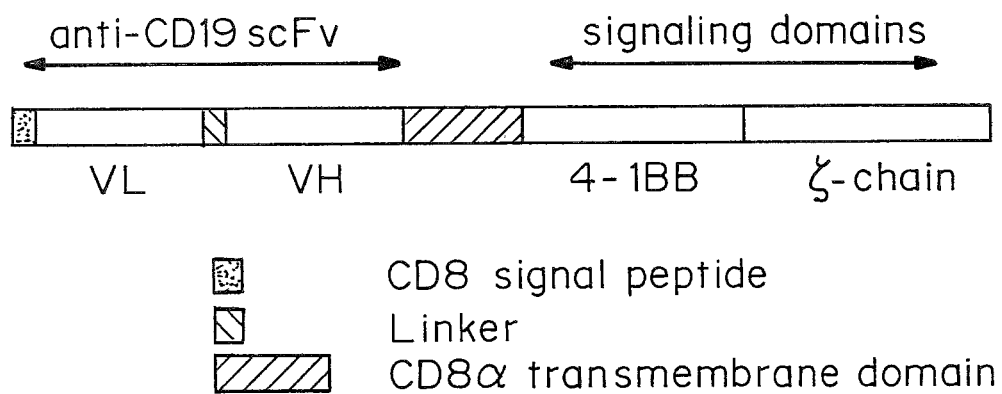
FIG. 4 is a schematic representation of the chimeric anti-CD19-CAR construct. $V_L$ and $V_H$—are extracellular single strand antibody domains, 4-1BB and ζ are intracellular signal domains.

The method of GFP mRNA synthesis was used to produce the mRNA of the human chimeric anti-CD19 receptor. This receptor contains a leader sequence, an antiCD19 single strand antibody domain, a transmembrane domain and two intracellular signal transduction domains: a 4-1BB and a CD3 zeta, as shown in FIG. 4. Cloned in the appropriate integrative DNA vector, the receptor is able to redirect transfected CD8+ lymphocytes as well as natural killer cells toward the CD19+ targets (Imai at al., *Leukemia*, 18, 676-684 (2004); Imai et al., *Blood*, 106:376-383 (2005). The plasmid pMSCV-IRES-antiCD19-BB-zeta was used as a template to produce the receptor mRNA. The product included the coding sequence, the 50 b 5'UTP, and the 84 b 3'UTP with an extended 400b polyA tail.

Jurkat cells transfected with this mRNA expressed receptor on their surface. Simultaneous transfection of the cells with the receptor and GFP mRNAs showed that both mRNAs can be delivered and expressed without interference. Double mRNA transfection occurred with the same pattern and efficiency as the transfection with single mRNA and was detected in more then 90% of cell population. Cells were transfected with 60 μg/ml anti-CD19-CAR mRNA and 20 μg/ml GFP mRNA, and analyzed by FACS 18h after transfection. Anti-CD19-CAR expression was detected with a goat anti-mouse (Fab)$_2$ polyclonal biotinylated antibody and streptavidin PerCP. More than 90% of cells expressed both transgenes.

Using pmaxGFP plasmid DNA, the transfection procedure for primary human T lymphocytes was optimized. The standard Amaxa Biosystems protocol for activated primary T cells recommends programs T20 and T23. However, these programs resulted in low viability of the cells. The protocol was optimized and better results were obtained with programs T3 and T7, which gave a relatively low but substantial level of pmaxGFP transfection with high viability (greater than 90%). When transfected with receptor mRNA, more than 80% of the CD3+ T lymphocytes expressed the receptor on their surface. Both the CD4+ and the CD8+ subpopulation were equally transfectable and showed the same kinetics of mRNA expression.

Example 3

Transfection of CD3+ T Lymphocytes with Anti-CD19-CAR mRNA

Figure 5:
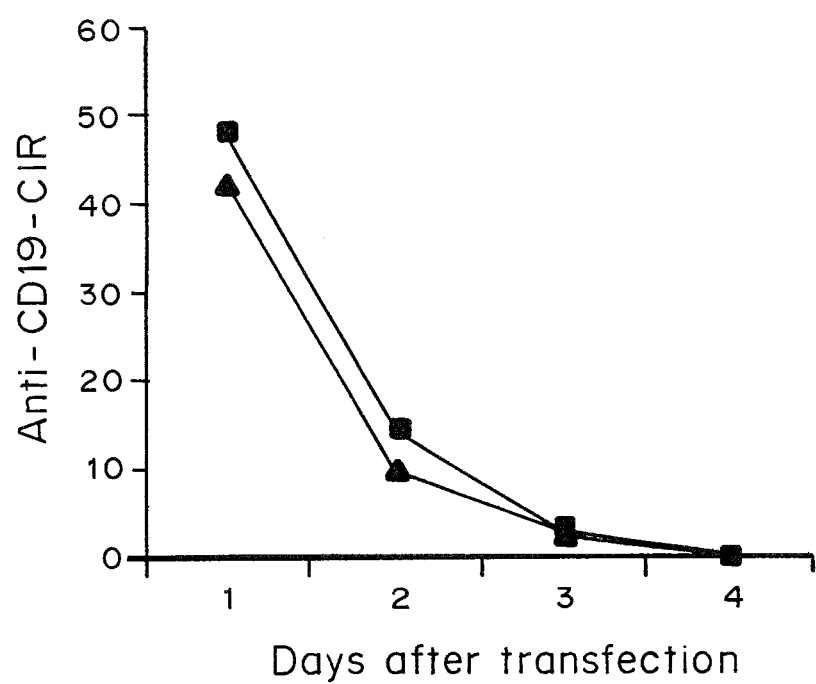
FIG. 5 is a line graph showing transfection of $CD3^+$ T lymphocytes with anti-CD19-CAR mRNA. Cells were transfected with 40 μg/ml anti-CD19-CAR mRNA and analyzed by FACS during duration (days). Cells were labeled using antibody specific to anti-CD19-CAR, CD8 and CD4. Anti-CD19-CAR expression efficiency was calculated as the difference between the geometric mean of fluorescence of the transfectants and control (mock transfected) cells. The fluorescence value of mock transfected cells was measured as approximately 3 units (negative control). Therefore 63 units of total fluorescence corresponded to 60 units increase of fluorescence above the control. (-■-)=CD4; (-♦-)=CD8.

Cells were transfected with anti-CD19-CAR mRNA (40 μg/ml) and analyzed by FACS. Cells were labeled with antibody able to detect surface expression of anti-CD19-CAR, CD8, and CD4. Anti-CD19-CAR expression efficiency was calculated as the difference between geometric means of fluorescence of the transfectants and control (mock-transfected) cells. The fluorescence value of mock-transfected cells was measured as approximately 3 units (negative control). Therefore 63 units of total fluorescence corresponded to a 60-unit increase in fluorescence relative to the control. Both the CD4+ and CD8+ subpopulations were equally transfectable, possessed the same pattern of mRNA expression, and were able to sustain anti-CD19-CAR expression for at least 3 days (FIG. 5).

Example 4

Cytotoxicity of CD8+ T Lymphocytes Transfected with Various Amounts of Anti-CD19-CAR mRNA FACS analysis of transfectants demonstrating various levels of anti-CD19-CAR expression. CD8+ T lymphocytes (CTLs) were transfected with various amounts of anti-CD19-CAR mRNA. Cells were mock transfected (FIG. 6A) or transfected with anti-CD19-CAR mRNA at 13.3 μg/ml (FIG. 6B), 40 μg/ml (FIG. 6C), or 120 μg/ml (FIG. 6D). The same transfectants were analyzed for cytotoxicity with different targets at the indicated E:T ratio. T lymphocytes were incubated for 4 hr with different target cells, loaded with 51Cr: (FIG. 6E) autologous cells; (FIG. 6F) allogeneic CD19+ B lymphoblasts; (FIG. 6G) CD19-K562 cells.

CD8+ T lymphocytes transfected with anti-CD19-CAR mRNA specifically killed CD19+ targets, whereas mock-transfected control lymphocytes were not cytotoxic. The CD19-negative target cell line K562 was resistant to receptor-mediated killing (FIG. 6G). Of note, even the minimal level of receptor expression detectable by FACS analysis was sufficient for target cell killing (FIGS. 6E and 6F). This result was reproduced with lymphocytes from three different donors.

The experiments above demonstrate that human lymphocytes can be transfected with anti-CD19 CAR mRNAs with high efficiency. After transfection virtually the whole cell populations uniformly expressed chimeric receptors and possessed cytotoxicity against allogeneic and autologous B cells. The expression of the receptor on the surface of lymphocytes was detected for at least 3 days after transfection (FIG. 5). Even the minimal detectable level of receptor expression was sufficient for cytotoxicity. The results in FIG. 5 demonstrates that transfected cytotoxic T lymphocytes (CTLs) can sustain their cytotoxicity for at least several days.

Example 5

Figure 7A:
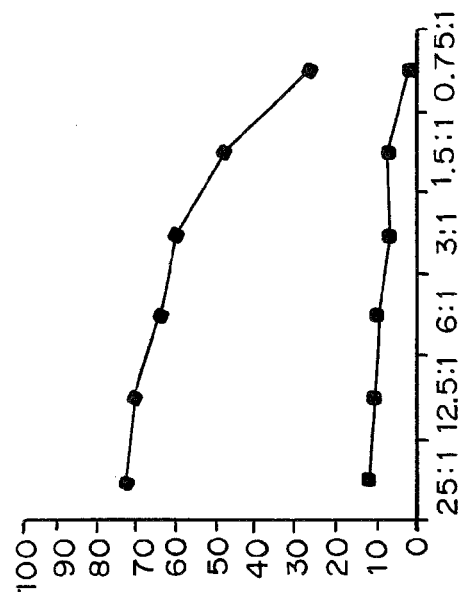
FIGS. 7A-7D are line graphs showing the cytotoxicity of anti-CD19 CAR+CTLs (-♦-) and mock transfected cells (-■-) against CD19+ tumor cells. CTLs were transfected with anti-CD19 CAR mRNA or mock transfected. Target cells (CD19-K562-negative control (FIG. 7A), and cells expressing CD19 antigen: Daudi, non-Hodgkin's lymphoma (FIG. 7B), autologous B cells (FIG. 7C), and NALM6, lymphoblastic leukemia (FIG. 7D)), were loaded with $^{51}$Cr and analyzed for cytotoxicity at the indicated E:T ratio.
Figure 7B:
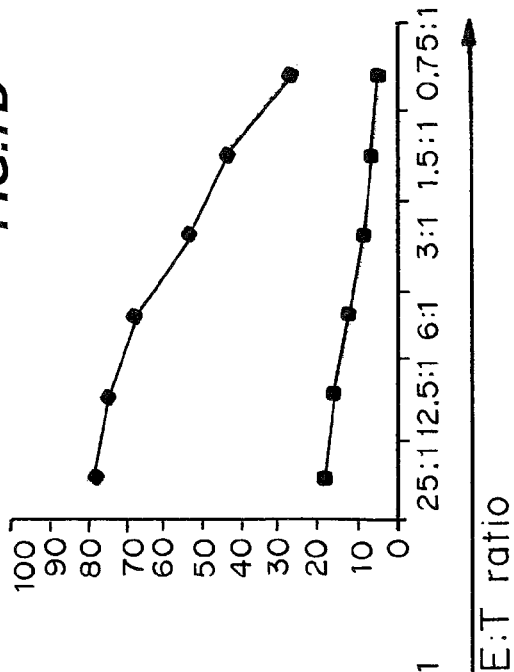
Figure 7C:
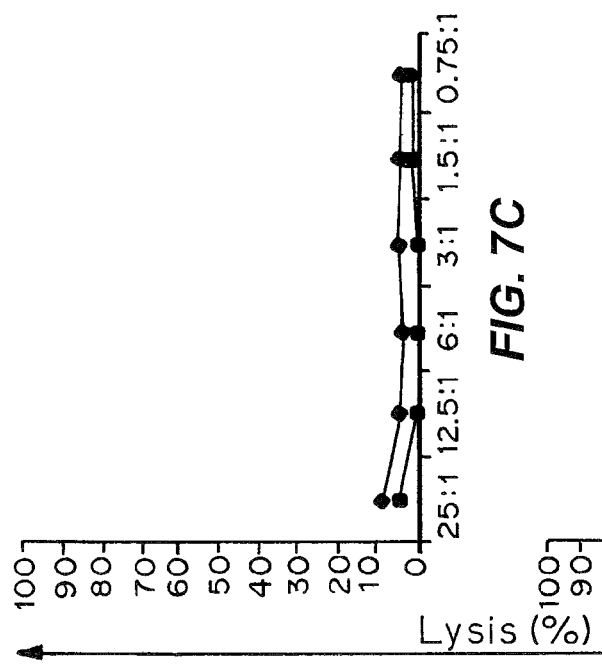
Figure 7D:
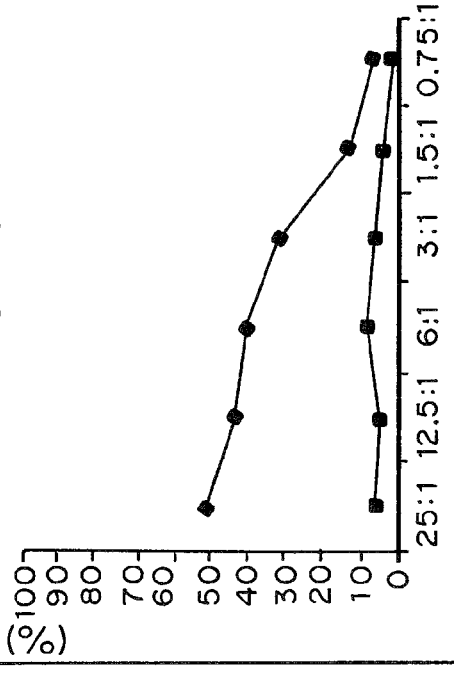

Cytotoxicity of CD8+ T Lymphocytes Transfected with Anti-CD19 Chimeric Receptor mRNA Against Different CD19+ Tumor Cells In a $^{51}$Cr assay, it was observed CAR-specific lysis of all CD19+ targets tested, including Daudi lymphoma and NALM6 leukemia cell lines, as well as autologous B lymphoblastoid cells, whereas mock-transfected control lymphocytes were not cytotoxic (FIG. 7B-7D). The CD19-negative target cell line K562 was resistant to receptor-mediated killing (FIG. 7A).

Example 6

Effect of Lymphocyte Activation on mRNA Transfection

The necessity of lymphocyte activation for mRNA transfection was analyzed. Because nucleofector program efficiencies were similar for both DNA and RNA electroporation (US, Amaxa), lymphocyte transfectability was determined using transient transfection with a GFP plasmid DNA. CD3+CD8+ lymphocytes taken without activation were electroporated with GFPmax plasmid DNA using the following different programs recommended by Amaxa for these cells: T7, T13, T20, U1, U8, U10, U5, U14, U9.

The T7 program was chosen for the next step. CD3+ CD8+ lymphocytes were incubated 1 or 7 days with CD3-CD28 beads and IL2 and then transfected with anti-CD19 CAR mRNA.

Non-activated CD3+CD8+ cells were virtually untransfectable: less then 2% of the whole population showed green fluorescence deter mined by expression of GFP transgene. CD3+CD8+ lymphocytes activated by 7 day incubation with CD3-CD28 beads and IL2 showed normal level of transfectability—up to 40% of the cells expressed GFP for programs T13 and T7, with correspondent viability 40 and 55%.

Figure 8A:
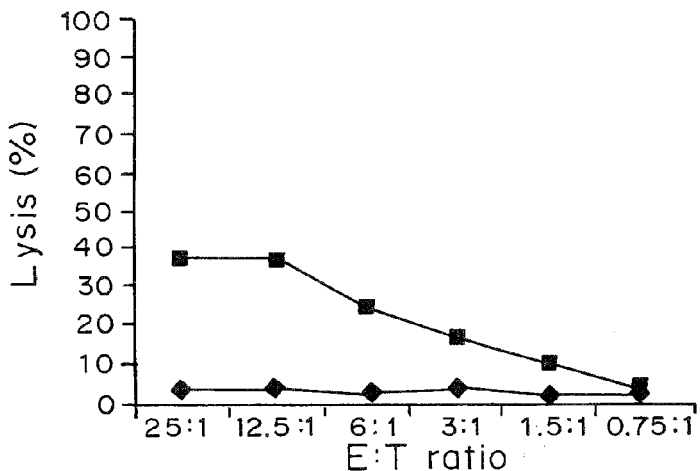
FIGS. 8A-8C are line graphs showing cytotoxicity (percent lysis) of transfected CTLs against autologous B cells at the indicated E:T ratios.
Figure 8B:
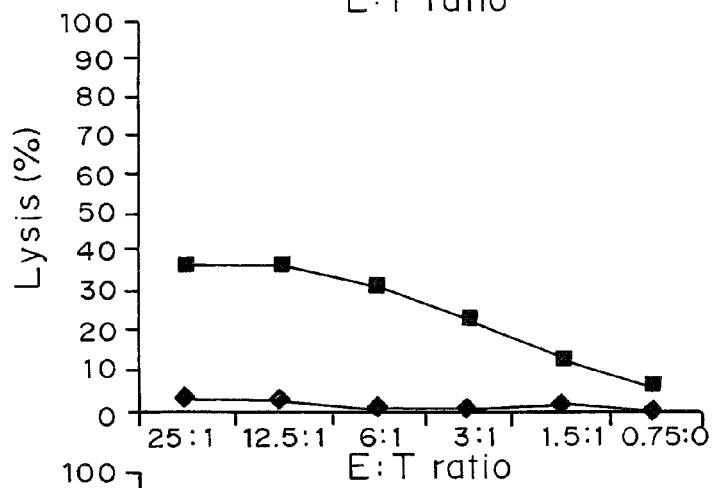

Both samples were transfected using the T7 program with similar efficiency and possessed the same level of cytotoxicity against CD19+ targets, as demonstrated by FIGS. 8A-8B. Therefore, CD8+ lymphocyte activation is essential for CAR mRNA transfection and one day of cell incubation with Cd3-CD29 beads and IL2 is sufficient for CTL activation.

Figure 8C:
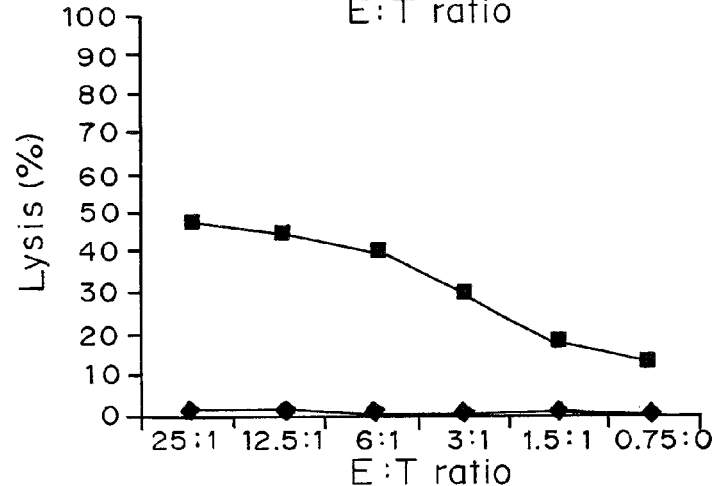

The presence of two signaling domains in the cytoplasmic part of CAR facilitates lymphocyte proliferation. However it was not clear if their activity can produce synergistic effects on receptor-mediated cytotoxicity. To investigate this, the 4-1BB signaling part of the anti-CD19 CAR was deleted by a 3-step PCR. This construct was transcribed into mRNA and compared with the original RNA. Both original CAR mRNA and the CAR mRNA construct with 4-1BB deletion transfected CTLs with similar efficiency and generated a similar level of cytotoxicity against CD19+ targets, FIG. 8C. Thus, in short run experiments where lymphocyte proliferation is not very important, the presence of the zeta subunit as a sole cytoplasmic domain in CAR is sufficient.

Example 7

Modulation Different Types of Lymphocytes with Anti-CD19 CAR mRNA

The killing efficiency of NK cells stably transfected with CD19 CAR has been previously demonstrated by Imai, et al., *Leukemia*, 18:676-684 (2004) using retroviral transduction. The ability to transfect NK cells as well as T cells from the same donor with CD19CAR mRNA was tested. Efficiency of electroporation depends on the source of lymphocytes, and electroporation should be optimized for each donor. Also, NK cells electroporation is often less efficient then electroporation of T cells (Amaxa).

Electroporation was optimized using cells obtained from a single donor. CD3+ T cells (CD4+ and CD8+) as well as CD56+ NK cells were transfected with GFP transgene. T7 Amaxa program with a T cell Amaxa kit was efficient for both cell groups and chosen for farther experiments. Three subpopulations: CD3+CD8+, CD3+CD4+ T cells and CD3- CD56+ NK cells were separated, electroporated with anti-CD19 CAR mRNA and tested for cell cytotoxicity toward autologous B cells. The lymphocytes subpopulations: CD8+, CD4+ T cells and a mixture of CD8+ and CD4+ cells (in a 1:1 ratio) as well as NK cells were transfected with anti-CD19 CAR mRNA. Target cells were loaded with $^{51}$Cr and analyzed for cytotoxicity. At the E:T ratios shown in FIGS. 9A-9D, all cell populations expressing the anti-CD19 chimeric receptor were cytotoxic. These studies demonstrate that there is no need to separate any specific type of cytotoxic cells in order to increase the efficiency killing target cells; rather the entire lymphocyte population could be used for mRNA CAR transfection.

Figure 10A:
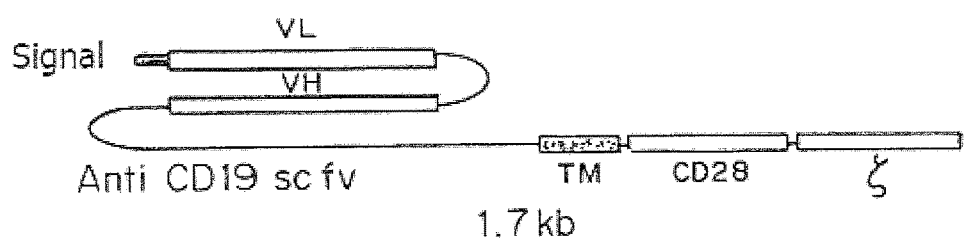
FIG. 10A shows the structure of CD276 (8H9) CAR, which can recognize B7-H3 antigen presented on various solid tumors (Cheung, et al. *Hybridoma and Hybridomics* 22(4):209-218 (2003).

Example 8 mRNA Reprogrammed CD276 CART Cells Demonstrate Robust Cytotoxicity Against Cancer Cells in vitro Materials and Methods Human CD8+ T cells were isolated from a patient with melanoma. The T cells were electroporated either with or without (mock) CD276 CAR mRNA (FIG. 10A), while the autologous melanoma cells, as well as other cancer cell line targets, were loaded with $^{51}$Cr. The CD8+Effector (E) T cells were added to the Target (T) cells at varying E:T ratios for four hours and the percent lysis was calculated based on the release of $^{51}$Cr.

Results

Another chimeric receptor which is made with the 8H9 antibody against a CD276 antigen protein often expressed on different tumor lines (Cheung et al., *Hybridoma and Hybridomics*, 22:209-218 (2003)) (see FIG. 10A) was introduced into human CTLs.

Transfection of CD8+ T lymphocytes with anti-CD276 CAR mRNA. Cells were transfected with anti-CD276-CAR mRNA (30 µg/ml) and analyzed by FACS. Cells were labeled with antibody able to detect surface expression of anti-CD276-CAR and CD8.

Cytotoxicity of CD8+ T lymphocytes transfected with various amounts of anti-CD276-CAR mRNA. CD8+ T lymphocytes (CTLs) were mock transfected or transfected with 30 µg/ml anti-CD276-CAR mRNA. CD8+ T lymphocytes transfected with anti-CD276-CAR mRNA specifically killed CD276+ targets, whereas mock-transfected control lymphocytes were not cytotoxic. The CD276-negative target cell line K562 was resistant to receptor-mediated killing.

Transfected lymphocytes killed all different solid tumor cells, such as primary melanoma, breast ductal carcinoma, rhabdosarcoma and breast adenacarcinoma which express the correspondent cancer antigen on their surface. The results are shown in FIGS. 10B-10F. Antigen negative K562 cells were resistant to such killing (FIG. 10B). CD276 CART cells exhibited dose dependent cytotoxicity of cells from T47D (FIG. 10C) and MCF7 (FIG. 10F) breast cancer cell, HTB82 rhabdomyosarcoma (FIG. 10D), and autologous melanoma (FIG. 10E) which do not express the CD276 antigen, but not control K562 cells (FIG. 10B).

The experiments above demonstrate that human lymphocytes can be transfected with anti-CD276 CAR mRNAs with high efficiency. After transfection virtually the whole cell populations uniformly expressed chimeric receptors and possessed cytotoxicity against allogeneic and autologous B cells. The expression of the receptor on the surface of lymphocytes was detected for at least 3 days after transfection. Even the minimal detectable level of receptor expression was sufficient for cytotoxicity. Transfected cytotoxic T lymphocytes (CTLs) can sustain their cytotoxicity for at least several days.

Example 9

Cytotoxic Activity of Anti-CD19 CAR+ CTLs in vivo

A xenogenic mice model for lymphocyte therapy of Daudi lymphoma described by Kowolik, et al., *Cancer Res.*, 66(22):10995-1004 (2006) was used. 9 none-obese diabetic/severe combined immunodeficiency (NOD/Scid) mice were divided into 3 groups. Each group was ip injected with either $1 \times 10^6$, $3 \times 10^6$ or $9 \times 10^6$ ffLuc Daudi cells per mouse and analysed by biophotonic measurements Exponentially growing tumors were established in all mice 3 days after injection. In an initial experiment 6 mice were ip injected with $3 \times 10^6$ ffLuc+Daudi cells and 3 days later therapy with human CTLs was initiated. Because the receptor stays on the CTL surface for about 3-4 days, the mice were injected with $5 \times 10^6$ CTLs per mice every third day. Half of the mice were injected twice on day 3 and day 6 after ffLuc Daudi lymphoma introduction, with mock CTLs (control) and the other half with anti-CD19 CAR mRNA modified CTLs. Treatment with modified cells resulted in marked regression of tumors, while in control group tumors continued to grow.

Figure 11:
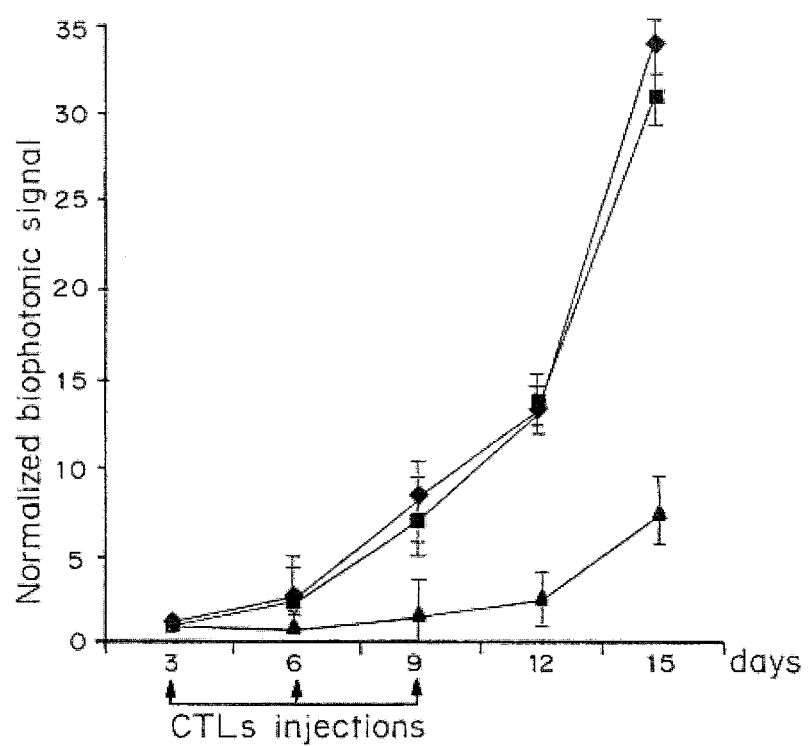
FIG. 11 is a line graph showing the in vivo activity of anti-CD19 CAR $^+$CTLs. 21 Nod-SCID mice were injected with $3 \times 10^6$ luciferase (ffLuc) expressing Daudi cells and developed exponentially growing tumors on day 3 after injection. These were imaged and divided into 3 groups: treated with RPMI medium (1), mock transfected (2) or anti-CD19 CAR transfected, (3) $CD8^+$ CTLs. Groups received injections of $5 \times 10^6$ CTLs on days 3, 6 and 9. The mice were imaged on days 3, 6, 9, 12 and 15. The graph is the longitudinal monitoring of the bioluminescent signals of ffLuc+ Daudi cells injected into groups of two NOD/scid mice. Points are the geometric mean photon flux (in p/s/cm2/sr), normalized against initial signal for each mouse; bars, geometric SD. (-♦-)=RPMI; (-■-)=13.3 mock; (-▲-)=CAR.

A larger experiment was then performed. $3 \times 10^6$ ffLuc Daudi cells per mice were seeded into the peritoneum of 24 NOD/Scid mice. 3 days later mice were analyzed by biophotonic measurements and were divided into 3 groups (8 mice per group, with median ffLuc signal (~$6 \times 10^8$ p/s/cm$^2$/sr), similar for each group. The mice were injected with $5 \times 10^6$ CTLs per mouse every third day and were given CTLs injections three times on days 3, 6 and 9. The mice were imaged on days 3, 6, 9, 12 and 15. Compared with tumor-bearing control mice given RMPI medium alone (group 1) and mock transfected CTLs (group2), there was significant reduction of tumor ffLuc signal in mice given anti-CD19 CAR mRNA transfected CTLs (group 3) (FIG. 11).

Pseudocolor image representing light intensity and anatomic localization of the ffLuc-Daudi cells in three representative mice and longitudinal monitoring of the bioluminescent signals of ffLuc+Daudi cells (FIG. 11) show that tumor growth inhibition was still evident 3 days after the last CTLs injection on day 12. For each group of mice the biophotonic signal outcome was normalized by the initial values at the beginning of CTL-mediated treatment. Geometric means of the signal was used for presentation based on the assumption of the lognormal distribution for the sizes of the tumors (Sprat, *J. Surgical Research*, 9:151-157 (1969)).

Several days after the end of T cell injections, presumably when CAR proteins were degraded, the tumors resumed growth. The finds are similar to the results obtained by DNA reprogramming reported by other groups (Cooper, et al., *Blood*, 105:1622-31 (2005)).

Example 10

RNA Reprogramming with BCL-XL and IL-2 Protects T Cells from Apoptosis and Cytokine Deficiency Materials and Methods $30 \times 10^6$ CD3+ T cells were electroporated with 30 µg/ml mRNA encoding GFP (mock), anti-apoptotic BCL-2, anti-apoptotic BCL-XL, or IL-2. The next day equal amounts of each sample ($5 \times 10^6$ cells) were transferred in triplicate into IL-2—depleted medium. Cell viability counts were then performed daily using trypan blue.

Results

Deficiency of stimulating signals including homeostatic cytokines, such as IL-2, is a serious factor impeding CAR-T cell activity in vivo. This situation can be modeled in vitro by depleting IL-2 from the culture medium. Within IL-2-depleted medium, human CD19 CAR-T cells do not proliferate and within 2 days about 50% undergo apoptosis.

Figure 12:
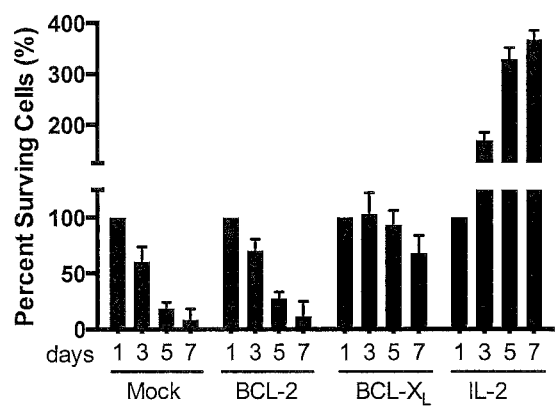
FIG. 12 is a bar graph showing the influence of anti-apoptotic and cytokine mRNAs (mock, BCL-2, BCL-XL, IL-2) transfection (day 0) on CD3+ T cell viability (Percent Surviving Cells) ex vivo in IL-2 depleted medium over time (days). Cell viability at day 1 was taken as 100%.

CD3+ T cells with 30 µg/ml mRNA encoding GFP (mock), anti-apoptotic BCL-2, anti-apoptotic BCL-XL, or IL-2. The next day equal amounts of each sample were transferred in triplicate into IL-2—depleted medium. The results are illustrated in FIG. 12. BCL-XL mRNA transfer preserved greater than 95% cell viability for 5 days after transfection. BCL-2 was not protective relative to control. T cells transfected with IL-2 were able to propagate for at least 7 days after transfer to IL-2—depleted media.

Example 11

BIM SAHB and ABT-737 Reactivate Apoptosis in a Panel of Mantle Cell Lymphomas

Materials and Methods

A panel of mantle cell lymphoma (MCL) cell lines were exposed to BIM SAHB$_A$, BIM SAHB$_A$(R153D), or vehicle alone for 24 hours in OptiMEM medium followed by viability testing using the CELLTITER-GLO® (Promega) assay.

Results

Figure 13:
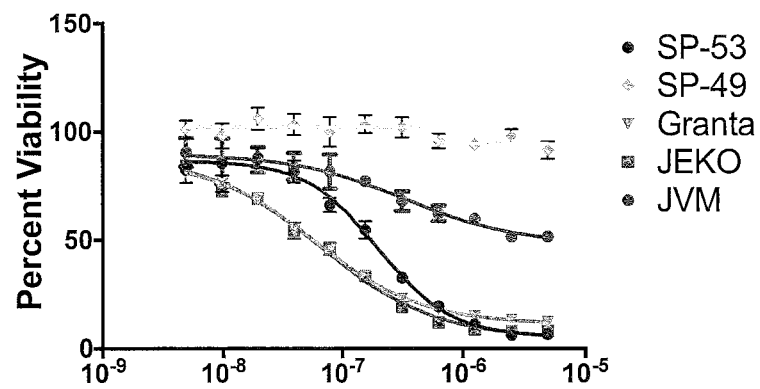
FIG. 13 is a line graph showing viability (percent) of various mantle cell lymphoma (MCL) cancer cell lines (SP-53, SP-49, Granta, JEKO, and TVM) following treatment with various concentrations (M) of the BH3 mimetic ABT-737.
Figure 14A:
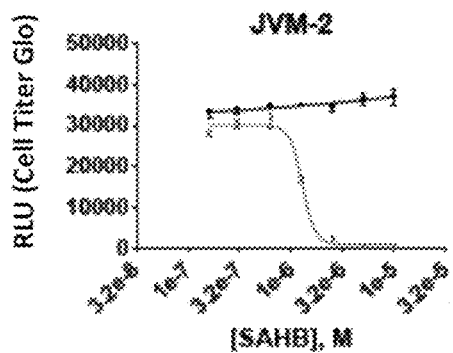
FIGS. 14A-14D are plots showing viability (Relative Light Units) following a CELLTITER-GLO® assay of various mantle cell lymphoma (MCL) cancer cell lines: JVM-2 (FIG. 14A), Granta-519 (FIG. 14B), JEKO-1 (FIG. 14C), and SP-53 (FIG. 14D) following treatment with various concentrations (M) of the BH3 mimetic BIM SAHB (-■-), or a BIM SAHB R153D variant control (-●-).
Figure 14B:
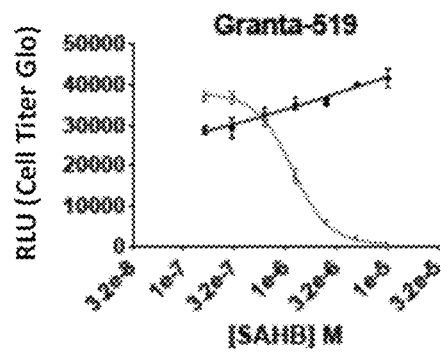
Figure 14C:
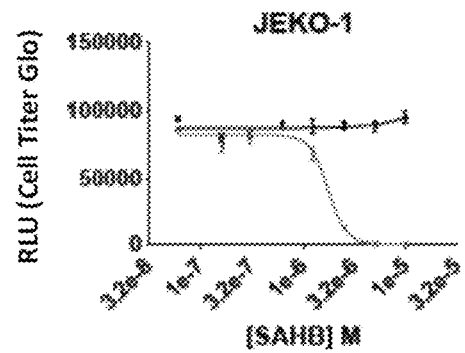
Figure 14D:
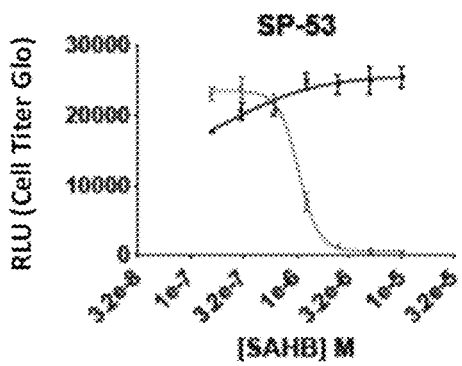
Figure 15A:
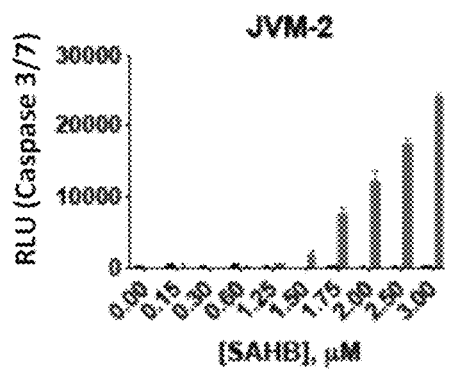
FIGS. 15A-15D are plots showing caspase 3/7 activation (Relative Light Units) in various mantle cell lymphoma (MCL) cancer cell lines: JVM-2 (FIG. 15A), Granta-519 (FIG. 15B), JEKO-1 (FIG. 15C), and SP-53 (FIG. 15D) following treatment with various concentrations (μM) of the BH3 mimetic SAHB (right hand bar in each pair), or a SAHB R153D variant control (left hand bar in each pair).
Figure 15B:
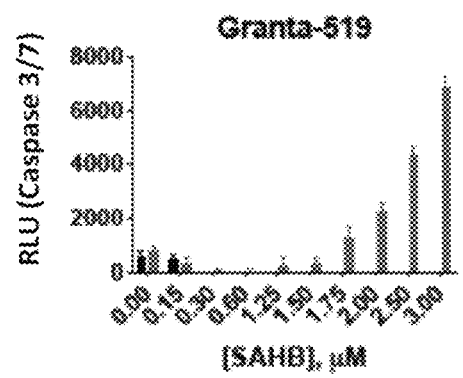
Figure 15C:
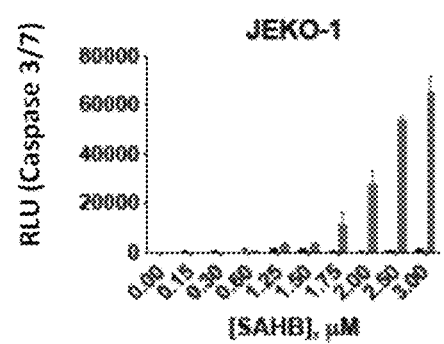
Figure 15D:
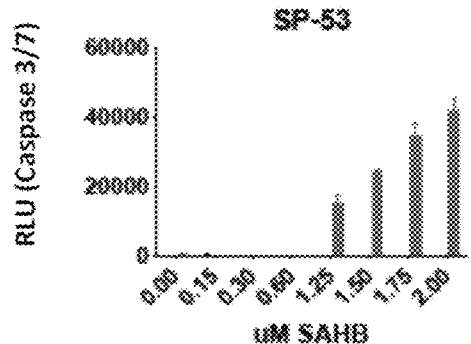
Figure 16:
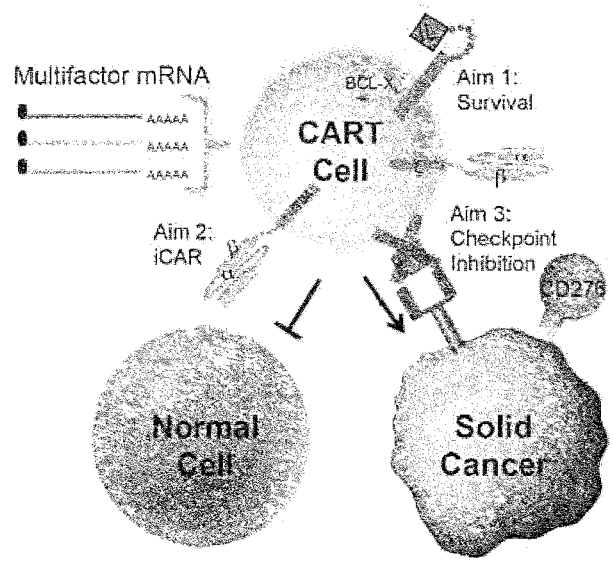
FIG. 16 is an illustration showing an exemplary single-step multifactor mRNA reprogramming strategy to improve targeting of CD276-positive solid cancers by improving CART cell survival, ability to distinguish normal tissues, and ability to evade immune silencing.

The ability of cell-permeable BIM SAHB to activate apoptosis was assessed in a panel of MCL cell lines. Whereas BIM SAHB$_A$ impaired viability in a dose-dependent manner with EC50s in the low micromolar range, BIM SAHB$_A$(R153D) had little to no effect. Moreover, the impaired cancer cell viability correlated with caspase 3/7 activation in the BIM SAHB$_A$-treated MCL lines, indicating that BIM SAHB functioned through the apoptotic pathway (FIGS. 14A-14D, 15A-15D). ABT-737 also elicited reduced viability in a subset of the MCL cell lines (FIG. 13).

Example 12 mRNA Reprogrammed CD276 CART Cells Demonstrate Anti-cancer Activity in a Xenogeneic Model In Vivo Materials and Methods Transfection of CD8+ T lymphocytes with anti-CD276 CAR mRNA. Cells were transfected with anti-CD276-CAR mRNA (30 µg/ml) and analyzed by FACS. Cells were labeled with antibody able to detect surface expression of anti-CD276-CAR and CD8.

A2058 human melanoma cells (CD276 positive) were injected subcutaneously (SC) into nine NOD-SCID-γc−/− mice ($10^6$/mouse). Media, 5 million human CD8+ T cells mock electroporated without mRNA, or 5 million human CD8+ T cells electroporated with CD276 CAR mRNA were intraperitoneally (IP) injected into the mice on days 3, 6, 9, 12 and 18. After three weeks the tumors were excised and weighed.

Results

Figure 17:
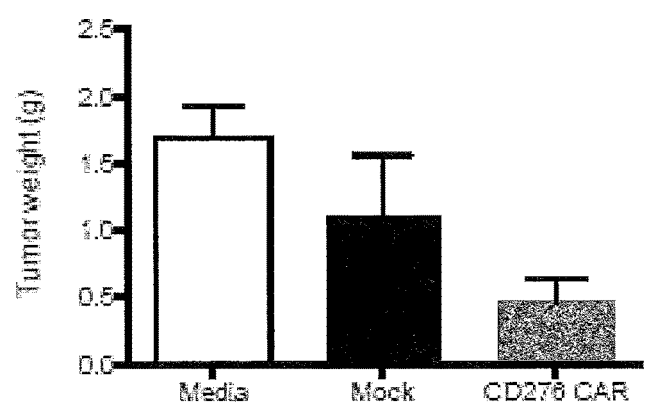
FIG. 17 is a bar graph showing tumor weight (grams) after subcutaneous (SC) injection of human A2058 melanoma cells in NOD/SCID mice and intraperitoneal (IP) treatment with media alone, mock electroporated or CD276 CAR electroporated human T cells.

The results are shown in FIG. 17. While mock electroporated T cells reduced tumor size presumably due to allogeneic differences, CD276 CAR reprogrammed T cells trended toward even further decreased tumor burden.

Example 13 mRNA Transfection of Human Fibroblasts

Materials and Methods

Cells

Neonatal foreskin keratinocytes and neonatal human foreskin fibroblasts were obtained from the Yale Cell Culture Core Facility. Keratinocytes were cultured in serum-free low calcium medium (Epilife, Invitrogen); fibroblasts were cultured in DMEM medium in 10% heat-inactivated fetal bovine serum (Gibco). For reprogramming with mRNA constructs, keratinocytes were electroporated with mRNA transcripts corresponding to reprogramming factors as described below. For initial experiments mRNA corresponding to each of four transcription factors (OCT4, SOX2, KLF4, c-MYC) were used in a 1:1:1:1 ratio respectively. For experiments using high OCT4 concentrations, the same four factors were used in a 3:1:1:1 ratio. For experiments using the initial four factors plus either NANOG or P53DD, the five mRNA transcripts were present in a ratio of 1:1:1:1:1. After viral infection or electroporation, keratinocytes were grown in fresh serum-free, low calcium medium at 37 C and 5% $CO_2$ for 2 days, after which they were trypsinized and seeded onto multi-well plates containing irradiated mouse fibroblasts. Transfected cells were seeded $2.5 \times 10^6$ cells/$cm^2$ and cultured with ES cell medium (DMEM/F12 containing 20% KOSR (vol/vol), 5-10 ng $ml^{-1}$ bFGF, 1 mM L-Gln, 100 µM nonessential amino acids, 100 M 2-mercaptoethanol, 50 U $ml^{-1}$ penicillin and 50 mg $ml^{-1}$ streptomycin). Neonatal human foreskin fibroblasts were used to confirm the expression of individual mRNA constructs of the various reprogramming factors and were cultured in DMEM with 10% heat inactivated fetal bovine serum. Western blot analysis was used to confirm the expression of individual mRNA constructs of the various reprogramming factors.

PCR

Gene amplification was performed with AccuPrime Pfx DNA polymerase (Invitrogen) according to the manufacturer's protocol. 25 to 30 cycles of PCR were performed in standard 50-µl reaction using 0.1 µg of template DNA. The forward primer contained the T7 RNA promoter and an anchoring sequence in the proximal part of the gene expression cassette. The reverse primer, with anchoring sequence in the distal part of the gene expression cassette, contained a stretch of 100 dT residues. 3-step PCR to delete 4-1 BB signaling part of the anti-CD19 CAR was performed by a standard procedure.

RNA Synthesis mRNA constructs based on the Pontelina plumata green fluorescent protein ("GFP") sequence of prnaxGFP plasmid (Amaxa Biosystems) were produced in vitro using T7 RNA polymerase (RNAP). Forward primer contained T7 RNA P promoter and anchoring sequence to the proximal part of the GFP expression cassette. Reverse primer with anchoring sequence to distal part of GFP expression cassette contained a stretch of 100 oligo-dT.

mRNA synthesis was performed with mMESSAGE mMASHINE® kit (Ambion), using the procedure recommended by the manufacturer. One hundred to 200 ng of DNA made by PCR with no further purification was used for the standard 20 µl transcription reaction. The product was treated with *Escherichia coli* poly (A) polymerase (from the same kit) in the presence of 1 mM ATP according to the Ambion polyadenylation protocol. The yield of mRNA was 20 to 60 g of mRNA per reaction. The final product was treated with DNase I (Ambion) and purified with an Ambion MEGAclear kit or by LiCl precipitation. RNA quality was verified by agarose gel electrophoresis, and RNA was stored at −80° C.

In some cases the product was additionally polyadenylated using the reagent of the same kit. The final product was treated with DNaseI and purified by Ambion MEGAclear kit or by LiCl precipitation.

Transfections

Electroporation was performed using an Amaxa NUCLEOFECTOR™-II (Amaxa Biosystems, Cologne, Germany) in accordance with manufacturer recommendations. All cells were electroporated with use of 30-120 mg/ml mRNA per sample. Cells were used in a concentration of 10-250 million per ml. In this interval of values the efficiency of transfection does not depend on cell density. The efficiency of transfection was determined by FACS 18 hours after transfection. Cell viability was determined by trypan blue exclusion.

Cells were used in a concentration of 10-50 million per ml. In this interval of values the efficiency of transfection does not depend on cell density. The efficiency of transfection was determined by FACS eighteen hours after transfection. Cell viability was determined by trypan blue exclusion.

Cationic-liposomal transfection experiments were carried out using the TransIT®-mRNA Transfection Kit (Mirus Bio, WI 53711). Conditions were optimized for keratinocyte and fibroblast transfection according to the manufacturer's recommendations. Transfection of both keratinocytes and fibroblasts was performed in cell culture conditions on a feeder layer of irradiated mouse embryonic fibroblasts.

Flow Cytometry

Flow cytometry was performed using the fluorescent activated cell sorting (FACS®) assay. Flow cytometry was performed on cell subpopulations was performed at the Yale Cancer Center Flow Cytometry Shared Resource, using a FACS® Calibur flow cytometer (Becton-Dickinson, San Jose, Calif.) equipped with 488 nm laser and the standard filter setup. Fluorescence signals were collected on a logarithmic scale. A minimum of ten thousand cells were interrogated for each sample. Analysis of data was performed using FlowJo software (Tree Star, Inc., San Carlos, Calif.). The expression efficiency was calculated as the difference between the geometric mean of fluorescence of the transfectants and control (mock transfected) cells.

Electrophoresis

DNA samples were run in 1% agarose in Tris-acetate buffer, 2 v/cm RNA samples were run in 1% agarose in MOPS-formaldehyde buffer, 2 v/cm, using RNA Millenium marker (Invitrogen) as size standard.

Results

To assess the functionality of mRNA transcripts, transcripts for OCT4, SOX2 (Genbank accession no. NP_003097.1 (protein), NM_003106.2 (mRNA/cDNA)), KLF4 (Genbank: AAH30811.1 (protein), BC030811.1 (mRNA/cDNA)), c-MYC (Genbank: CAA25288.1 (protein), X00676 (mRNA/cDNA)), and NANOG (Genbank: AAP49529.1 (protein), AY230262 (mRNA/cDNA)) were individually transfected into neonatal human foreskin fibroblasts. Protein synthesis was assessed by Western blot analysis. Upon transfection each transcript allowed for significant protein production compared with untransfected control fibroblasts. Sample quantities were standardized by determining pre-lysis cell quantity or by protein quantitation of cell lysates by the bicinchoninic acid (BCA) protein assay.

In all cases protein synthesis was evident above levels of untransfected control samples.

Example 14 mRNA Transfection of Human Keratinocytes

Keratinocytes were transfected with mRNA transcripts coding for reprogramming transcription factors. Initially, keratinocytes were electroporated with OCT4, SOX2, KLF4, and c-MYC mRNA transcripts (day 0). After transfection, cells were grown in keratinocyte medium for 2 days without a feeder cell layer. On day 2, cells were trypsinized and moved to feeder cell layers in multi-well plates with or without 10 mM valproic acid (VPA) supplement.

Transfected keratinocytes began to show evidence of transformation on day 4, at which time small colonies began to form that were particularly abundant in VPA-containing cultures. No colonies were observed in untransfected control cells in either the presence or absence of VPA Example 15 siRNA Transfection of Jurkat Cells

Jurkat T cells were electroporated with different amount of FITC labeled siRNA. The condition and the kinetics of siRNA transfection were identical to mRNA transfection. Transfection of Jurkat cells with EGFP mRNA (Clontech) and anti-GFP siRNA (GCAAGCUGACCCUGAAGUU-CAU) resulted in 80% inhibition of GFP mRNA expression the day after transfection. No toxicity in siRNA transfection was observed in the interval of 0-15 mkg siRNA/ml.

Example 16

Transfection of Human Keratinocytes with a Combination of OCT4, SOX2, KLF4, c-MYC, and NANOG mRNAs Results in mRNA-directed Reprogramming Materials and Methods Cell Culture Neonatal foreskin keratinocytes were obtained from the Yale Cell Culture Core Facility. Keratinocytes were cultured in serum-free low calcium medium (Epilife, Invitrogen); After transfection keratinocytes were grown in fresh serum-free, low calcium medium at 37 C and 5% CO2 for 2 days, after which they were trypsinized and seeded onto multi-well plates containing irradiated mouse fibroblasts. Transfected cells were seeded $2.5 \times 10^6$ cells/cm$^2$ and cultured with ES cell medium.

RNA Synthesis

As described above, green fluorescent (GFP) mRNA constructs were produced in vitro with T7 polymerase and were based on the Pontellina plumata GFP sequence of plasmid pmaxGFP (Amaxa Biosystems, Cologne, Germany). OCT4, SOX2, KLF4, c-MYC, P53DD, and NANOG constructs were created by replacing the GFP coding region in pmaxGFP with the appropriate open reading frame from each gene. DNA templates were produced by polymerase chain reaction (PCR) using AccuPrime Pfx DNA polymerase (Invitrogen) according to manufacturer's protocol. Twenty-five to 30 cycles of PCR were performed in a standard 50-μl reaction using 0.1 mg of template DNA. The forward primer contained the T7 RNA promoter and an anchoring sequence in the proximal part of the gene expression cassette. The reverse primer, with anchoring sequence in the distal part of the gene expression cassette, contained a stretch of 100 dT residues.

mRNA synthesis with T7 RNA polymerase is described above This was performed with an mMESSAGE mMACHINE T7 Ultra kit (Ambion, Austin, Tex.), using the procedure recommended by the manufacturer. The product was treated with *Escherichia coli* poly(A) polymerase (from the same kit) in the presence of 1 mM ATP according to the Ambion polyadenylation protocol. The final product was treated with DNase I (Ambion) and purified by LiCl precipitation.

Transfection

Electroporation was performed with an Amaxa Nucleofector II (Amaxa, Gaithersburg, Md.) in accordance with manufacturer recommendations. Keratinocytes were electroporated with "Human Keratinocyte Nucleofector Kit Solution" and programs T007, T018, and T024. The efficiency of transfection was determined by flow cytometry 18 hours after transfection. Cell viability post-transfection was assessed by tryptan blue staining hemocytometry as well as by FACS data. In standard reprogramming experiments, OCT4, SOX2, KLF4, and c-MYC were used in a 1:1:1:1 ratio with 30 μg/ml final concentration of each factor. In experiments containing high OCT4, a 3:1:1:1 ratio was used. In experiments using NANOG, a 1:1:1:1:1 ratio (OCT4: SOX2:KLF4:c-MYC:NANOG) was used.

Alkaline Phosphatase Analysis

Direct alkaline phosphatase (AP) activity was assessed using Alkaline Phosphatase Staining Kit (Stemgent, Inc, Cambridge, Mass.) according to the manufacturer's recommendations.

Results

Keratinocytes transfection with mRNAs were compared to representative colonies of human embryonic stem cells (hES H1 P60) grown on matrigel and stained for alkaline phosphatase activity. Small round cells were produced from electroporation of five transcription factor mRNAs (OCT4, SOX2, KLF4, c-MYC, and NANOG) into neonatal human epidermal keratinocytes and stained for alkaline phosphatase activity at day 16 post transfection.

This experiment shows that transfection of human keratinocytes with a combination of OCT4, SOX2, KLF4, c-MYC, and NANOG mRNAs results in mRNA-directed reprogramming, changing the morphologic and immunologic phenotype of human keratinocytes toward that of IPS cells. Furthermore, alkaline phosphatase staining can be used as a standard marker that indicates the formation of IPS cells in de-differentiation experiments.

Modifications and variations will be obvious to those skilled in the art and are intended to come within the scope of the appended claims.

We claim:

1. An immune cell comprising one or more RNAs prepared by in vitro transcription,
   wherein at least one of the RNAs encodes a chimeric antigen receptor (CAR) polypeptide that renders the immune cell specific for a cancer antigen expressed on the surface of cells of a subject, and
   wherein the cell is free of DNA encoding the CAR polypeptide.

2. The cell of claim 1, wherein the one or more RNAs are prepared by in vitro transcription of a linear double stranded DNA template prepared by polymerase chain reaction (PCR).

3. The cell of claim 1, wherein the RNA encoding the CAR polypeptide is prepared by in vitro transcription of a linear double stranded DNA template comprising:
   an RNA polymerase promoter on the coding strand of the double-stranded DNA,
   a 5' untranslated region effective for translation of the RNA into the encoded CAR polypeptide after transfection into a eukaryotic cell,
   an open reading frame that encodes the CAR polypeptide,
   3' untranslated region effective for translation of the RNA into the encoded CAR polypeptide after transfection into a eukaryotic cell, and a poly(A) stretch,
   wherein the promoter is heterologous to the open reading frame, and wherein the DNA template terminates with the 3' end of the poly(A) stretch.

4. The cell of claim 1, wherein the immune cell is transfected with an effective amount of RNA encoding the CAR polypeptide for the CAR polypeptide to be detected on the surface of the immune cell.

5. The cell of claim 4, wherein the CAR is a CD19 CAR.

6. The cell of claim 5, wherein the CD19 CAR comprises
   (i) an anti-CD19 single strand antibody domain, a transmembrane domain, a 4-1BB domain, and a CD3 zeta domain; or
   (ii) an anti-CD19 single strand antibody domain, a transmembrane domain, and a CD3 zeta domain.

7. The cell of claim 1, wherein at least one of the RNAs encodes a factor or factors that modulate the cell's metabolism.

8. The cell of claim 1 further comprising one or more RNAs that render the cell resistant to one or more inhibitory molecules selected from siRNAs or an mRNA encoding a protein antagonist of the inhibitory molecule or a signaling pathway thereof.

9. The cell of claim 1, wherein the cell is a T cell, macrophage, dendritic cell, B cell, Natural Killer (NK) cell, Natural Killer T (NKT) cell, or Cytokine Induced Killer (CIK) cell.

10. The cell of claim 4 comprising one or more CAR or CARs targeting one or more antigens selected from the group consisting of CD33, CD123, and CD276.

11. The cell of claim 7, wherein the factor or factors that modulate the cell's metabolism is IL-2, IL-7, IL-15, BCL-XL, BCL2, A1, MCL1, chimeric interleukin receptor, or a combination thereof.

12. The cell of claim 1, further comprising one or more RNAs that render the cell resistant to one or more inhibitory molecules, the inhibitory molecules selected from the group consisting of CTLA-4, PD-1, LAG-3, 2B4, BTLA, TGF beta receptor dominant negative analog, and combinations thereof.

13. The cell of claim 8, wherein the RNAs are RNAs encoding cas9 Krab fusion protein, a CRISPR-like protein fused to a transcription inhibitory domain(s), and/or guide RNAs for CRISPR.

14. The cell of claim 1 further comprising RNA encoding an inhibitory chimeric antigen receptor (iCAR).

15. The cell of claim 14, wherein the iCAR targets an antigen selected from the group consisting of CD123 and hepatic asialoglycoprotein receptor.

16. The cell of claim 1 comprising one or more CAR wherein the CAR or CARs targets an antigen selected from the group consisting of CD19, CD33, CD123, CD276, or a combination of CD33 and CD123;
   one or more transfected RNAs encode a factor or factors that modulates the cell's metabolism selected from the group consisting of IL-2, BCL-XL, CγCR, BCL2, anti-apoptotic gene constructs thereof, and combinations thereof; and wherein the cell further comprises
   (i) one or more transfected RNAs that render the cell resistant to one or more inhibitory molecules selected from the group consisting of CTLA-4, PD-1, LAG-3, 2B4, BTLA, TGF beta receptor dominant negative analog, and combinations thereof;
   (ii) one or more RNAs encoding an iCAR; or
   (iii) a combination of (i) and (ii).

17. The cell of claim 7, wherein the at least one polypeptide that modulates the cell's metabolism comprises a combination of BCL-XL and IL-2 polypeptides.

18. The cell of claim 7, wherein the polypeptide that modulates the cell's metabolism increases viability or reduces apoptosis.

* * * * *

UNITED STATES PATENT AND TRADEMARK OFFICE
CERTIFICATE OF CORRECTION

Page 1 of 1

PATENT NO. : 10,155,038 B2
APPLICATION NO. : 15/008376
DATED : December 18, 2018
INVENTOR(S) : Peter M. Rabinovich et al.

It is certified that error appears in the above-identified patent and that said Letters Patent is hereby corrected as shown below:

In the Claims

Claim 16, Column 66, Line 32, replace "or" with --and--.

Signed and Sealed this
Fourth Day of June, 2019

Andrei Iancu
*Director of the United States Patent and Trademark Office*